(12) United States Patent
Kogel

(10) Patent No.: US 11,441,147 B2
(45) Date of Patent: Sep. 13, 2022

(54) RNAI FOR THE CONTROL OF PHYTOPATHOGENIC FUNGI AND OOMYCETES BY INHIBITING THE EXPRESSION OF CYP51 GENES

(71) Applicant: BASF SE, Ludwigshafen (DE)

(72) Inventor: Karl-Heinz Kogel, Lollar (DE)

(73) Assignee: BASF SE, Ludwigshafen am Rhein (DE)

( * ) Notice: Subject to any disclaimer, the term of this patent is extended or adjusted under 35 U.S.C. 154(b) by 40 days.

(21) Appl. No.: 14/904,045

(22) PCT Filed: Jul. 9, 2014

(86) PCT No.: PCT/EP2014/064686
§ 371 (c)(1),
(2) Date: Jan. 8, 2016

(87) PCT Pub. No.: WO2015/004174
PCT Pub. Date: Jan. 15, 2015

(65) Prior Publication Data
US 2016/0215290 A1    Jul. 28, 2016

(30) Foreign Application Priority Data

Jul. 10, 2013   (EP) .................................. 13175924

(51) Int. Cl.
*C12N 15/82* (2006.01)
*C12N 15/113* (2010.01)
*A01N 57/16* (2006.01)

(52) U.S. Cl.
CPC .......... *C12N 15/1137* (2013.01); *A01N 57/16* (2013.01); *C12N 15/8218* (2013.01); *C12N 15/8282* (2013.01); *C12N 2310/14* (2013.01); *C12N 2310/51* (2013.01); *C12N 2310/531* (2013.01); *C12Y 114/1307* (2013.01)

(58) Field of Classification Search
CPC ................................................ C12N 15/1137
USPC ................................................. 800/301, 312
See application file for complete search history.

(56) References Cited

U.S. PATENT DOCUMENTS

| | | | |
|---|---|---|---|
| 4,407,956 A | 10/1983 | Howell | |
| 4,536,475 A | 8/1985 | Anderson | |
| 5,639,952 A | 6/1997 | Quail et al. | |
| 5,689,044 A | 11/1997 | Ryals et al. | |
| 6,043,410 A | 3/2000 | Wilkinson | |
| 6,184,443 B1 | 2/2001 | Pedersen et al. | |
| 6,242,667 B1 | 6/2001 | Bujard et al. | |
| 6,252,136 B1 | 6/2001 | Bujard et al. | |
| 6,255,560 B1 | 7/2001 | Fraley et al. | |
| 6,379,945 B1 | 4/2002 | Jepson et al. | |
| 6,429,362 B1 | 8/2002 | Crane | |
| 6,504,082 B1 | 1/2003 | Albertsen et al. | |
| 6,566,586 B1 | 5/2003 | Stalker et al. | |
| 6,642,437 B1 | 11/2003 | Lemaux et al. | |
| 2001/0047525 A1 | 11/2001 | Bruce et al. | |

FOREIGN PATENT DOCUMENTS

| | | |
|---|---|---|
| EP | 0067553 A2 | 12/1982 |
| EP | 0159884 B1 | 2/1993 |
| EP | 0310619 B1 | 4/1994 |
| EP | 0270356 B1 | 6/1994 |
| EP | 0342926 B1 | 9/1994 |
| EP | 0116718 B2 | 5/1996 |
| EP | 0787194 A1 | 8/1997 |
| EP | 0968292 A1 | 1/2000 |
| EP | 0973922 A2 | 1/2000 |
| EP | 1056862 A1 | 12/2000 |
| EP | 1077257 A1 | 2/2001 |
| EP | 1112360 A1 | 7/2001 |
| EP | 0637339 B1 | 10/2001 |
| EP | 0316441 B1 | 12/2001 |
| EP | 0255378 B2 | 2/2002 |
| EP | 1232273 A2 | 8/2002 |
| EP | 1248850 A2 | 10/2002 |
| EP | 0729514 B1 | 2/2006 |
| EP | 1210446 B1 | 5/2006 |
| EP | 1242604 B1 | 5/2006 |
| EP | 0781849 B1 | 9/2007 |
| EP | 1019517 B2 | 5/2014 |
| WO | 9303161 A1 | 2/1993 |
| WO | 9534668 A3 | 2/1996 |
| WO | 0134820 A2 | 5/2001 |
| WO | WO2006/047495 A2 | 5/2006 |
| WO | WO 2012/155112 | * 11/2012 |
| WO | WO2012/155112 A1 | 11/2012 |

(Continued)

OTHER PUBLICATIONS

Thomas et al. 2001, The Plant Journal 25(4):419-425.*
Colliver et al. Plant Molecular Biology 35:509-522.*
Yibrah et al. 1993 Hereditas 118:273-280.*
Fourgoux-Nicol et al 1999, Plant Molecular Biology 40 :857-872.*
Liu et al: "Paralogous cyp51 genes in Fusarium graminearum mediate differential sensitivity to sterol demethylation inhibitors", Fungal Genetics and Biology, Oct. 2010, pp. 113-123, vol. 48, No. 2, 16, San Diego, CA, US.
Anonymous: "International Reinhardsbrunn Symposium on Modern Fungicides and Antifungal Compounds Scientific Program", Apr. 21, 2013, Retrieved from the Internet: URL:http://www.reinhardsbrunn-symposium.de/fileadmin/PDF/Scientific%20Program%2013_3_2012.pdf (retrieved on Mar. 11, 2014) Friedrichroda, DE.

(Continued)

*Primary Examiner* — Li Zheng
(74) *Attorney, Agent, or Firm* — Armstrong Teasdale LLP

(57) ABSTRACT

The present invention relates to dsRNA molecules for inhibiting the expression of CYP51 gene(s) from a fungal or oomycete phytopathogen and the use of such inhibitory dsRNA molecules for controlling phytopathogenic fungi and/or oomycetes. The present invention further relates to DNA sequences providing a transcriptional template for inhibitory dsRNA molecules or antisense RNA; and phytopathogen-tolerant transgenic plants with such DNA sequences.

24 Claims, 12 Drawing Sheets

Specification includes a Sequence Listing.

(56) References Cited

FOREIGN PATENT DOCUMENTS

WO    WO2013/043777 A1    3/2013

OTHER PUBLICATIONS

A. Koch et al: "Host-induced gene silencing of cytochrome P450 lanosterol C14 -demethylase-encoding genes confers strong resistance to *Fusarium* species", Proceedings of the National Academy of Sciences, Nov. 26, 2013; pp. 19324-19329, vol. 110, No. 48.

Koch et al., "The Antimicrobial Peptide Thanatin Reduces Fungal Infections in *Arabidopsis*" Journal of Phytopathology, 2012, pp. 606-610, vol. 160(10).

Vinay Panwar et al. "Endogenous silencing of Pucciniia triticina pathogenicity genes through in planta-expressed sequences leads to the suppression of rust diseases on wheat" The Plant Journal, Dec. 12, 2012, pp. 521-532, vol. 73, No. 3.

Rayko Becher et al. "Fungal cytochrome P450 sterol 14alpha-demethylase (CYP51) and azole resistance in plant and human pathogens" Applied Microbiology and Biotechnology, Jun. 12, 2012,pp. 825-840,vol. 95, No. 4, Springer, Berlin, DE.

C. Burger: "Virus-induced silencing of sterol biosynthetic genes: identificationof a *Nicotiana tabacum* L. obtusifoliol-14-demethylase (CYP51) by geneticmanipulation of the sterol biosynthetic pathway in *Nicotiana benthamiana* L.",Journal of Experimental Botany,May 13, 2003, pp. 1675-1683, vol. 54, No. 388.

Yoshida: "Lanosterol 14a-demethylase". In: Schenkman, H., Grein, K. (Eds.), Cytochromes P450; 1993. pp. 627-639 Springer-Verlag, Berlin.

Hamilton & Baulcombe, "A Species of Small Antisense RNA in Posttranscriptional Gene Silencing in Plants" Science, 1999, pp. 950-952, vol. 286.

Baulcombe, "RNA silencing in plants", Nature; 2004, 356-363, vol. 431.

Tinoco et al., "In vivo trans-specific gene silencing in fungal cells by in planta expression of a double-stranded RNA", BMC Biology. 2010; vol. 8, No. 27.

Becher et al.,"Development if a novel multiplex DNA microarray for Fusarium graminearum and analysis of azole fungicide responses" BMS Genomics, 2011 vol. 12, No. 52.

Jansen et al., "Infection patterns in barley and wheat spikes inoculated with wild-type and trichodiene synthase gene disrupted Fusarium graminearum", National Academy of Sciences of the USA; 2005; pp. 16892-16897; vol. 102, No. 46.

Nirenberg, "A simplified method for identifying *Fusarium* spp. occurring on wheat" CAN. J. Bot.; 1981, pp. 1599-1609; vol. 59.

Bechtold et al., "In planta Agrobacterium mediated gene transfer by infiltration of adult *Arabidopsis thaliana* plants", Comptes Rendus Acad. Sci. Paris, Life Sciences; 1993, pp. 1194-1199, vol. 316.

Chen et al., " A Rapid DNA Minipreparation Method Suitable for AFLP and Other PCR Applications", Plant Mol. Biol Rep, 1999, 53-57, vol. 17.

Livak et al., Analysis of Relative Gene Expression Data Using Real-Time Quantitative PCR and the 22-DDCT Method Methods, 2001, 402-408, vol. 25.

Fromm et al., "Inheritance and expression of chimeric genes in the progeny of transgenic maize plants", Biotechnology;1990, pp. 833-839, vol. 8, Nature Publishing Group.

International Preliminary Reporton Patentability for PCT/EP2014/ 064686 dated Jan. 21, 2016, 13 pgs.

International Search Report for Application No. PCT/EP2014/ 064686 dated Nov. 14, 2014, 7 pgs.

\* cited by examiner

RNAI FOR THE CONTROL OF PHYTOPATHOGENIC FUNGI AND OOMYCETES BY INHIBITING THE EXPRESSION OF CYP51 GENES

FIELD OF THE INVENTION

The present invention relates to double-stranded RNA (dsRNA)-mediated gene silencing of one or more than one CYP51 gene from a fungal or oomycete phytopathogen. Accordingly, the present invention relates to dsRNA molecules for inhibiting the expression of the CYP51 gene(s) and the use of such inhibitory dsRNA molecules for controlling phytopathogenic fungi and/or oomycetes; DNA sequences providing a transcriptional template for inhibitory dsRNA molecules or antisense RNA; and phytopathogen-tolerant transgenic plants comprising such DNA sequences.

BACKGROUND OF THE INVENTION

Plant diseases caused by phytopathogenic fungi and oomycetes are a serious risk in the culturing of plants. Diseases of cereal crops such as Fusarium head blight and root rot caused by phytopathogenic fungi of the genus Fusarium exert great economic and agronomic impact on global grain production and the grain industry. The damages caused by phytopathogenic fungi and oomycetes impair quality and yield of the agricultural products up to total crop failure, and thus result in significant economic losses. In addition, food safety can be compromised by contamination of agricultural products with mycotoxins, which are produced by phytopathogenic fungi during plant infestation and represent a serious threat to human and animal health. The risk of devastating losses due to phytopathogenic fungi and oomycetes is particularly high in monocultures which currently represent the predominant method of agricultural crop plant production.

Currently, the major strategies in management of phytopathogenic fungi and oomycetes include the widely used application of fungicides, resistance breeding strategies, biological control and genetic engineering. The latter strategy relies on the use of transgenes such as chitinase, defensins, polygalacturonase, and the use of mycotoxin detoxifying enzymes. However, the use of such antifungal traits has so far not provided convincing practical solutions in terms of efficiency and reliability under agronomical practice.

Fungicides, such as systemic DMIs (demethylation inhibitors), are currently essential for controlling plant diseases such as fusarioses to reach the attainable production level of modern high-yield cultivars. DMI fungicides, such as tebuconazole, triadimefon, and prochloraz, inhibit ergosterol biosynthesis by binding to cytochrome P450 lanosterol C-14 α-demethylase (CYP51) which results in disturbance of the fungal membrane integrity (Yoshida: Lanosterol 14α-demethylase. In: Schenkman, H., Grein, K. (Eds.), Cytochromes P450. Springer-Verlag, Berlin, 1993. pages 627-639). However, the heavy reliance on DMI fungicides since their discovery in the mid-1970s has led to the emergence of many DMI-resistant phytopathogen strains over the last few years. For these reasons, control of plant diseases caused by phytopathogenic fungi and oomycetes continues to be a challenge.

RNA interference, also known as "RNAi", has emerged as a genetic tool that accelerated research in plant biotechnology. RNAi is a conserved integral part of the gene regulation processes present in all eukaryotes. For RNAi in plants, the alternative term "post-transcriptional gene silencing" (PTGS) has been used. PTGS starts with the processing or cleaving of a precursor double-stranded RNA into short, about 20-25 ribonucleotides long, single- or double-stranded interfering RNA (siRNA) or micro RNA (miRNA) (Hamilton & Baulcombe, Science 286:950-952. 1999) by an RNaseIII-like enzyme called Dicer (Baulcombe, Nature 431: 356-363. 2004). The siRNAs or miRNAs are incorporated into an RNA-induced silencing complex (RISC) which recognizes complementary messenger RNA (mRNA) molecules and degrades them, thus resulting in substantially decreased levels of protein translation and effectively turning off the corresponding gene.

In planta expression of double-stranded RNAs was recently described to induce host plant-induce gene silencing (HIGS) in fungal cells. In tobacco, expression of a GUS (β-glucuronidase) gene-interfering cassette was reported to specifically reduce transcript levels in a GUS-expressing strain of Fusarium verticillioides during plant colonization (Tinoco et al., BMC Biol. 31(8):27. 2011). Nowara et al. (Plant Cell 22:3130-41. 2010) prepared barley expressing a double-stranded RNA targeting the fungal effector gene Avra10 and reported reduced numbers of functional haustoria inside leave epidermal cells. Agrobacterium tumefaciens-mediated transient silencing of the Puccinia triticina (leaf rust) pathogenicity genes mitogen-activated protein kinase 1 (PtMAPK1), cyclophilin (PtCYC1), and calcineurin B (PtCNB) was described to partly suppress the growth of P. triticina, P. graminis and P. stniformis in wheat (Panwar et al., Plant J 73:521-32. 2013).

It was an object of the present invention to provide a further RNAi-based approach against fungal and oomycete phytopathogens, and in particular to provide a method and means for controlling such phytopathogens in the agronomical practice.

SUMMARY OF THE INVENTION

The inventors have found that RNAi targeting at least one CYP51 gene of a phytopathogenic fungus or oomycete is effective in controlling such phytopathogens. Accordingly, plant protection products and transgenic plants based on said novel approach can be useful in crop plant production.

The present invention provides a dsRNA molecule capable of inhibiting the expression of at least one CYP51 gene from a fungal or oomycete phytopathogen. The dsRNA molecule of the invention comprises:
  a sense sequence being at least 70% identical to at least 20 contiguous nucleotides of the coding sequence of said at least one CYP51 gene, and an antisense sequence being substantially complementary to said sense sequence,
  wherein the arrangement of the sequences within the dsRNA molecule allows hybridization of said sense sequence and said corresponding antisense sequence.

The present invention further provides a DNA sequence or a multitude of DNA sequences providing a transcriptional template of at least the antisense sequence(s) of the dsRNA molecule of the invention.

The present invention further provides methods for preparing a transgenic plant comprising the introduction of such DNA sequence(s) of the invention into the plant.

Also provided are transgenic plants comprising the DNA sequence(s) of the invention as well as methods for controlling a fungal and/or oomycete phytopathogen, wherein the methods comprise the cultivation a transgenic plant of the invention to allow the generation of RNA comprising the antisense sequence(s) of the dsRNA molecules of the invention by the plant.

The present invention further provides compositions for controlling a fungal and/or oomycete phytopathogen comprising the dsRNA molecule of the invention and a plant-compatible carrier as well as methods for controlling a fungal and/or oomycete phytopathogen, wherein a plant infested by or at risk of being infested by said phytopathogen and/or the vicinity of said plant is contacted with such composition of the invention.

Figure 1:
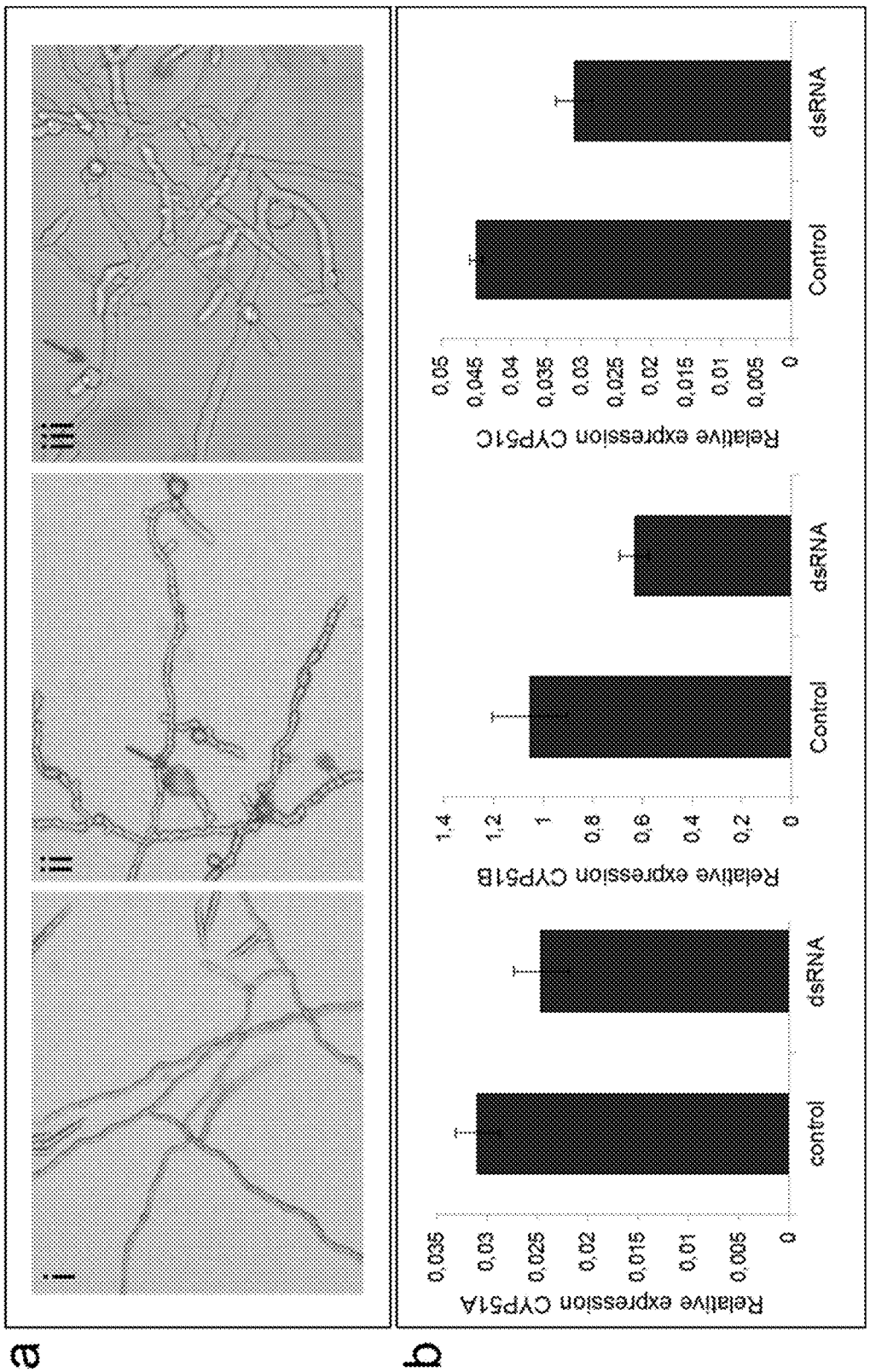
FIG. 1: Morphology of *Fusarium graminearum* (Fg) macroconidia grown in axenic culture following treatment with CYP3RNA or tebuconazole. (a) One hundred Fg macroconidia were suspended in 100 μl of liquid SNA medium and treated with (i) 1.5 μg CYP3RNA dsRNA, (ii) 5 mg/I tebuconazole and (iii) mock (50× annealing buffer) at room temperature. Pictures were taken 72 h post treatment. The arrows point to swelling and ballooning hyphal tips. (b) Quantification of fungal CYP51A, CYP51B and CYP51C transcripts by quantitative RT-PCR using the same mock- and CYP3RNA-treated samples as in (a). The data was normalized to β-tubulin.
Figure 2:
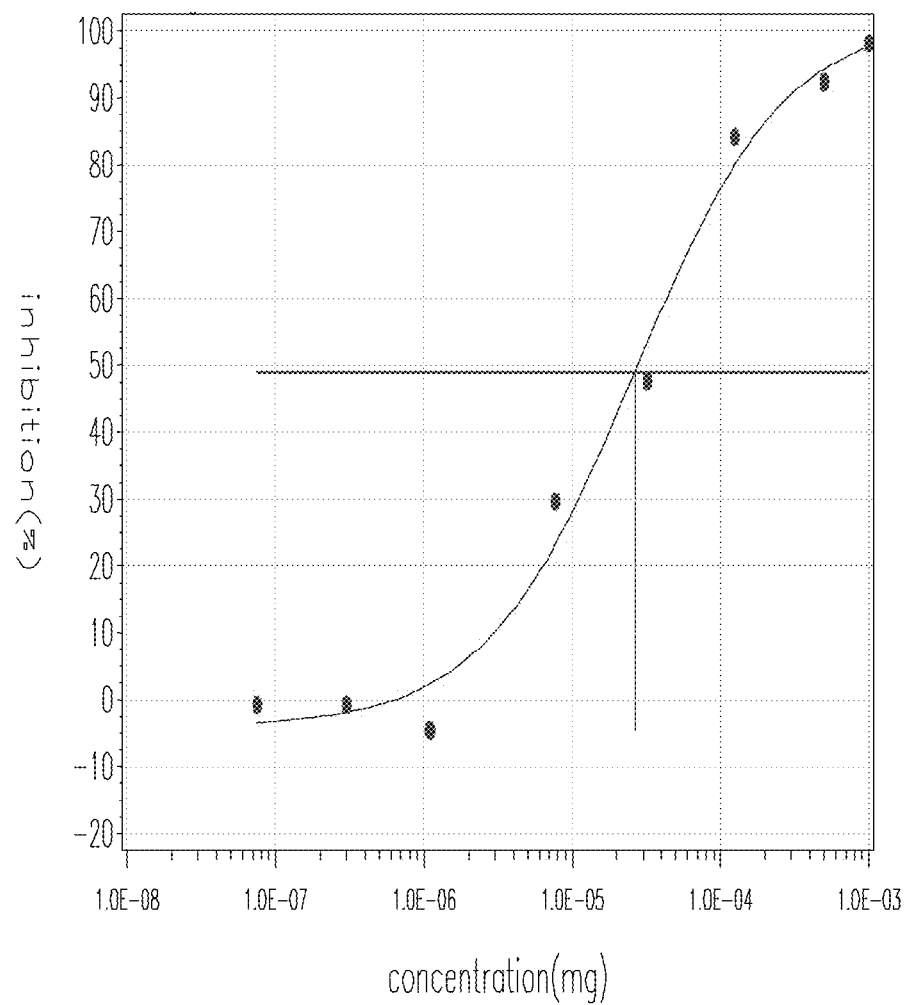
FIG. 2: Inhibition of the growth of Fg macroconidia by CYP3RNA. One hundred Fg macroconidia were suspended in 100 μl of liquid SNA medium and treated with different concentrations of CYP3RNA dsRNA in the range of from 75 μg to 1 μg dsRNA. Densities of Fg macroconidia cultures were measured at beginning of the treatment and 72 h post treatment.

FIG. 3: Infestation symptoms on *Arabidopsis* leaves following inoculation with Fg. (a) Detached leaves of 5-week-old plants were treated with $5\times10^4$ Fg macroconidia $ml^{-1}$ and evaluated for necrotic lesions at 3 days post inoculation (dpi). (i) Col-0 wt, (ii) Col-0 empty vector (ev) control, (iii) Col-0 expressing CYP3RNA (L8 Col-0-CYP3RNA), and (iv) Col-0 mock-inoculated (Tween water). (b) Quantification of Fg-infested leaf area at 3 dpi; typical infestation symptoms are expressed as a percent of the total leaf area. Bars represent mean values±SDs of three independent experiments, each using 20 leaves collected from 15 different plants of each transgenic plant line, as well as Col-0 wt and Col-0 ev plants. The reduction in infestation symptoms on CYP3RNA-expressing leaves as compared to the Col-0 wt and Col-0 ev controls was statistically significant (***$p<0.0001$; Student's t-test). (c) Fg-inoculated *Arabidopsis* leaves at 5 dpi. (i) The Col-0 ev leaf is heavily infested with Fg (ii) Col-0 expressing CYP3RNA does not show infestation symptoms, although fungal mycelia are able to grow in the agar surrounding the intact, symptomless leaf.

FIG. 4: Abundance of CYP51 gene transcripts and siRNAs in Fg-inoculated *Arabidopsis* leaves. (α-c) Gene-specific analysis of CYP51 transcripts at 3 dpi by qRT-PCR using fungal β-tubulin as the reference gene. (a) CYP51A, (b) CYP51B and (c) CYP51C. cDNA was generated from total RNA isolated from Fg-inoculated leaves collected during the detached leaf assay. Bars represent mean values±SDs of three independent sample collections. The reduction in CYP51 gene expression in the Fg-inoculated Col-0-CYP3RNA leaves compared to the ev control was statistically significant ($p<0.001$, *$p<0.0001$; Student's t-test). (d). Detection of low molecular weight siRNA complementary to the CYP51 genes in pooled leaf tissue from uninfested and Fg-infested *Arabidopsis* plants at 3 dpi. Northern blot analysis using $^{32}$P-labelled CYP3RNA was followed by autoradiography. No signal was detected in the control samples from Col-0 and Col-0-ev plants. Ethidium bromide-stained rRNA in the bottom panel served as the loading control.

FIGS. 5-9: Fragment combination strategy (stacking) in pGEM-T-CYP3 (FIG. 5) for generating CYP3RNA, a construct designed from partial sequences of CYP51A (SEQ ID NO:4), CYP51B (SEQ ID NO:5) and CYP51C (SEQ ID NO:6) to silence all three CYP51 genes. (FIG. 6) p7U10-RNAi, a binary vector with inverted repeat CaMV35S promoters. (FIG. 7) p7U10-CYP3RNAi, generated by replacing the GUS-fragment in p7U10-RNAi by the CYP3RNA fragment (CYP51B-CYP51A-CYP51C) using HindIII/XmaI restriction enzymes. (FIG. 8) p7i-Ubi-RNAi2, a binary vector with inverted repeat CaMV35S promoters. (FIG. 9) p7i-UBi-CYP3RNAi, generated by replacing the GUS-fragment in p7i-Ubi-RNAi2 by a CYP51ABC fragment (CYP51A-CYP51 BCYP51C) using HindIII/XmaI restriction enzymes.

FIG. 10: Leaves of transgenic barley expressing CYP51ABC (L2-L9, L14, L42), of a wildtype control plant (cv. Golden Promise; GP) and of a transgenic control plant comprising only the transfection vector (empty vector; ev) 7 days after inoculation (7 dpi) with Fg as described in Example 4.

FIG. 11: Abundance of CYP51 gene transcripts in Fg-inoculated barley leaves. (α-c) Gene-specific analysis of CYP51 transcripts at 7 dpi by qRT-PCR using fungal β-tubulin as the reference gene. (a) CYP51A, (b) CYP51B and (c) CYP51C. cDNA was generated from total RNA isolated from Fg-inoculated leaves collected during the detached leaf assay.

FIG. 12: Inhibition of fungal growth by spraying barley leaves with CYP3RNA dsRNA. Detached barley leaves were sprayed area-covering (A) or systemically (B) with CYP3RNA dsRNA ("RNA"), TE-buffer only ("control") or GFP-dsRNA ("GFP"), respectively. 48 h after spraying the leaves were drop-inoculated with FIG. 6 days after infection, the infection symptoms were recorded (A, B) and the relative amount of fungal genomic R-tubulin DNA in area-covering-sprayed (C) or systemically-sprayed (D) leaves, respectively, was measured using quantitative PCR (qPCR). Graphs C and D show the relative amount of fungal genomic R-tubulin DNA normalized to the amount of plant genomic ubiquitin DNA.

DETAILED DESCRIPTION OF INVENTION

1) Definitions

The term "fungal or oomycete phytopathogen", as used herein, refers to a fungus or oomycete that is parasitic on a plant host.

Phytopathogenic fungi include fungi of the phyla Ascomycota and Basidiomycota. The asexual reproduction stage (anamorph) of such fungus may be known under a different name than its sexual reproduction stage (teleomorph). For example, *Fusarium graminearum* refers to the anamorph and *Gibberella zeae* to the teleomorph of the same fungal species. For the purpose of the present invention, the names of the Ascomycota and Basidiomycota used herein are meant to refer the fungal species per se rather than to a particular reproduction stage thereof.

CYP51 genes are genes encoding a cytochrome P450 sterol 14α-demethylase (CYP51) and homologues thereof.

A fungal or oomycete phytopathogen can have more than one CYP51 gene. The different CYP51 genes can be grouped into clades by molecular phylogenic analysis as described, e.g., by Becher et al. (BMS Genomics 12: 52. 2011). Three clades of CYP51 have been identified for fungi of the subphylum Pezizomycotina: CYP51A, CYP51B and CYP51C (supra). CYP51 genes, CYP51 proteins and corresponding coding sequences of phytopathogenic fungi and oomycetes are known in the art and can be identified by homology searches, e.g. based on FGSG_04092.3, FGSG_01000.3 and FGSG_11024.3, by sequence analyses as described, e.g., by Becher et al. (BMS Genomics 12: 52. 2011; cf. section on Bioinformatics), and from sequence databases such as the Fungal Cytochrome P450 Database www.p450.riceblast.snu.ac.kr.

The term "dsRNA molecule", as used herein for designating a subject matter of the invention, refers to a molecule comprising one, two or more polyribonucleotide strands capable of forming at least one region of double stranded RNA. Thus, the term "dsRNA molecule of the invention" includes molecules, wherein only part of the RNA, e.g. at least 70%, at least 80% or at least 90%, or all of the RNA is present as double stranded RNA. For example, the term "dsRNA molecule" includes molecules consisting of one, two or more polyribonucleotide strands. Also included by the term are molecules additionally comprising further chemical groups, for example groups stabilizing the regions of double stranded RNA as described herein.

The effect of the dsRNA molecules of the invention is assumed to be due to RNA interference. The terms "RNAi" and "RNA interference", used herein, refer to a process of sequence-specific post-transcriptional gene silencing mediated by double-stranded RNA. In the RNAi process, a double-stranded RNA is processed into relatively small fragments, typically 20-25 nucleotides in length, which become part of an RNA-induced silencing complex (RISC) which binds to and cleaves complementary mRNA and thus prevents the mRNA from being used as a template for translation.

The term "antisense interference" also refers to a process of sequence-specific post-transcriptional gene silencing. In antisense interference, a single-stranded antisense RNA (antisense-ssRNA) that is substantially complementary to at least a part of a target gene causes inhibition of the target gene expression. It is assumed that in this process double-stranded RNA is formed by hybridization of the antisense ssRNA hybridizes with complementary mRNA and inhibits the target gene expression using the RNAi mechanism.

The expression "at least part of", when used with reference to a sequence, e.g. with reference to the coding sequence of a CYP51 gene, refers to at least 20 contiguous nucleotides of said sequence. For example, "at least part of" refers to at least 25, at least 50, at least 100, at least 150 and preferably at least 200 contiguous nucleotides of the sequence.

A "high degree of identity", as used herein to define the degree of sequence identity of a sense sequence to at least part of the coding sequence of a CYP51 gene or any one of SEQ ID NOs: 1-6 and 8-13, includes an identity of at least 70%, at least 75%, at least 80%, at least 85%, at least 90%, preferably at least 95% or at least 98%, and most preferably at least 99% or 100%.

With regard to sequence identity between RNA and DNA sequences, a uracil within a RNA sequence is considered "identical" to a thymine within a DNA sequence. Methods and tools such as computer programs for calculating sequence identity are well known in the art. For example, the degree of identity between nucleotide sequences can be determined using a Basic Local Alignment Search Tool (BLAST) such as the BLAST Similarity Search (gapped alignment) available on the website of the Broad Institute www.broadinstitute.org.

An "antisense sequence" as comprised by the dsRNA molecules of the present invention is an RNA sequence that is substantially complementary to the corresponding sense sequence.

"Complementary" polynucleotides are those capable of base pairing according to the Watson-Crick complementarity rules. Specifically, base pairs will form between purines and pyrimidines including guanine paired with cytosine (G:C) and adenine paired with either thymine (A:T) in case of DNA, or adenine paired with uracil (A:U) in the case of RNA. It is understood that two polynucleotides may hybridize to each other even if they are not completely complementary to each other, provided that each has at least one region that is substantially complementary to the other.

The term "substantially complementary", as used herein e.g. for characterizing the antisense sequences of the dsRNA molecule of the invention, means that two nucleotide sequences are complementary over at least at 80% of their nucleotides. Preferably, the two nucleotide sequences are complementary over at least at 85%, at least 90%, more preferably at least 95%, at least 96%, at least 97%, at least 98%, and most preferably at least 99% of their nucleotides up to their full length. Alternatively, "substantially complementary" can refer to two nucleic acid sequences which can hybridize under stringent conditions.

The term "hybridization", as used herein, includes any process by which a polynucleotide strand joins with a complementary strand through base pairing. (Coombs: Dictionary of Biotechnology, Stockton Press, New York, 1994). Hybridization and the strength of hybridization (i.e., the strength of the association between the two complementary strands) is impacted by factors such as the degree of complementarity between the strands, the stringency of the conditions involved, the melting temperature of the formed double strand, and the G:C ratio within the strands. The melting temperature (Tm) is the temperature at which a population of double-stranded polynucleotides becomes half dissociated into single strands. Tm can be calculated using equations well known in the art. An estimate for the Tm value of a polynucleotide in an aqueous 1 M NaCl solution is given by the equation: $Tm=81.5+0.41(\% G+C)$ (cf., e.g., Anderson and Young: Quantitative Filter Hybridization, in Nucleic Acid Hybridization, 1985). Stringent conditions are known to those skilled in the art (cf., e.g., Current Protocols in Molecular Biology, John Wiley & Sons, N.Y., 6.3.1-6.3.6, 1989). In particular, the term "stringent conditions", as used herein, refers to hybridization to filter-bound nucleic acid in 6× sodium chloride/sodium citrate (SSC) at about 45° C. followed by one or more washes in 0.2×SSC/0.1% SDS (sodium dodecyl sulfate) at about 50-65° C.

The term "expression", as used herein with respect to a gene sequence, refers to the translation of the coding sequence to a polypeptide. Inhibition of gene expression can become detectable on the level of mRNA, on the level of polypeptide or both. Methods for assessing changes in the mRNA level or the protein level of a gene are well-known in the art. For example, the change in the mRNA level of a gene can be assessed by quantitative real-time PCR (qRT-PCR) or Northern Blot.

"Controlling" a phytopathogenic fungus or oomycete, as used herein, includes measures for preventing the infestation of a plant with said pathogen as well as measures for combatting or curing the pathogen infestation of a plant. The term "combatting" refers to the reduction of the pathogen infestation. The term "curing" refers to the eradication of the pathogen infestation.

A "plant-compatible" carrier, as used herein, is a compound or a mixture of compounds that, under the conditions of its use, does not exert unacceptable phytotoxic activity to the treated plant.

The term "plant" is used herein to designate a whole plant at any stage of development as well as a part or derivative thereof, and thus includes, for instance, a plant cell, a plant cell population, a plant tissue (e.g. a meristematic tissue, callus tissue), a plant organ (e.g. stem, leaf, root, ovule, stamen), a reproductive form or reproductive part of a plant (e.g. a seed, tuber, cutting, gametophyte, sporophyte, pollen, microspore, embryo). A plant cell or plant cell population can be isolated (e.g. in suspension culture) or comprised in a plant tissue, plant organ or whole plant of any developmental stage.

A "transgenic" plant is a whole plant or part thereof that has been altered using recombinant DNA technology to contain a nucleic acid sequence which would otherwise not be present in said plant or which would be expressed to a considerably lower extent.

The term "transgenic plant" also includes the transgenic progeny of a transgenic plant. A transgenic plant of the present invention may result from crossing a transgenic plant of the invention with a non-transgenic plant or with another transgenic plant of the invention or with a transgenic plant having a different transgene. In particular, the term "transgenic plant" also comprises true breeding transgenic plants which are obtained by repeated inbreeding steps.

A "transcriptional template" of an RNA sequence is a DNA sequence that can serve as a template for the generation of the RNA by enzymatic transcription with an RNA polymerase.

The term "promoter", when used herein in the context of the nucleic acid sequence(s) of the invention, refers to the singular as well as to the plural, unless explicitly stated otherwise. A "promoter", as used herein, is a DNA sequence which, when ligated to a DNA sequence of interest, is capable of controlling the transcription of said DNA sequence into RNA. A promoter is typically located 5' (e.g., upstream) of the DNA sequence of interest whose transcription into mRNA it controls (e.g., proximal to the transcriptional start site), and provides a site for specific binding by RNA polymerase and other transcription factors for initiation of transcription. A promoter can be a constitutive promoter or a regulated promoter.

A "regulated promote" is a promoter that drives transcription not constitutively but in a temporally and/or spatially restricted manner. A promoter is regulated if the amount of RNA produced under the control of the activated promoter is at least 30%, 40%, 50%, 60%, 70%, 80%, 90%, 100%, 200% or 300% higher than the amount of RNA produced in parts of the plant or at periods of time, where the promoter is not activated. Regulated promoters include inducible promoters, tissue-specific promoters and development-specific promoters. Tissue-specific or development-specific promoters facilitate transcription of a sequence of interest in specific tissues, organs or cell types, or at specific different developmental stages while leaving the rest of the organism unmodified. In the case of plants, such promoters might specifically influence expression of genes in the roots, inflorescence, cereal ears, fruits, or seeds, or during the vegetative, flowering, or seed-setting stage. Inducible promoters facilitate transcription of a sequence of interest in the presence or absence of particular chemical compounds (e.g. an alcohol, tetracycline, a steroid, or a metal) or depending on particular physical conditions (e.g. the presence or absence of light, low or high temperatures).

The term "phytopathogen-tolerant" is used herein to designate a transgenic plant of the invention capable of reducing or preventing the growth and/or propagation of the phytopathogen. The tolerance to the phytopathogen can be transient, i.e. present only for a limited period of time, for example due to a transient expression of the antisense-ssRNA or the dsRNA molecule of the invention. A plant that is "tolerant" to a phytopathogen is infested less severely and/or less frequently by the phytopathogen. Severity of the fungal or oomycetes infestation can be determined based on the disease symptoms observed after the plant was inoculated with or attacked by the phytopathogen. The disease symptoms depend on the nature (species, variant) of the phytopathogen and of the plant. Symptoms of fungal or oomycete infestations of plants include, but are not limited to, premature bleaching of cereal ears and/or leaves; necrotic lesions on the exterior surface of the florets and glume; kernel atrophy; awn deformation; discoloration of kernels and/or spikelets; visible pathogen growth on leaves, stem, and/or cereal ears.

2) Particular Embodiments of the Invention

The present invention refers to dsRNA molecules and antisense-ssRNA capable of inhibiting the expression of at least one CYP51 gene of a fungal or oomycete phytopathogen.

Further, the dsRNA molecules and antisense-ssRNA of the present invention are capable of reducing or preventing the growth and/or propagation of fungal or oomycete phytopathogens. Specifically, dsRNA molecules and antisense-ssRNA of the present invention are capable of reducing or eradicating the infestation of a plant by fungal or oomycete phytopathogens, wherein said plant contains and/or is treated with said dsRNA molecules or antisense-ssRNA.

The dsRNA molecules and antisense-ssRNA of the invention are useful for controlling phytopathogenic fungi and oomycetes including, but not limited to, *Albugo* spp. (white rust) on ornamentals, vegetables (e.g. *A. candida*) and sunflowers (e.g. *A. tragopogonis*); *Alternaria* spp. (*Alternaria* leaf spot) on vegetables, rape (*A. brassicola* or *brassicae*), sugar beets (*A. tenuis*), fruits, rice, soybeans, potatoes (e.g. *A. solani* or *A. alternata*), tomatoes (e.g. *A. solani* or *A. alternata*) and wheat; *Aphanomyces* spp. on sugar beets and vegetables; *Ascochyta* spp. on cereals and vegetables, e.g. *A. tritici* (anthracnose) on wheat and *A. hordei* on barley; *Bipolaris* and *Drechslera* spp. (teleomorph: *Cochliobolus* spp.), e.g. Southern leaf blight (*D. maydis*) or Northern leaf blight (*B. zeicola*) on corn, e.g. spot blotch (*B. sorokiniana*) on cereals and e.g. *B. oryzae* on rice and turfs; *Blumeria* (formerly *Erysiphe*) *graminis* (powdery mildew) on cereals (e.g. on wheat or barley); *Botrytis cinerea* (teleomorph: *Botryotinia fuckeliana*: grey mold) on fruits and berries (e.g. strawberries), vegetables (e.g. lettuce, carrots, celery and cabbages), rape, flowers, vines, forestry plants and wheat; *Bremialactucae* (downy mildew) on lettuce; *Ceratocystis* (syn. *Ophiostoma*) spp. (rot or wilt) on broad-leaved trees and evergreens, e.g. *C. ulmi* (Dutch elm disease) on elms; *Cercospora* spp. (*Cercospora* leaf spots) on corn (e.g. Gray leaf spot: *C. zeae-maydis*), rice, sugar beets (e.g. *C. beticola*), sugar cane, vegetables, coffee, soybeans (e.g. *C. sofina* or *C. kikuchii*) and rice; *Cladosporium* spp. on tomatoes (e.g. *C. fulvum*: leaf mold) and cereals, e.g. *C.*

*herbarum* (black ear) on wheat; *Claviceps purpurea* (ergot) on cereals; *Cochliobolus* (anamorph: *Helminthosporium* of *Bipolaris*) spp. (leaf spots) on corn (*C. carbonum*), cereals (e.g. *C. sativus*, anamorph: *B. sorokiniana*) and rice (e.g. *C. miyabeanus*, anamorph: *H. oryzae*); *Colletotrichum* (teleomorph: *Glomerella*) spp. (anthracnose) on cotton (e.g. *C. gossypii*), corn (e.g. *C. graminicola*: Anthracnose stalk rot), soft fruits, potatoes (e.g. *C. coccodes*: black dot), beans (e.g. *C. lindemuthianum*) and soybeans (e.g. *C. truncatum* or *C. gloeosporioides*); *Corticium* spp., e.g. *C. sasaki* (sheath blight) on rice; *Corynespora casslicola* (leaf spots) on soybeans and ornamentals; *Cycloconium* spp., e.g. *C. oleaginum* on olive trees; *Cylindrocarpon* spp. (e.g. fruit tree canker or young vine decline, teleomorph: *Nectria* or *Neonectria* spp.) on fruit trees, vines (e.g. *C. liriodendri*, teleomorph: *Neonectria liriodendri*: Black Foot Disease) and ornamentals; *Dematophora* (teleomorph: *Rosellinia*) necatrix (root and stem rot) on soybeans; *Diaporthe* spp., e.g. *D. phaseolorum* (damping off) on soybeans; *Drechslera* (syn. *Helminthosporium*, teleomorph: *Pyrenophora*) spp. on corn, cereals, such as barley (e.g. *D. teres*, net blotch) and wheat (e.g. *D. tritici-repentis*: tan spot), rice and turf; Esca (dieback, apoplexy) on vines, caused by *Formitiporia* (syn. *Phellinus*) *punctata*, *F. mediterranea*, *Phaeomoniella chlamydospora* (earlier *Phaeoacremonium chlamydosporum*), *Phaeoacremonium aleophilum* and/or *Botryosphaeria obtusa*; *Elsinoe* spp. on pome fruits (*E. pyri*), soft fruits (*E. veneta*: anthracnose) and vines (*E. ampelina*: anthracnose); *Entyloma oryzae* (leaf smut) on rice; *Epicoccum* spp. (black mold) on wheat; *Elysiphe* spp. (powdery mildew) on sugar beets (*E. betae*), vegetables (e.g. *E. pisi*), such as cucurbits (e.g. *E. cichoracearum*), cabbages, rape (e.g. *E. cruciferarum*); *Eutypa lata* (*Eutypa* canker or dieback, anamorph: *Cytosporina lata*, syn. *Libertella blepharis*) on fruit trees, vines and ornamental woods; *Exserohilum* (syn. *Helminthosporium*) spp. on corn (e.g. *E. turcicum*); *Fusarium* (teleomorph: *Gibberella*) spp. (wilt, root or stem rot) on various plants, such as *F. graminearum* or *F. culmorum* (root rot, scab or head blight) on cereals (e.g. wheat or barley), *F. oxysporum* on tomatoes, *F. solani* (f. sp. *glycines* now syn. *F. virguliforme*) and *F. tucumaniae* and *F. brasiliense* each causing sudden death syndrome on soybeans, and *F. vertialioides* on corn; *Gaeumannomyces graminis* (take-all) on cereals (e.g. wheat or barley) and corn; *Gibberella* spp. on cereals (e.g. *G. zeae*) and rice (e.g. *G. fujikuroi*: Bakanae disease); *Glomerella cingulata* on vines, pome fruits and other plants and *G. gossypii* on cotton; Grainstaining complex on rice; *Guignardia bidwellii* (black rot) on vines; *Gymnosporangium* spp. on rosaceous plants and junipers, e.g. *G. sabinae* (rust) on pears; *Helminthosporium* spp. (syn. *Drechslera*, teleomorph: *Cochliobolus*) on corn, cereals and rice; *Hemileia* spp., e.g. *H. vastatrix* (coffee leaf rust) on coffee; *Isariopsis clavispora* (syn. *Cladosporium vitis*) on vines; *Macrophomina phaseolina* (syn. *phaseoli*) (root and stem rot) on soybeans and cotton; *Microdochium* (syn. *Fusarium*) *nivale* (pink snow mold) on cereals (e.g. wheat or barley); *Microsphaera diffusa* (powdery mildew) on soybeans; *Monilinia* spp., e.g. *M. taxa*, *M. fructicola* and *M. fructigena* (bloom and twig blight, brown rot) on stone fruits and other rosaceous plants; *Mycosphaerella* spp. on cereals, bananas, soft fruits and ground nuts, such as e.g. *M. graminicola* (anamorph: *Septoria tritici*, *Septoria* blotch) on wheat or *M. fijiensis* (black Sigatoka disease) on bananas; *Peronospora* spp. (downy mildew) on cabbage (e.g. *P. brassicae*), rape (*P. parasilica*), onions (e.g. *P. destructor*), tobacco (*P. tabacina*) and soybeans (e.g. *P. manshurica*); *Phakopsora pachyrhizi* and *P. meibomiae* (soybean rust) on soybeans; *Phialophora* spp. e.g. on vines (e.g. *P. tracheiphila* and *P. tetraspora*) and soybeans (e.g. *P. gregata*: stem rot); *Phoma lingam* (root and stem rot) on rape and cabbage and *P. betae* (root rot, leaf spot and damping-off) on sugar beets; *Phomopsis* spp. on sunflowers, vines (e.g. *P. viticola*: can and leaf spot) and soybeans (e.g. stem rot: *P. phaseoli*, teleomorph: *Diaporthe phaseolorum*); *Physoderma maydis* (brown spots) on corn; *Phytophthora* spp. (wilt, root, leaf, fruit and stem root) on various plants, such as paprika and cucurbits (e.g. *P. capsici*), soybeans (e.g. *P. megasperma*, syn. *P. sojae*), potatoes and tomatoes (e.g. *P. infestans*: late blight) and broad-leaved trees (e.g. *P. ramorum*: sudden oak death); *Plasmodiophora brassicae* (club root) on cabbage, rape, radish and other plants; *Plasmopara* spp., e.g. *P. viticola* (grapevine downy mildew) on vines and *P. halstedii* on sunflowers; *Podosphaera* spp. (powdery mildew) on rosaceous plants, hop, pome and soft fruits, e.g. *P. leucotricha* on apples; *Polymyxa* spp., e.g. on cereals, such as barley and wheat (*P. graminis*) and sugar beets (*P. betae*) and thereby transmitted viral diseases; *Pseudocercosporella herpotrichoides* (eyespot, teleomorph: *Tapesia yallundae*) on cereals, e.g. wheat or barley; *Pseudoperonospora* (downy mildew) on various plants, e.g. *P. cubensis* on cucurbits or *P. humili* on hop; *Pseudopezicula tracheiphila* (red fire disease or 'rotbrenner', anamorph: *Phialophora*) on vines; *Puccinia* spp. (rusts) on various plants, e.g. *P. triticina* (brown or leaf rust), *P. striiformis* (stripe or yellow rust), *P. hordei* (dwarf rust), *P. graminis* (stem or black rust) or *P. recondita* (brown or leaf rust) on cereals, such as e.g. wheat, barley or rye, *P. kuehnil* (orange rust) on sugar cane and *P. asparagi* on asparagus; *Pyrenophora* (anamorph: *Drechslera*) *tritici-repentis* (tan spot) on wheat or *P. teres* (net blotch) on barley; *Pyriculana* spp., e.g. *P. oryzae* (teleomorph: *Magnaporthe grisea*, rice blast) on rice and *P. grisea* on turf and cereals; *Pythium* spp. (damping-off) on turf, rice, corn, wheat, cotton, rape, sunflowers, soybeans, sugar beets, vegetables and various other plants (e.g. *P. ultimum* or *P. aphanidermatum*); *Ramularia* spp., e.g. *R. collo-cygni*(*Ramularia* leaf spots, Physiological leaf spots) on barley and *R. beticola* on sugar beets; *Rhizoctonia* spp. on cotton, rice, potatoes, turf, corn, rape, potatoes, sugar beets, vegetables and various other plants, e.g. *R. solani* (root and stem rot) on soybeans, *R. solani* (sheath blight) on rice or *R. cerealis* (*Rhizoctonia* spring blight) on wheat or barley; *Rhizopus stolonifer* (black mold, soft rot) on strawberries, carrots, cabbage, vines and tomatoes; *Rhynchosporium secalis* (scald) on barley, rye and triticale; *Sarocladium oryzae* and *S. attenuatum* (sheath rot) on rice; *Sclerotinia* spp. (stem rot or white mold) on vegetables and field crops, such as rape, sunflowers (e.g. *S. sclerotiorum*) and soybeans (e.g. *S. rolfsii* or *S. sclerotiorum*); *Septoria* spp. on various plants, e.g. *S. glycines* (brown spot) on soybeans, *S. tritici* (*Septoria* blotch) on wheat and S. (syn. *Stagonospora*) *nodorum* (*Stagonospora* blotch) on cereals; *Uncinula* (syn. *Erysiphe*) *necator* (powdery mildew, anamorph: *Oidium tuckeri*) on vines; *Setospaeria* spp. (leaf blight) on corn (e.g. *S. turcicum*, syn. *Helminthosporium turcicum*) and turf; *Sphacelotheca* spp. (smut) on corn, (e.g. *S. reiliana*: head smut), sorghum and sugar cane; *Sphaerotheca fuliginea* (powdery mildew) on cucurbits; *Spongospora subterranea* (powdery scab) on potatoes and thereby transmitted viral diseases; *Stagonospora* spp. on cereals, e.g. *S. nodorum* (*Stagonospora* blotch, teleomorph: *Leptosphaeria* [syn. *Phaeosphaeria*] *nodorum*) on wheat; *Synchytrium endobioticum* on potatoes (potato wart disease); *Taphrina* spp., e.g. *T. deformans* (leaf curl disease) on peaches and *T. Pruni* (plum pocket) on plums; *Thielaviopsis* spp. (black root rot)

on tobacco, pome fruits, vegetables, soybeans and cotton, e.g. *T. basicola* (syn. *Chalara elegans*); *Tilletia* spp. (common bunt or stinking smut) on cereals, such as e.g. *T. tritici* (syn. *T. caries*, wheat bunt) and *T. controversa* (dwarf bunt) on wheat; *Typhula incarnata* (grey snow mold) on barley or wheat; *Urocystis* spp., e.g. *U. occulta* (stem smut) on rye; *Uromyces* spp. (rust) on vegetables, such as beans (e.g. *U. appendiculatus*, syn. *U. phaseoli*) and sugar beets (e.g. *U. betae*); *Ustilago* spp. (loose smut) on cereals (e.g. *U. nuda* and *U. avaenae*), corn (e.g. *U. maydis*: corn smut) and sugar cane; *Venturia* spp. (scab) on apples (e.g. *V. inaequalis*) and pears; and *Vertialium* spp. (wilt) on various plants, such as fruits and ornamentals, vines, soft fruits, vegetables and field crops, e.g. *V. dahliae* on strawberries, rape, potatoes and tomatoes.

In particular, the dsRNA molecules and antisense-ssRNA of the invention are capable of inhibiting the expression of at least one CYP51 gene of a fungal or oomycete phytopathogen selected from the genera *Fusarium, Blumeria, Magnaporthe, Sclerotinia, Phakopsora, Botrytis, Puccinia, Pyrenophora, Phaeosphaeria, Septoria, Cochliobolus, Ustilago, Rhynchosporium* and *Venturia*. Particular phytopthogens of these genera and their CYP51 genes are listed in Table 1 below. Preferably, the phytopathogen is a fungus of the genus *Fusarium*.

TABLE 1

Fungal and oomycete phytopathogens and CYP51 genes thereof

| Phytopathogen | Diseases | CYP51 gene(s) | [SEQ ID NO of coding sequence] |
|---|---|---|---|
| *Fusarium graminearum* (Fg) | head blight on wheat, barley, and other cereal crops | CYP51A (FGSG_04092.3)[1] | [1] |
| | | CYP51B (FGSG_01000.3)[1] | [2] |
| | | CYP51C (FGSG_11024.3)[1] | [3] |
| *Fusarium oxysporum* | wilt of tomato and other crops | CYP51A (FOXG_11545.2)[1] | [8] |
| | | CYP51B (FOXG_00394.2)[1] | [9] |
| | | CYP51C (FOXG_13138.2)[1] | [10] |
| *Fusarium verticillioides* | ear rot of corn | CYP51A (FVEG_10277.3)[1] | [11] |
| | | CYP51B (FVEG_01123.3)[1] | [12] |
| | | CYP51C (FVEG_12391.3)[1] | [13] |
| *Blumeria graminis* | Powdery mildew on grasses | CYP51 | [14] |
| *Magnaporthe grisea* | Rice seedling blight, blast of rice, oval leaf spot of graminea, pitting disease, ryegrass blast, and Johnson spot | CYP51A | [15] |
| | | CYP51B | [16] |
| *Sclerotinia sclerotinium* | White mold, cottony rot, watery soft rot, stem rot, drop, crown rot and blossom blight | CYP51B | [17] |
| *Phakopsora pachyrhizi* | Asian soybean rust | CYP51 | [18] |
| *Botrytis cinerea* | Blossom blights and fruit rots but also as leaf spots and bulb rots | CYP51B | [19] |
| *Puccinia triticina* | Rust disease on cereals | CYP51 | [20] |
| *Puccinia graminis* | Rust disease on cereals | CYP51 | [21] |
| *Puccinia recondita* | Rust disease on cereals | CYP51 | [22] |
| *Pyrenophora teres* | Blotch of barley, net blotch, and spot form net blotch | CYP51 | [23] |
| *Pyrenophora tritici* | Tan spot or helminthosporiosis on cereals | CYP51A | [24] |
| | | CYP51B | [25] |
| *Phaeosphaeria nodorum* | Glume blotch and Septoria nodorum blotch | CYP51B | [26] |
| *Septoria tritici* | Septoria leaf blotch | CYP51 | [27] |
| *Cochliobolus sativus* | Spot blotch and common root rot | CYP51B | [28] |
| *Ustilago maydis* | Smut disease on maize | CYP51 | [29] |
| *Rhynchosporium secalis* | Barley and rye scald | CYP51 | [30] |
| *Venturia inaequalis* | Apple scab disease | CYP51 | [31] |

[1]The gene designations refer to the loci in the *Fusarium* Comparative Database accessible via, e.g., the website of the Broad Institute www.broadinstitute.org.

The dsRNA molecule of the invention is capable of inhibiting the expression of one, two, three, or all CYP51 genes of a fungal or oomycete phytopathogen, and preferably is capable of inhibiting all CYP51 genes of the phytopathogen. According to a particularly preferred embodiment, the dsRNA molecule of the invention is capable of inhibiting the expression of the CYP51A gene, the CYP51B gene and the CYP51C gene of a phytopathogenic fungus of the genus *Fusarium*.

For example, the CYP51 gene(s) to be inhibited by the dsRNA molecule of the present invention is/are selected from the CYP51 genes of a phytopathogen listed in Table 1.

The dsRNA molecule can be stabilized against unwanted chemical and enzymatic degradation by reducing the dissociation of double-stranded RNA into single-stranded, non-hybridized RNA. To this end, the two hybridizing ribonucleotide sequences or regions adjacent to them can be chemically linked to each other as described, e.g., in US 2008/0171861 A1. Chemical linkage groups suitable for stabilizing regions of double stranded RNA include, but are not limited to, purine analogs replacing purines and branched nucleotide analogs replacing nucleotides. The dsRNA molecule can also be stabilized against unwanted enzymatic degradation by ribonucleotide modifications. Suitable ribonucleotide modifications include the replacement of the 2'-hydroxyl group of one or more than one ribonucleotide by, preferably, a 2'-amino or 2'-methyl group; and the replacement of one or more than one ribonucleotide by the same number of corresponding locked nucleotides, wherein the sugar ring is chemically modified, preferably by a 2'-O 4'-C methylene bridge.

The dsRNA molecule of the invention comprises a sense sequence having a high degree of identity to at least part of the coding sequence of at a CYP51 gene from a fungal or oomycete phytopathogen, and an antisense sequence being substantially complementary to said sense sequence. In this context, "a sense sequence" refers to one or more than one sense sequence, and "a CYP51 gene" refers to one or more than one CYP51 gene. Expediently, the antisense sequences encompass a substantially complementary antisense sequence for each sense sequence comprised by the same dsRNA molecule. Generally, terms such as "a sense sequence", "an antisense sequence", "a polynucleotide", "a CYP51 gene", when used herein, include the singular as well as the plural, unless stated otherwise.

According to one embodiment, the dsRNA molecule of the invention comprises
  a first sense sequence having a high degree of identity to at least part of the coding sequence of a first CYP51 gene, and
  a second sense sequence having a high degree of identity to at least part of the coding sequence of a second CYP51 gene,
wherein the first CYP51 gene and the second CYP51 gene are different CYP51 genes of a fungal or oomycete phytopathogen.

According to a further embodiment, the dsRNA molecule of the invention comprises
  a first sense sequence having a high degree of identity to at least part of the coding sequence of a first CYP51 gene,
  a second sense sequence having a high degree of identity to at least part of the coding sequence of a second CYP51 gene, and
  a third sense sequence having a high degree of identity to at least part of the coding sequence of a second CYP51 gene,
wherein the first CYP51 gene, the second CYP51 gene and the third CYP51 gene are different CYP51 genes of a fungal or oomycete phytopathogen.

The coding sequence of the at least one CYP51 gene, e.g. the first, the second and the third CYP51 gene, can be selected from the coding sequences of the CYP51 genes listed in Table 1.

According to one aspect of the invention, the dsRNA molecule is capable of inhibiting the expression of at least one CYP51 gene from *Fusarium graminearum*, and comprises a sense sequence having a high degree of identity to at least part of a sequence selected from SEQ ID NOs:1-6, and an antisense sequence being substantially complementary to said sense sequence; wherein the arrangement of the sequences within the dsRNA molecule allows hybridization of said sense sequence and said corresponding antisense sequence. According to particular embodiments of said aspect of the invention, the dsRNA molecule:
(a) is capable of inhibiting the expression of the CYP51A gene from *Fusarium graminearum* and comprises a sense sequence having a high degree of identity to at least part of SEQ ID NO:1 or SEQ ID NO:4;
(b) is capable of inhibiting the expression of the CYP51B gene from *Fusarium graminearum* and comprises a sense sequence having a high degree of identity to at least part of SEQ ID NO:2 or SEQ ID NO:5;
(c) is capable of inhibiting the expression of the CYP51C gene from *Fusarium graminearum* and comprises a sense sequence having a high degree of identity to at least part of SEQ ID NO:3 or SEQ ID NO:6;
(d) is characterized by (a) and (b);
(e) is characterized by (a) and (c);
(f) is characterized by (b) and (c); or
(g) is characterized by (a), (b) and (c).

According to preferred aspect of the invention, the dsRNA molecule is capable of inhibiting the expression of at least one CYP51 gene from *Fusarium graminearum* and comprises a sense sequence that is at least 70%, at least 75%, at least 80%, at least 85%, at least 90%, preferably at least 95% or at least 98%, and most preferably at least 99% or 100% identical to SEQ ID NO:7, and an antisense sequence being substantially complementary to said sense sequence; wherein the arrangement of the sequences within the dsRNA molecule allows hybridization of said sense sequence and said corresponding antisense sequence. According to particular embodiments of said aspect of the invention, the dsRNA molecule consists of said sense and said antisense sequence. For example, said dsRNA molecule may consist of a first RNA strand having said sense sequence and a second RNA strand having said antisense sequence.

According to a further aspect of the invention, the dsRNA molecule is capable of inhibiting the expression of at least one CYP51 gene from *Fusarium oxysporum*, and comprises a sense sequence having a high degree of identity to at least part of a sequence selected from SEQ ID NOs:8-10, and an antisense sequence being substantially complementary to said sense sequence; wherein the arrangement of the sequences within the dsRNA molecule allows hybridization of said sense sequence and said corresponding antisense sequence. According to particular embodiments of said aspect of the invention, the dsRNA molecule:
(a) is capable of inhibiting the expression of the CYP51A gene from *Fusarium* oxysporum and comprises a sense sequence having a high degree of identity to at least part of SEQ ID NO:8;
(b) is capable of inhibiting the expression of the CYP51B gene from *Fusarium* oxysporum and comprises a sense sequence having a high degree of identity to at least part of SEQ ID NO:9;
(c) is capable of inhibiting the expression of the CYP51C gene from *Fusarium* oxysporum and comprises a sense sequence having a high degree of identity to at least part of SEQ ID NO:10;
(d) is characterized by (a) and (b);
(e) is characterized by (a) and (c);
(f) is characterized by (b) and (c); or
(g) is characterized by (a), (b) and (c).

According to a further aspect of the invention, the dsRNA molecule is capable of inhibiting the expression of at least one CYP51 gene from *Fusarium verticillioides*, and comprises a sense sequence having a high degree of identity to at least part of a sequence selected from SEQ ID NOs:11-13, and an antisense sequence being substantially complementary to said sense sequence; wherein the arrangement of the sequences within the dsRNA molecule allows hybridization of said sense sequence and said corresponding antisense sequence. According to particular embodiments of said aspect of the invention, the dsRNA molecule:
(a) is capable of inhibiting the expression of the CYP51A gene from *Fusarium verticillioides* and comprises a sense sequence having a high degree of identity to at least part of SEQ ID NO:11;
(b) is capable of inhibiting the expression of the CYP51B gene from *Fusarium verticillioides* and comprises a sense sequence having a high degree of identity to at least part of SEQ ID NO:12;
(c) is capable of inhibiting the expression of the CYP51C gene from *Fusarium verticillioides* and comprises a sense sequence having a high degree of identity to at least part of SEQ ID NO:13;
(d) is characterized by (a) and (b);
(e) is characterized by (a) and (c);
(f) is characterized by (b) and (c); or
(g) is characterized by (a), (b) and (c).

According to a preferred embodiment of the invention, the dsRNA molecule is capable of inhibiting the expression of the CYP51A gene, the CYP51B gene and the CYP51C gene from a phytopathogenic *Fusarium* species; and said dsRNA molecule comprises
(i) a sense sequence having a high degree of identity to at least part of the coding sequence of said CYP51A gene;
(ii) a sense sequence having a high degree of identity to at least part of the coding sequence of said CYP51B gene;
(iii) a sense sequence having a high degree of identity to at least part of the coding sequence of said CYP51C gene; and
(iv) antisense sequences being substantially complementary to the sense sequences (i), (ii), and (iii);
wherein the arrangement of the sequences within the dsRNA molecule allows hybridization of each sense sequence with its substantially complementary antisense sequence.

In embodiments where the phytopathogenic *Fusarium* species is *Fusarium graminearum*, the coding sequence of the CYP51 genes may be the sequences set forth in SEQ ID NO:1 (CYP51A), SEQ ID NO:2 (CYP51B) and SEQ ID NO:3 (CYP51C).

In embodiments where the phytopathogenic *Fusarium* species is *Fusarium oxysporum*, the coding sequence of the CYP51 genes may be the sequences set forth in SEQ ID NO:8 (CYP51A), SEQ ID NO:9 (CYP51B) and SEQ ID NO:10 (CYP51C).

In embodiments where the phytopathogenic *Fusarium* species is *Fusarium verticillioides*, the coding sequence of the CYP51 genes may be the sequences set forth in SEQ ID NO:11 (CYP51A), SEQ ID NO:12 (CYP51B) and SEQ ID NO:13 (CYP51C).

According to a further particular embodiment of the invention, the dsRNA molecule of the invention is capable of inhibiting the expression of the CYP51A gene, the CYP51B gene and the CYP51C gene from *Fusarium graminearum*, and said dsRNA molecule comprises
a sense sequence (i) having a high degree of identity to at least part of SEQ ID NO:4,
a sense sequence (ii) having a high degree of identity to at least part of SEQ ID NO:5,
a sense sequence (iii) having a high degree of identity to at least part of SEQ ID NO:6, and
antisense sequences (iv) being substantially complementary to the sense sequences (i), (ii), and (iii);
wherein the arrangement of the sequences within the dsRNA molecule allows hybridization of each sense sequence with its substantially complementary antisense sequence.

The expression "at least part of" SEQ ID NO:4, SEQ ID NO:5 or SEQ ID NO:6 refers to at least 20 contiguous nucleotides, for example of at least 25, at least 50, at least 100, at least 150, and preferably at least 200 contiguous nucleotides of SEQ ID NO:4, SEQ ID NO:5 or SEQ ID NO:6. According to a particularly preferred embodiment of the invention, the high degree of identity of the sense sequences (i), (ii) and (iii) pertains to the entire length of SEQ ID NO:4, SEQ ID NO:5 and SEQ ID NO:6, respectively.

Due to the sequence homology of the CYP51A, CYP51B and CYP51C genes from *Fusarium* species, dsRNA molecules can be designed, wherein the sense sequences have a high degree of identity to at least part of the coding sequences of the CYP51A genes, the CYP51B genes and the CYP51C genes, respectively, from more than one phytopathogenic *Fusarium* species. For example, the sense sequences of the dsRNA can have a high degree of identity to at least part of the coding sequence of the CYP51A genes, the CYP51B genes and the CYP51C genes, respectively, from two or more *Fusarium* species selected from *F. graminearum*, *F. oxysporum* and *F. vertialioides*.

The sense and the antisense sequences are arranged within the dsRNA molecule in a manner that allows hybridization of each sense sequence with its substantially complementary antisense sequence, thus forming regions of double-stranded RNA.

According to a preferred embodiment, each sense sequence is located on a different RNA strand of the dsRNA molecule than its substantially complementary antisense sequence. Thus, the sense and antisense sequences can be located on two or more than two separate strands of the dsRNA molecule. Upon hybridization of the substantially complementary sequences the strands are joined through base pairing to form one or more than one region of double-stranded RNA. The sense sequences can be on separate strands of the dsRNA molecule. According to a particular embodiment, the substantially complementary sense and antisense sequences of the dsRNA molecule of the invention are located on two separate substantially complementary strands of the dsRNA molecule.

Alternatively, the substantially complementary sense and antisense sequences of the dsRNA molecule of the invention are located on a single strand of the dsRNA molecule. The substantially complementary sequences are arranged on the RNA single strand in a manner that upon their hybridization the strand is looped back on itself through base pairing to form one or more than one hairpin structure. A hairpin structure consists of a double-stranded stem formed by hybridization of a first polynucleotide segment with a second polynucleotide segment, and a singled-stranded loop linking the two segments.

The hybridized sense and antisense sequences of the dsRNA molecule of the invention can be comprised within one contiguous region of double-stranded RNA. According to a preferred embodiment, the dsRNA molecule of the invention comprises a region of double-stranded RNA consisting essentially (i.e. to at least 80%, at least 90%, or 100%) of the sense and antisense sequences, most preferably consisting of one sense sequence (i), one sense sequence (ii), and one sense sequence (iii), each hybridized to a substantially complementary antisense sequence.

The order of the regions of double-stranded RNA comprising the sense sequences (i), (ii) and (iii) is not particularly restricted. For example, the double-stranded RNA formed by sense sequence (i) and its antisense sequence is flanked on one side by the double-stranded RNA formed by sense sequence (ii) and its antisense sequence and on the other side by the double-stranded RNA formed by sense sequence (iii) and its antisense sequence.

The dsRNA molecules of the present invention are capable of inhibiting the expression of CYP51 gene(s) of the fungal or oomycete phytopathogen. The inhibition of CYP51 gene expression by dsRNA molecules of the present invention becomes detectable on the level of mRNA, on the level of polypeptide or both. For example, the change in the mRNA level of a CYP51 gene can be assessed by quantitative real-time PCR (qRT-PCR) or Northern Blot.

The dsRNA molecules of the present invention are effective in inhibiting the expression of CYP51 gene(s) of the fungal or oomycete phytopathogen. The generation of dsRNA molecules of the invention within a plant inoculated with the fungal or oomycete phytopathogen can result in mRNA levels of the CYP51 gene(s) which are at least 50%, at least 60%, at least 70% or, preferably, at least 75% lower compared to those in a control plant not generating RNA molecules of the invention. For example, such change in fungal or oomycete CYP51 mRNA levels (e.g. Fg CYP51A, CYP51B and CYP51C mRNA levels) can be determined in *Arabidopsis thaliana* leaves inoculated three days earlier with the fungus or oomycete (e.g. Fg macroconidia) from which the CYP51 gene(s) defining the sense sequences of the dsRNA molecule originate(s). For example, such change in fungal or oomycete CYP51 mRNA levels (e.g. Fg CYP51A, CYP51B and CYP51C mRNA levels) can alternatively be determined in barley leaves inoculated 7 days earlier with the fungus or oomycete (e.g. Fg macroconidia) from which the CYP51 gene(s) defining the sense sequences of the dsRNA molecule originate(s).

The dsRNA molecules of the invention are useful for controlling fungal or oomycete phytopathogens, e.g. phytopathogens as listed in Table 1. In particular, dsRNA molecules of the invention are suitable for controlling fungi from the genus *Fusarium*. According to a preferred aspect of the invention, the phytopathogenic fungus to be controlled is selected from *Fusarium graminearum, Fusarium oxysporum* and *Fusarium verticillioides.*

A dsRNA molecule of the invention can be capable of inhibiting the expression of two or more fungal and/or oomycete phytopathogens, and accordingly can be useful for controlling said two or more different phytopathogen species.

Controlling a phytopathogenic fungus or oomycetes refers to measures for preventing the infestation of a plant with said pathogen as well as measures for combatting or curing the pathogen infestation of a plant. The infestation of a plant with a fungal or oomycete phytopathogen can become visible as a plant disease. Accordingly, the uses and methods of the present invention for controlling a phytopathogenic fungus or oomycete are uses and methods for preventing and/or treating plant diseases caused by the phytopathogenic fungus or oomycete, e.g. those listed in Table 1.

The present invention also provides antisense-ssRNA comprising the antisense sequences but not the sense sequences of the dsRNA molecule of the invention. Such antisense-ssRNA of the invention is capable of inhibiting the expression of CYP51 gene(s) of the fungal or oomycete phytopathogen and is useful for controlling said pathogen in a manner comparable to the dsRNA molecules of the invention.

For controlling a phytopathogenic fungus or oomycete, the dsRNA molecules of the invention can be applied to a plant infested by or at risk of being infested by the phytopathogen and/or the vicinity of said plant. The dsRNA molecule of the invention is expediently applied in the form of a composition. Accordingly, the present invention provides a composition for controlling a phytopathogenic fungus or oomycete comprising the dsRNA molecule of the invention and a plant-compatible carrier.

Plant-compatible carriers can be liquids, solids or mixtures thereof, for example selected from water, alcohols (e.g. butanol organic solvents), glycols, fatty acids, mineral and plant oils, derivatives of mineral and plant oils, natural minerals (e.g. kaolins, clays, talc, chalk) and synthetic minerals (e.g. finely divided silica, silicates), waxes, solid fertilizers, cellulose derivatives (e.g. methylcellulose), and mixtures thereof. The carrier is expediently chosen so as to be compatible with the application of the composition to the plant to be protected or cured, or the vicinity thereof. For example, in liquid compositions, the carrier may include at least one surfactant (i.e. a compound modifying surface tension) to positively modify the dispersion, suspension or precipitation of the ingredients, and/or to improve wetting and spreading of the composition.

According to one embodiment of the present invention, the composition comprises isolated or purified dsRNA molecules of the invention. According to alternative embodiments, the composition of the invention comprises host cells, e.g. bacterial or yeast cells, capable of expressing dsRNA molecules of the invention, or an extract of such cells.

The composition of the invention can comprise further agents including

- RNA protecting agents that reduce or prevent unwanted chemical and/or enzymatic degradation of the dsRNA molecules, e.g. RNase inhibitors;
- compounds which enhance or promote uptake of the dsRNA by the phytopathogen, e.g. compounds which generally promote the uptake of RNA into cells such as lipofectamin; and
- phytopharmaceutical and/or plant growth promoting compounds, e.g., selected from fungicides, herbicides, insecticides, nematicides, acaricides, molluscicides, and pheromone active substances.

Compositions of the invention comprising such phytopharmaceutical and/or plant growth promoting agents can exert a broadened spectrum of biological activity. Particularly advantageous are compositions which comprise dsRNA molecules of the invention and a plant-compatible carrier together with one or more than one further fungicide.

Compositions of the invention are also suitable for controlling harmful fungi in the protection of stored products or harvest and in the protection of materials. The term "protection of materials" is to be understood to denote the protection of technical and nonliving materials, such as adhesives, glues, wood, paper and paperboard, textiles, leather, paint dispersions, plastics, cooling lubricants, fiber or fabrics, against the infestation and destruction by harmful microorganisms, such as fungi. As to the protection of wood and other materials, the particular attention is paid to the following harmful fungi: *Ascomycetes* such as *Ophiostoma* spp., *Ceratocystis* spp., *Aureobasidium pullulans, Sclerophoma* spp., *Chaetomium* spp., *Humicola* spp., *Petriella* spp., *Trichurus* spp.; Basidiomycetes such as *Coniophora* spp., *Coriolus* spp., *Gloeophyllum* spp., *Lentinus* spp., *Pleurotus* spp., *Poria* spp., *Serpula* spp. and *Tyromyces* spp., Deuteromycetes such as *Aspergillus* spp., *Cladosporium* spp., *Penicillium* spp., *Trichorma* spp., *Alternaria* spp., *Paecilomyces* spp. and Zygomycetes such as *Mucor* spp., and in addition in the protection of stored products and harvest the following yeast fungi are worthy of note: *Candida* spp. and *Saccharomyces cerevisae*.

The form of the composition of the invention is expediently adapted to the desired mode of application. Suitable forms include ready-to-use compositions as well as concentrates. For example, the composition of the invention can have the form of a sprayable liquid, a dustable powder, an emulsifiable concentrate, granules (e.g. coated, encapsulated or impregnated granules), a paste, or a water-dispersable or water-soluble powder for seed treatment. Methods for preparing such compositions are known in the art.

The invention provides a kit comprising dsRNA molecules of the invention, or a host cell capable of expressing dsRNA molecules of the invention, or the ingredients of a composition of the invention, or a composition of the invention. The kit may be supplied with suitable instructions for use.

The present invention provides the use of dsRNA molecules of the invention, or a host cell capable of expressing dsRNA molecules of the invention, or a composition of the invention for controlling the phytopathogenic fungus or oomycete.

The present invention further provides methods for controlling the phytopathogenic fungus or oomycete, wherein a plant infested by or at risk of being infested by the fungus and/or the vicinity of said plant is contacted with the composition.

Application methods for contacting a plant and/or the vicinity thereof with a composition are known in the art. Suitable application methods include, but are not limited to, spraying a liquid composition, dusting a powdery composition, incorporating a powdery or granular composition into the soil, daubing a pasty composition, and coating or film-coating plant seeds with the composition.

The dose of dsRNA molecules of the present invention applied in the method of the present invention is typically from 0.0001 to 10,000 g/ha, preferably from 0.0001 to 1,000 g/ha and more preferably from 0.001 to 300 g/ha for foliar treatment; from 0.0001 to 200 g composition per 100 kg seed, preferably from 0.001 to 150 g per 100 kg of seed; and from 0.0001 to 10,000 g/ha and preferably from 0.0001 to 5,000 g/ha for soil treatment.

The dsRNA molecules of the invention can be prepared by methods known in the art such as by classical chemical synthesis, by in vitro transcription methods, or by heterologous expression in, e.g., microorganisms (bacteria, yeasts), cell cultures or plants. Accordingly, transcription can be mediated by an endogenous RNA polymerase of the host cell in vivo, or by a cloned RNA polymerase for transcription in vivo or in vitro. The dsRNA molecules of the invention can be purified or isolated dsRNA. For example, RNA can be purified from a mixture by extraction with a solvent or resin, precipitation, electrophoresis, chromatography, or a combination thereof. Alternatively, the dsRNA may be used with no or only a minimum of purification to avoid losses due to sample processing. The RNA may be dried for storage or dissolved in an aqueous solution. The solution may contain buffers or salts to promote annealing, and/or stabilization of double-stranded RNA regions.

In the method of the present invention for controlling a phytopathogenic fungus or oomycete by applying a composition of the invention, the plant infested by or at risk of being infested by the phytopathogen and/or the vicinity of said plant is expediently contacted with an effective amount of the composition. An "effective amount" of a composition of the invention is an amount comprising an amount of dsRNA molecules of the invention that is sufficient to control the fungus. Such effective amount can vary depending on the phytopathogen to be controlled, the plant to be protected (species, variety, developmental stage), the climatic conditions and the further components of the composition. The effective amount of the composition of the invention can be determined by systematic field trials which are routine and well within the capabilities of a person skilled in the art.

The present invention also provides means and methods for controlling a phytopathogenic fungus or oomycete by generating the dsRNA molecules or the antisense-ssRNA of the invention within a plant to be protected from the fungus. Accordingly, the present invention provides a method for preparing a transgenic plant that is tolerant to a phytopathogenic fungus or oomycete by introducing into a plant a transcriptional template of at least the antisense sequences (iv) of the dsRNA molecule of the invention.

A plant to be protected from or to be treated against infestation with a phytopathogen according to the invention, e.g. a transgenic plant according to the present invention, can be a monocotyledonous or a dicotyledonous plant.

Examples of monocotyledonous plants are plants belonging to the genera *Avena* (oat), *Triticum* (wheat), *Secale* (rye), *Hordeum* (barley), *Oryza* (rice), *Panicum, Pennisetum, Setaria, Sorghum* and *Zea* (maize).

Examples of dicotyledonous plants include cotton, leguminous plants, in particular alfalfa and soy bean, rape, tomato, sugar beet, potato, ornamental plants, and trees. Further useful plants include fruit (in particular apples, pears, cherries, grapes, citrus, pineapple, and bananas), pumpkin, cucumber, wine, oil palms, tea shrubs, cacao trees, and coffee shrubs, tobacco, sisal, as well as, with medicinal plants, rauwolfia and digitalis.

The transgenic or non-transgenic plant used in the phytopathogen-controlling methods of the present invention herein is preferably selected from barley, maize, wheat, soy, oat, rye, rice, millet, sugar beet, rape, tomato, potato, cotton and tobacco; more preferably selected from barley, maize, wheat, soy, oat, rye and rice plants; and most preferably selected from barley, maize and wheat plants.

The present invention provides a DNA sequence or a multitude of DNA sequences providing a transcriptional template of at least the antisense sequences (iv) of the RNA molecule of the invention. According to a preferred embodiment, the DNA sequence(s) of the invention provide a transcriptional template of the dsRNA molecule of the invention, i.e. including the antisense sequence(s) as well as the sense sequence(s) described herein. Alternatively, the transgenic plant of the invention comprises a transcriptional template of only the antisense sequence(s), i.e. a transcriptional template of the antisense-ssRNA of the invention.

The DNA sequence(s) of the invention can further comprise at least one promoter. The promoter comprised by the DNA sequence(s) of the invention is operably linked to the transcriptional template so as to allow the generation of the antisense-ssRNA or the dsRNA molecule of the present invention by transcription. Preferably, said promoter is a promoter that is functional in a plant cell to allow generation of the antisense-ssRNA or the dsRNA molecule of the present invention by a plant. The promoter can be selected from constitutive promoters and regulated promoters.

Non-limiting examples of constitutive promoters include the 35S promoter and the 19S promoter from cauliflower mosaic virus (CaMV35S and CaMV19S; U.S. Pat. No. 6,255,560), an ubiquitin promoter such as *Arabidopsis* ubiquitin-10 promoter (UBQ10) (EP 1210446, EP 342926) an opine promoter (EP 729514), and an active promoter such as the rice actin 1 promoter (Act-1).

Regulated promoters include inducible promoters, tissue-specific promoters and development-specific promoters. Non-limiting examples of chemically regulated inducible promoters include the alcohol dehydrogenase I gene promotor (alcA) (EP 637339); tetracycline-responsive promoter systems, e.g. promoter systems including a tetracycline repressor protein (TetR), a tetracycline operator sequence and a tetracycline transactivator fusion protein, which is the fusion of TetR and a herpes simplex virus protein 16 (VP16) activation sequence (U.S. Pat. Nos. 6,242,667 and 6,252,136); steroid-responsive promoters, e.g. promoters based on ecdysone receptors, human estrogen receptor or rat glucocorticoid receptor (EP 1232273, EP 1242604, U.S. Pat. No. 6,379,945, EP 1112360); metal-regulated promoters, e.g., derived from metallothionein; and promoters derived from pathogenesis-related proteins, e.g. from *Arabidopsis* or maize (U.S. Pat. No. 5,689,044, EP 1056862). Non-limiting examples of physically regulated inducible promoters include cold- and heat-shock-induced promoters (EP 159884, EP 787194) as wells as light-inducible promoters (EP 310619) and light-repressible promoters (U.S. Pat. No. 5,639,952, EP 1077257). Non-limiting examples of tissue-specific promoters include root-specific promoters (EP 1248850), fruit promoters (EP 316441, EP 968292, EP 973922), and seed promoters (EP 255378, EP 781849, U.S. Pat. No. 6,642,437, EP 1019517). Particularly suitable regulated promoters for the present invention are promoters induced by the presence of a phytopathogenic fungus or oomycete but not by useful organisms such as the mycorrhiza; and promoters which are active on the site of the entry of the phytopathogenic fungus or oomycete, such as epidermis-specific promoters. Inducible promoters can be used to transiently generate the antisense ssRNA or the dsRNA molecule of the invention, e.g. at times when there is an acute or increased risk of infestation by fungal or oomycete phytopathogens.

The present invention provides an isolated polynucleotide having or comprising the DNA sequence(s) of the present invention, or a multitude of isolated polynucleotides having or comprising the DNA sequences of the present invention. Said isolated polynucleotides can be transformation vectors useful for introducing DNA sequences into a plant. Such plant transformation vectors include plasmids (e.g., Ti plasmids, Ri plasmids, plasmids of the pUC series or the M13mp series, pBR322), viral vectors (e.g. derived from potato virus X, tobacco rattle virus, Gemini virus) and other vectors known in the art of genetic engineering. The plant transformation vectors can comprise DNA sequences which facilitate plant transformation and/or selection, such as sequences encoding plant selection markers (e.g. the bar gene) and T-DNA sequences.

The present invention provides methods for preparing a transgenic plant comprising the introduction of the DNA sequence(s) of the invention into the plant. The DNA sequence(s) can be introduced in the form of the isolated polynucleotide(s) of the invention (e.g. in the form of plant transformation vectors). A number of well-known methods are available for introducing polynucleotides into a plant cell. Suitable plant transformation methods include, but are not limited to, plant transformation by means of T-DNA and *Agrobacterium tumefaciens* or *Agrobacterium rhizogenes* (EP 0116718), plant transformation using viral vectors and viral infection (EP 0067553, U.S. Pat. No. 4,407,956, WO 9534668, WO 9303161), plant transformation by means of pollen (EP 0270356), fusion of protoplasts, polyethylene glycol-induced DNA uptake, liposome-mediated transformation (U.S. Pat. No. 4,536,475), biolistic DNA introduction (Fromm et al., Bio/Technology 8(9):833-9, 1990), electroporation, microinjection, and incubation of dry plant embryos in DNA-comprising solution.

A transgenic plant of the present invention is a plant, wherein at least one cell of the plant contains a DNA sequence or multitude of DNA sequences providing a transcriptional template of at least the antisense sequence(s) of the dsRNA molecule of the invention (i.e. a transcriptional template for the antisense-ssRNA or the dsRNA molecule of the invention). Preferably, said DNA sequence(s) of the invention is/are stability integrated into a chromosome or a stable extra-chromosomal element of the transgenic plant, so that the DNA sequence(s) can be passed on to the progeny of the transgenic plant. The tolerance to phytopathogenic fungi and/or oomycetes conferred by the DNA sequence(s) of the invention can thus be inherited by the progeny of the transgenic plant. The transgenic plant of the present invention is preferably a cereal crop, e.g. a barley plant, capable of generating antisense-ssRNA or dsRNA molecules for controlling one or more than one phytopathogen, in particular selected from phytopathogenic fungi of the genus *Fusarium*, e.g. *F. graminearum*.

In addition to direct transformation of a plant with recombinant DNA sequence(s) of the invention, transgenic plants can be prepared by selfing plants having said recombinant DNA sequence(s), or by crossing a first plant having said recombinant DNA sequence(s) with a second plant lacking such recombinant DNA sequence. The resulting seed can be used to grow progeny plants including plant lines comprising the DNA sequence(s) of the present invention. For example, DNA sequence(s) of the invention can be introduced into a first plant line that is amenable to transformation to produce a transgenic plant that can be crossed with a second plant line to introduce said DNA sequence(s) into the second plant line. It may be advantageous to express DNA sequence(s) of the invention in a male-sterile plant, for example, as a means for reducing concern about transgene flow to neighboring plants. The present invention can be, in practice, combined with other anti-pathogen traits in a plant.

According to a preferred embodiment, the transgenic plant of the invention is capable of generating the antisense-ssRNA or the dsRNA molecule of the invention. Said antisense-ssRNA and the dsRNA molecule of the invention are capable of inhibiting the expression of the CYP51 gene(s) of the fungal or oomycete phytopathogen, preferably the CYP51A, CYP51B and CYP51C genes of a phytopathogenic fungus of the genus *Fusarium*. The mRNA levels of said CYP51 gene(s) in a transgenic plant of the invention inoculated with the phytopathogen can be at least 50%, at least 60%, at least 70% or, preferably, at least 75% lower compared to those in a control plant not generating antisense-ssRNA or dsRNA molecules of the invention. Such change in mRNA levels of the CYP51 gene(s) can be determined, e.g., in plant leaves inoculated three days earlier with the phytopathogen (e.g. *Fusarium* macroconidia). The control plant is a plant that is sensitive to the phytopathogen, and is grown and inoculated with the phytopathogen like the transgenic plant it is compared with. The control plant can be a plant that differs from the transgenic plant of the invention in lacking a transcriptional template of the antisense-ssRNA or the dsRNA molecule of the invention. For example, a transgenic plant comprising an empty vector or marker gene but not DNA sequence(s) of the invention or a non-transgenic (i.e. wild-type) plant can be used as control plant. Expediently, the expression profiles of the transgenic plant of the invention and the corresponding control plant differ only in the generation of the antisense-ssRNA or the dsRNA molecules of the invention, or lack thereof.

The present invention also provides methods for controlling the phytopathogenic fungus or oomycete, wherein the methods comprise the cultivation of a transgenic plant of the invention to allow the generation of the antisense-ssRNA or the dsRNA molecule of the invention by the plant (i.e. the generation of RNA comprising at least the antisense sequence(s) of the dsRNA molecules of the invention). The generation of antisense-ssRNA or dsRNA molecules of the invention by the transgenic plant can confer tolerance to the phytopathogenic fungus or oomycete. In a phytopathogen-tolerant transgenic plant of the present invention, the severity and/or frequency of the infestation with the phytopathogen can be reduced by at least 5%, at least 20%, at least 50%, at least 60%, preferably at least 75%, at least 80%, at least 90%, at least 95% or 100% compared to a corresponding control plant. Alternatively, the pathogen-tolerance of a transgenic plant of the present invention can be described by reference to a relative susceptibility index which compares the susceptibility of the transgenic plant to said pathogen with the susceptibility of a control plant to said pathogen, the latter being set to 100%. The relative susceptibility index of transgenic plants of the present invention can be less than 95%, less than 80, less than 50%, less than 40%, preferably less than 35%, less than 20% or less than 10%.

Tolerance of a plant to fungal or oomycete infestations can be tested by experimental inoculation with a phytopathogenic dose of the fungus or oomycetes (e.g. by contacting the plant or part thereof with a suspension of fungal conidia). The fungal or oomycete infestation can be evaluated, for example by comparing the degree of fungal or oomycete infestation in the transgenic plant with the degree of fungal or oomycete infestation in a corresponding control plant. Quantifiable parameters include, but are not limited to, the relative number of infested plants, the total number of infested plants within a given plot size; the average number of diseases symptoms; the relative size of leaf area showing fungus-induced discolorations, necrosis or fungal growth; the average kernel number and/or weight per plant; or the yield per cultivated area. For example, after a given time (such as 3 or 7 days after) inoculation with the phytopathogen, the infested leave area of a transgenic plant of the invention can be at least 50%, at least 60%, at least 70%, preferably at least 75%, at least 80 or at least 90% smaller than the infested leave area of a corresponding control plant not generating antisense-ssRNA or dsRNA molecules of the invention.

The methods of controlling a phytopathogen described herein using a composition and/or a transgenic plant of the invention are useful for increasing the yield and/or the quality of plants. Particular advantages of these methods of the invention include:

The antisense-ssRNA or the dsRNA molecules of the invention are highly selective for the phytopathogenic fungus to be controlled. Thus, benevolent organisms such as mycorrhiza or bees are not affected.

Humans and animals consuming food produced from a transgenic plant of the invention, or from plant treated with dsRNA molecules of the invention are not affected by the antisense-ssRNA or the dsRNA molecules of the invention which are highly selective and, being biodegradable RNA, do not persist and accumulate in the environment.

Antisense-ssRNA or dsRNA molecules of the invention can be expressed in or transported to portions of the plant which are difficult to reach with chemical treatment, thus providing a comprehensive protection of the plant.

The anti-fungal activity of the transgenic plants of the present invention does not rely on the expression of new proteins within the plant which might pose an allergenic risk.

The transgenic plants of the present invention can have a high proteomic homology or even total proteomic identity with the corresponding parent, e.g. wildtype, plants.

EXAMPLES

TABLE 2

List of primers useful for PCR and qPCR studies

| No. | Primer name | Primer sequence | Application | SEQ ID NO |
|---|---|---|---|---|
| 1 | CYP51A_F | CGGTCCATTGACAATCCCCGT | Cloning CYP51A | 32 |
|   | CYP51A_R | GCAGCAAACTCGGCAGTGAG | Cloning CYP51A | 33 |
| 2 | CYP51B(AatII)_F | GACGTCCAGCAAGTTTGACGAGTC | Cloning CYP51B, dsRNA synthesis | 34 |
|   | CYP51B(NcoI)_R | CCATGGAGAGTTCATAAGGTGCTTCA | Cloning CYP51B | 35 |
| 3 | CYP51C(BcuI)_F | ACTAGTATTGGAAGCACCGTACAAT | Cloning CYP51C | 36 |
|   | CYP51C(SacI)_R | GAGCTCCATTGGAGCAGTCATAAACAA | Cloning CYP51C, dsRNA synthesis | 37 |
| 4 | CYP51B (HindIII)_F | AAGCTTCAGCAAGTTTGACGAGTC | Plant transformation | 38 |
|   | CYP51C (XmaI)_R | CCCGGGCATTGGAGCAGTCATAAACAA | Plant transformation | 39 |
| 5 | T7_F | TAATACGACTCACTATAGGCAGCAAGTTTGACGAGTC | dsRNA synthesis | 40 |
|   | T7_R | TAATACGACTCACTATAGGCATTGGAGCAGTCATAAACAA | dsRNA synthesis | 41 |
| 6 | CYP51A4_F | CCTTTGGTGCCGGTAGACAT | Real-time RT-PCR | 42 |
|   | CYP51A4_R | CCCATCGAATAAACGCAGGC | Real-time RT-PCR | 43 |
| 7 | QCYP51B_F | TCTACACCGTTCTCACTACTCC | Real-time RT-PCR | 44 |
|   | QCYP51B_R | GCTTCTCTTGAAGTAATCGC | Real-time RT-PCR | 45 |

TABLE 2-continued

List of primers useful for PCR and qPCR studies

| No. | Primer name | Primer sequence | Application | SEQ ID NO |
|---|---|---|---|---|
| 8 | CYP51C2_F | CGAGTCCCTGGCACTGAATG | Real-time RT-PCR | 46 |
|   | CYP51C2_R | GCTCATCACCCCAAAACCGT | Real-time RT-PCR | 47 |
| 9 | qpcrBtubulin_F | ATCTCGAGCCCGGTACCATGG | Real-time RT-PCR | 48 |
|   | qpcrBtubulin_R | CTCGGTGTAATGACCCTTGGCC | Real-time RT-PCR | 49 |

A) Methods Used in the Examples i) Construction of CYP51A, CYP51B and CYP51C Templates and Synthesis of dsRNA Gene annotations for Fg sterol 14 alpha-demethylases (CYP51) were obtained from database of the Broad Institute www.broadinstitute.org. Primers were designed to generate PCR amplicons of 200-300 bp length corresponding to exons of selected genes: 294 bp of CYP51A (SEQ ID NO:4), 220 bp of CYP51B (SEQ ID NO:5), and 238 bp of CYP51C (SEQ ID NO:6). Genomic template DNA was extracted from Fg using DNeasy Plant Mini Kit (Qiagen). All three amplicons were stacked into pGEM-T Easy cloning vector (Promega) (FIG. 5). The stacked clone (CYP51B-CYP51A-CYP51C) was used as template for the synthesis of dsRNA (CYP3RNA; SEQ ID NO:7) using primers cyp51B (Aatll)_F and cyp51C (Sacl) R (Table 2). Synthesis of dsRNA for in vitro studies was performed using BLOCK-iT RNAi TOPO Transcription Kit (Invitrogen) as well as MEGAscript® Kit High Yield Transcription Kit (Ambion). Following MEGAscript® protocols, primer pairs T7_F and T7_R with T7 promoter sequence at 5' end of both forward and reverse primers were designed for amplification of dsRNA (Table 2).

ii) Preparation of Fungal Macroconidia and In Vitro Silencing RNA Treatment

Both Fg wildtype (wt) strain and GFP-expressing Fg strain WT-GFP (Jansen et al., Proc Natl Acad Sci USA. 46:16892-16897. 2005) were routinely cultured on synthetic nutrient SNA-medium (Nirenberg, Can. J. Bot. 59:1599-1609. 1996). Plates were incubated at room temperature under constant illumination from one near-UV tube (Phillips TLD 36 W/08) and one white light tube (Phillips TLD 36 W/830HF). Conidia were harvested from 1-week-old cultures with a sterile glass rod and sterile water. Macroconidia were filtered through 4 layers of sterile mira-cloth, collected and washed three times with sterile distilled water, and finally diluted to 100 macroconidia in a volume of 100 μl liquid SNA medium, and plated in a 96-well micro-titer plate. 1.5 μg of dsRNA (600 ng/μl) suspended in 2.5 μl of 50× annealing buffer was added to fungal samples and equal volume of 50× annealing buffer was added to the control sample. Plates were incubated at room temperature. After incubation for 72 h, microscopic studies were performed with an inverted microscope (Leica DM IL). Each experiment was done in triplicate. In parallel, experiments were conducted with tebuconazole (Sigma Aldrich). Five mg of tebuconazole was suspended in 1 ml absolute ethanol to obtain a stock solution of 5 mg/ml. Control sample included addition of equal volume of solvent (sterile water and alcohol) without tebuconazole.

iii) Generation of Transgenic *Arabidopsis* Plants

The dsRNA construct CYP3RNA was amplified by gene specific primers CYP51B-HindIII_F and CYP51C-Xmal_R (Table 2), and cloned into p7U10-RNAi binary vector (DNA cloning service) containing selectable marker gene bar under control of the *Arabidopsis* Ubiquitin-10 promoter (UBQ10) and inverted constitutive CaMV35s promoter (FIG. 5). The resulting plasmid construct p7U10-CYP3RNA (FIG. 7) was introduced into the *Agrobacterium tumefaciens* strain AGL1 (Lazo et al., Biotechnology (NY). 9:963-7. 1991) by electroporation. Plant transformation and regeneration was performed as described (Bechtold et al., C. R. Acad. Sci. Paris, Life Sciences 316:1194-1199. 1993), and transformants were selected by Basta (7 mg/L, Duchefa Biochemies).

iv) Molecular Screening of *Arabidopsis* Transformants

Genomic DNA from young leaves of 5-week-old transgenic (T1) and non-transgenic *A. thaliana* lines was extracted using the CTAB method (Chen et al., Plant Mol Biol Rep 17:53-57. 1999). Integration of CYP3RNA into the *Arabidopsis* genome was confirmed by PCR using gene specific primers CYP51B-HindIII_F and CYP51C-Xmal_R (Table 2).

For detecting siRNA, total RNA was extracted from the *Arabidopsis* lines using TRIzol reagent (Invitrogen) following the manufacturer's protocol. A total of 15 μg total RNA was separated in a 16% polyacrylamide-7 M urea gel, and transferred onto Hybond Nylon membrane (Amersham, UK) using a semidry blotter (BioRad) at constant current (250 mA) for 3 h. The RNA was UV-cross-linked to the membrane at 1200×100 μjoules (UV Stratalinker) energy. The membrane was pre-hybridized for 45 min at 42° C. in 20 ml PerfectHyb-Puffer (Sigma). The complete 791 bp CYP3RNA PCR amplicon was used as a template for random labeling (Random Primer DNA Labeling with Kit, NEB), added to the hybridization buffer, and hybridized overnight at 42° C. The membrane was washed twice at room temperature with 5×SSC+0.01% SDS. The membrane was exposed on phosphorimaging screens (Bio-Rad) and signals were detected using a molecular imager and the Quantity One software (BioRad). A parallel loading of low range RNA marker (Fermentas) was used as size marker.

v) *Arabidopsis* Plant Infection Assay

For the leaf infection assay, Fg conidia concentration in the inoculum was adjusted to $5\times10^4$ conidia per ml. For each transgenic line (T2) and control plants (empty vector and Col-0 wild type) twenty rosette leaves of 15 different 5-week-old plants were detached and transferred to square petri plates containing 2% agar/water. Inoculation was carried out as described by Koch et al., J Phytopathology 160(10):606-610. 2012. For assessing the progression of disease symptoms, the lesion size (in cm) was measured by 3 dpi from the digital images using the free software ImageJ program www.rsb.info.nih.gov. The percentage of leaf area showing infestation symptoms relative to the non-inoculated leaf was calculated. Infested leaves were collected at 3 dpi, transferred into 2 ml tubes containing 1 ml of trypan blue solution (10 g of phenol, 10 ml of glycerol, 10 ml of lactic acid, 10 mg trypan blue, dissolved in 10 ml of distilled water), followed by boiling for 3 min. The leaves were then destained in 1 ml of chloral hydrate solution (2.5 g of chloral hydrate dissolved in 1 ml distilled water) overnight, and analyzed under a light microscope (Zeiss Axioplan 2 Imaging). GFP-tagged Fg was analyzed using a confocal microscope (Leica TCS SP2).

vi) Fungal Transcript Analysis

Figure 7:
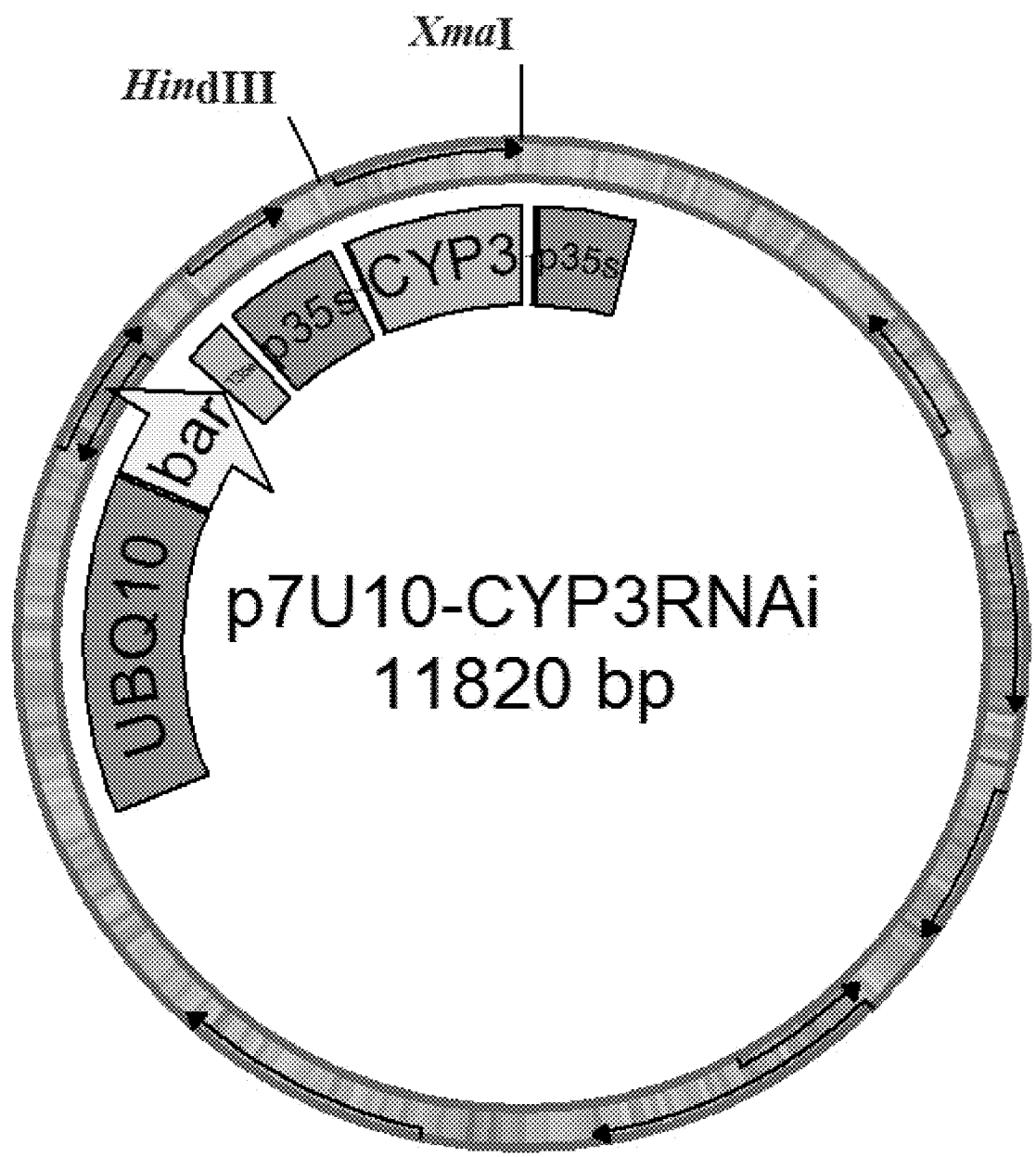
Figure 8:
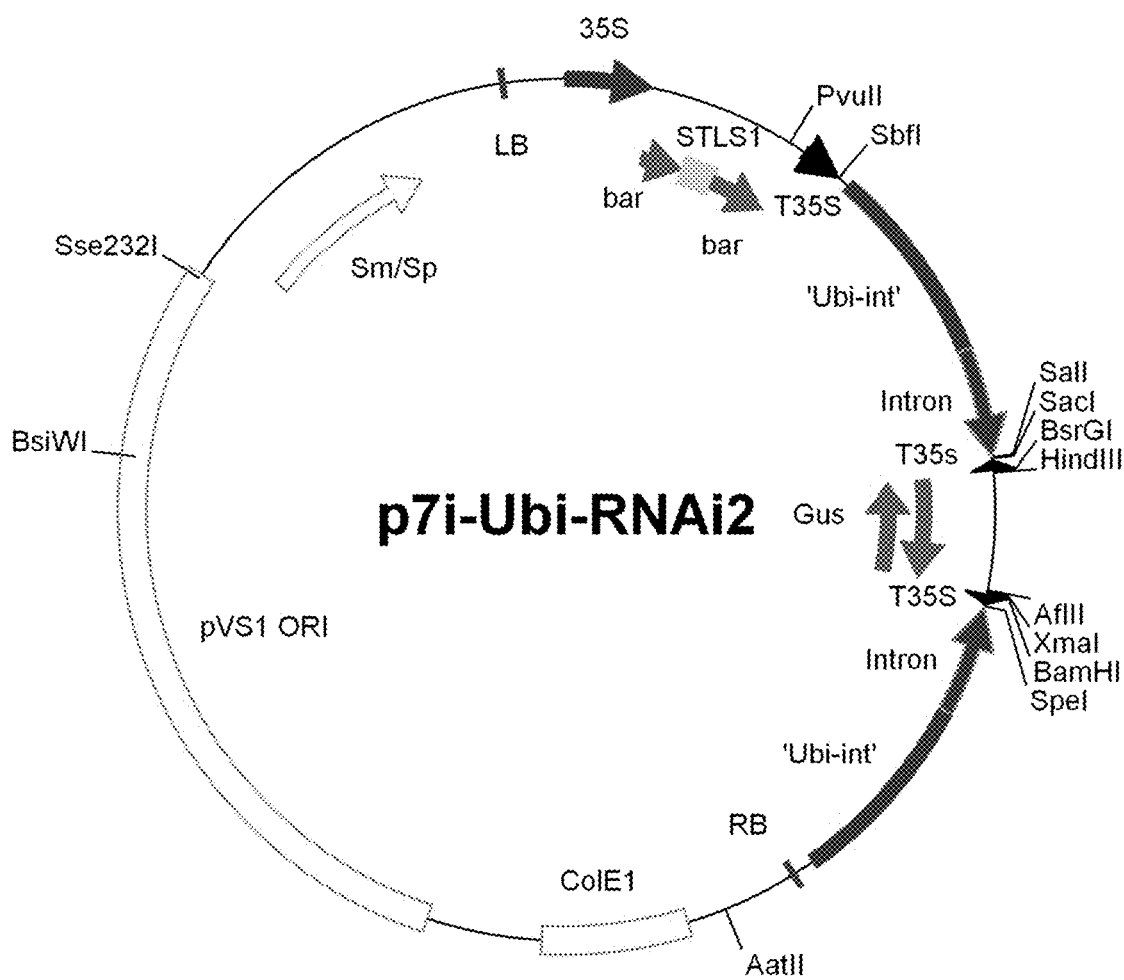
Figure 9:
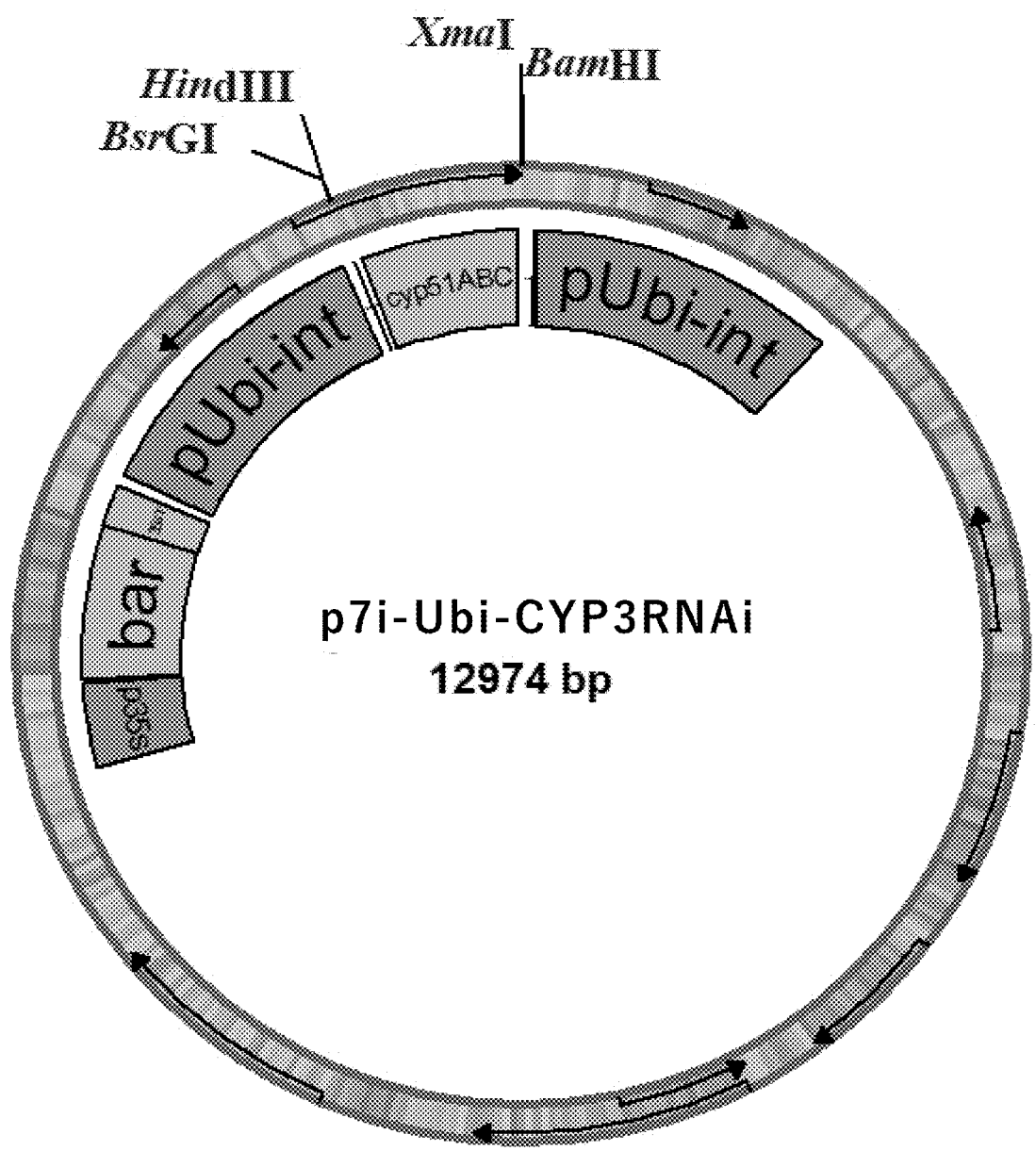
Figure 10:
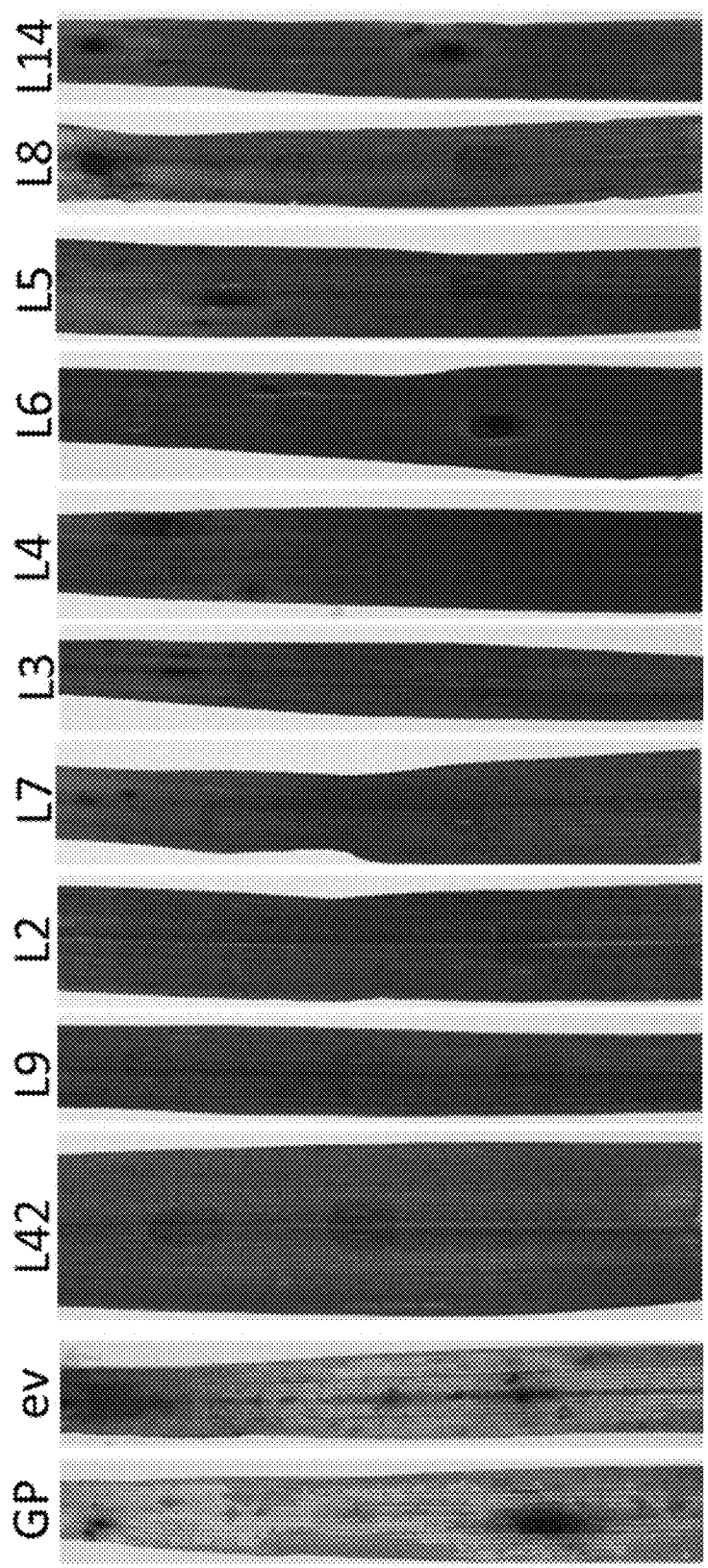
Figure 11:
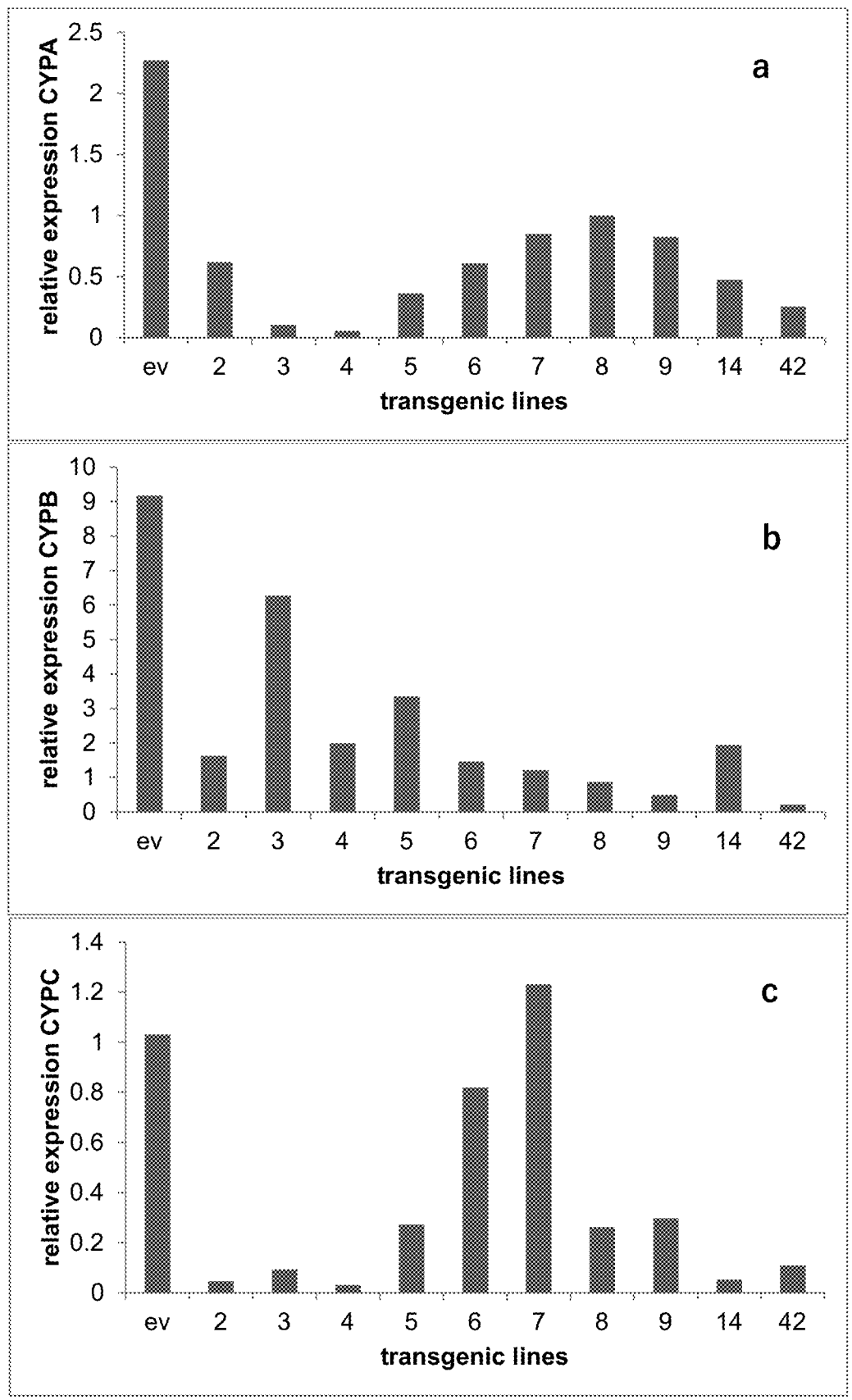

To assess silencing of the CYP51 genes in Fg, mRNA expression analysis was performed using quantitative real-time RT-PCR (qRT-PCR). For the in vitro assay $1.2\times10^5$ Fg conidia were grown in 2 ml liquid SNA medium. 162 μg of dsRNA suspended in 200 μl of nuclease free water (810 ng/μl) was added. Samples were grown at room temperature while shaking (72 h). For the in vivo assay, detached *Arabidopsis* leaves were inoculated with Fg macroconidia and collected 3 days after inoculation (dai). RNA extraction from the fungal in vitro sample as well as diseased leaves was performed with TRIzol® (Invitrogen, Germany) following manufacturer's instructions. Freshly extracted mRNA was used for cDNA synthesis using QuantiTect® Reverse Transcription kit (QIAGEN, Germany). cDNA was stored at −20° C. For qRT-PCR, 50 ng of cDNA was used as template in the Applied Biosystems 7500 FAST real-time PCR system. Amplifications were performed in 7.5 μl of SYBER green JumpStart Taq ReadyMix (Sigma-Aldrich, Germany) with 0.5 pmol oligonucleotides. Each sample had three repetitions. Primers were used for studying expression of target CYP51 genes with reference to beta-tubulin gene (Table 2) After an initial activation step at 95° C. for 5 min, 40 cycles (95° C. for 30 sec, 53° C. for 30 sec, 72° C. for 30 sec) were performed. Ct values were determined with the 7500 Fast software supplied with the instrument. Transcript levels of CYP51 genes were determined via the $2^{-\Delta\Delta Ct}$ method (Livak et al., Methods 25:402-408. 2001) by normalizing the amount of target transcript to the amount of beta-tubulin.

vii) Spraying of dsRNA and Leaf Infection Assay

Leaves of 2-3 week-old barley wild type plants cultivar Golden Promise were detached and transferred into square Petri plates containing 1% agar. The Leaves were then sprayed with dsRNA. The dsRNA was generated using MEGAscript® RNAi Kit (Invitrogen). Following MEGAscript® protocols, primer pairs T7_F and T7_R with T7 promoter sequence at 5' end of both forward and reverse primers were designed for amplification of dsRNA (cf. Table 2). For the application by spraying, the dsRNA was diluted in 500 μl 0.02% (v/v) Tween 20 to a final concentration of 20 ng/μl. Spraying of the leaves was carried out using a spray flask (10 ml capacity). Each plate containing six detached leaves was evenly sprayed with CYP3RNA dsRNA, TE-buffer only or GFP-dsRNA, respectively, by giving 3-4 puffs. Thereafter, the plates were left standing open until the surface of each leaf was dried (which took approximately 2 h) and were then covered with lids. 48 h after spraying, the leaves were treated with suspension of Fg conidia in 0.02% (v/v) Tween 20 at a concentration of $2\times10^4$ conidia per ml by applying a 20 μl-droplet of suspension to each of the upper, the middle and the lower part of the leaf. Again, the plates were covered with lids and incubated for 6 days at room temperature. To evaluate infection severity, fungal growth was evaluated by measuring the relative amount of fungal gene expression using qPCR. For this purpose, the droplets on each leaf were removed using a filter paper, the leaves were collected in 15 ml tubes and stored at −80° C. until DNA was extracted.

viii) DNA Extraction and PCR Analysis for Fungal Quantification

To assess inhibition of fungal growth the relative amount of fungal genomic DNA was measured using quantitative PCR (qPCR). DNA was extracted using the CTAB method (Chen et al., Plant Mol Biol Rep 17:53-57. 1999). For qPCR, 50 ng of DNA was used as template in the Applied Biosystems 7500 FAST realtime PCR system. Amplifications were performed in 7.5 μL of SYBER green JumpStart Taq ReadyMix (Sigma-Aldrich) with 0.5 pmol oligonucleotides. Each sample had three repetitions. Primers were used for determining the amount of fungal genomic beta-tubulin DNA with reference to barley genomic ubiquitin DNA. After an initial activation step at 95° C. for 5 min, 40 cycles (95° C. for 30 sec, 57° C. for 30 sec, 72° C. for 30 sec) were performed. Ct values were determined with the 7500 Fast software supplied with the instrument. Transcript levels of beta-tubulin gene were determined via the $2^{-\Delta\Delta Ct}$ method (Livak et al., Methods 25:402-408. 2001) by normalizing the amount of fungal beta-tubulin DNA to the amount of plant ubiquitin DNA.

B) Examples

Example 1: Inhibition of Fungal Growth and Silencing of Fg CYP51 Genes by Direct Application of dsRNA A 791 bp dsRNA (CYP3RNA) complementary to all three fungal CYP51 genes (FIG. 5) was generated. Microscopic analysis of Fg macroconidia treated with CYP3RNA revealed swelling of hyphal tips by 48 h post treatment (hpt, data not shown). By 72 hpt, the morphological changes had become more pronounced, particularly at hyphal tips (FIG. 1*a*,ii). In comparison, no such swelling was detected in the mock-treated control (FIG. 1*a,i*). Since CYP51 proteins are the target of azole fungicides, also the phenotype of Fg macroconidia treated with tebuconazole was monitored. Fg macroconidia treated with tebuconazole (5 mg/l) exhibited a phenotype comparable to that elicited by CYP3RNA treatment (FIG. 1*a,iii*).

The similar phenotype of CYP3RNA- and tebuconazole-treated Fg indicated that the dsRNA silenced the expression of one or more CYP51 genes. This was confirmed by quantifying the transcript levels for CYP51A, CYP51B, and CYP51C in control and dsRNA-treated Fg macroconidia at 72 hpt using qPCR with beta-tubulin as the reference gene. Transcripts for all three genes were significantly reduced in Fg macroconida treated with CYP3RNA as compared to the mock controls (FIG. 1*b*).

Fungal growth (determined based on optical densities of Fg cultures at 600 nm at 0 hpt and 72hpt) was strongly inhibited by CYP3RNA in a dose dependent manner (FIG. 2).

The ability of CYP3RNA to reduce the growth of Fg and to silence the CYP51 genes in Fg macroconidia indicates that the fungus can take up a 791 bp dsRNA without further delivery support, such as polyethylene glycol, calcium chloride, lipofectamine or electroporation.

Example 2: Expression of CYP3RNA in Planta Confers Resistance to Fg

*Arabidopsis thaliana* Col-0 plants were transformed with either p7U10-CYP3RNA, which contains two inverted 35S promoters that drive the constitutive production of sense and antisense copies of CYP3RNA, or an empty vector (ev)

control (FIGS. 7 and 8). Resistance to Fg was assessed by inoculating detached leaves of 5-week-old *Arabidopsis* T2 plants (expressing CYP3RNA) and the respective *Arabidopsis* Col-0 ev control plants with $5 \times 10^4$ Fg macroconidia per ml (cf. method v) above).

Figure 3:
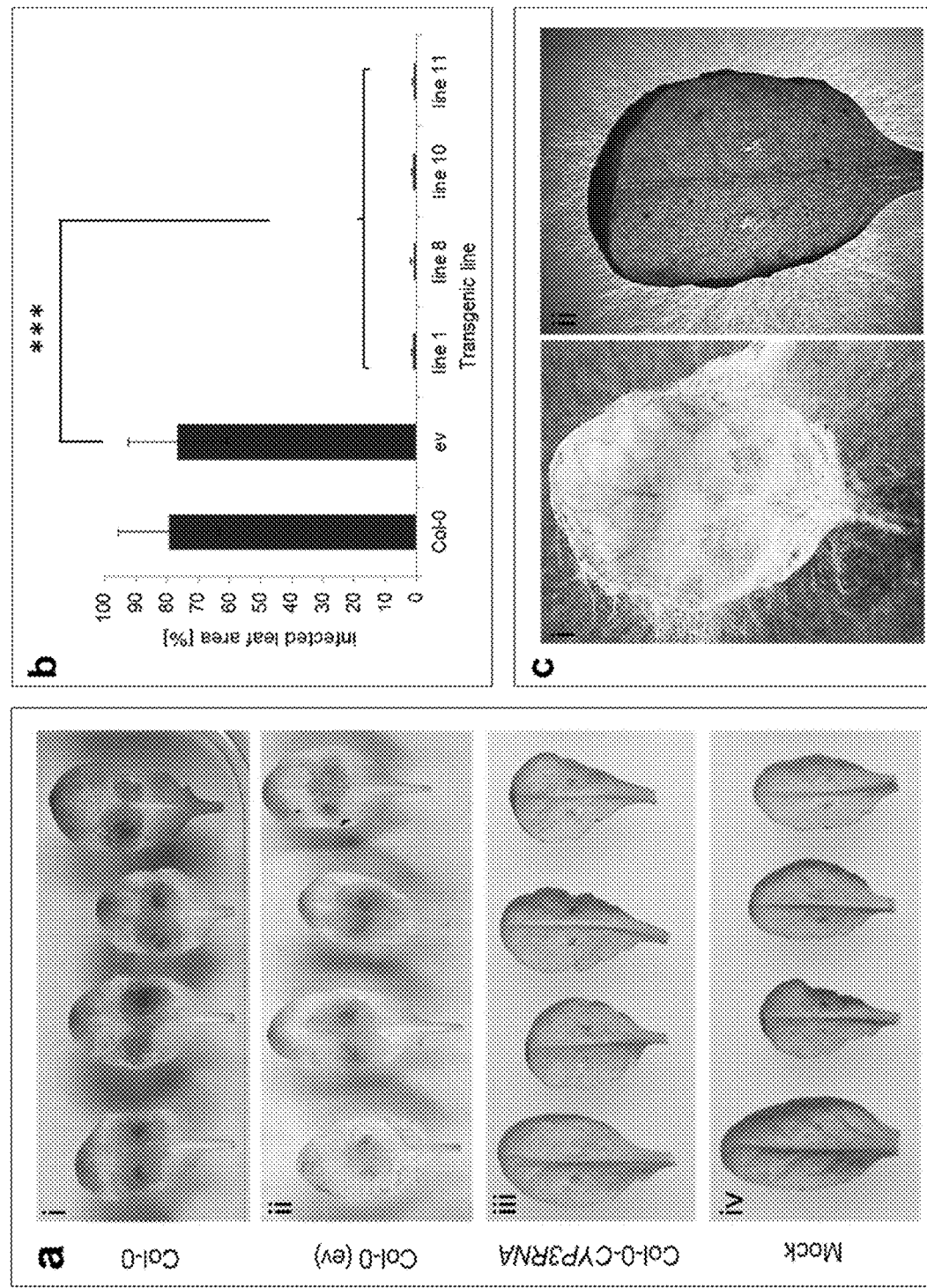
Figure 4:
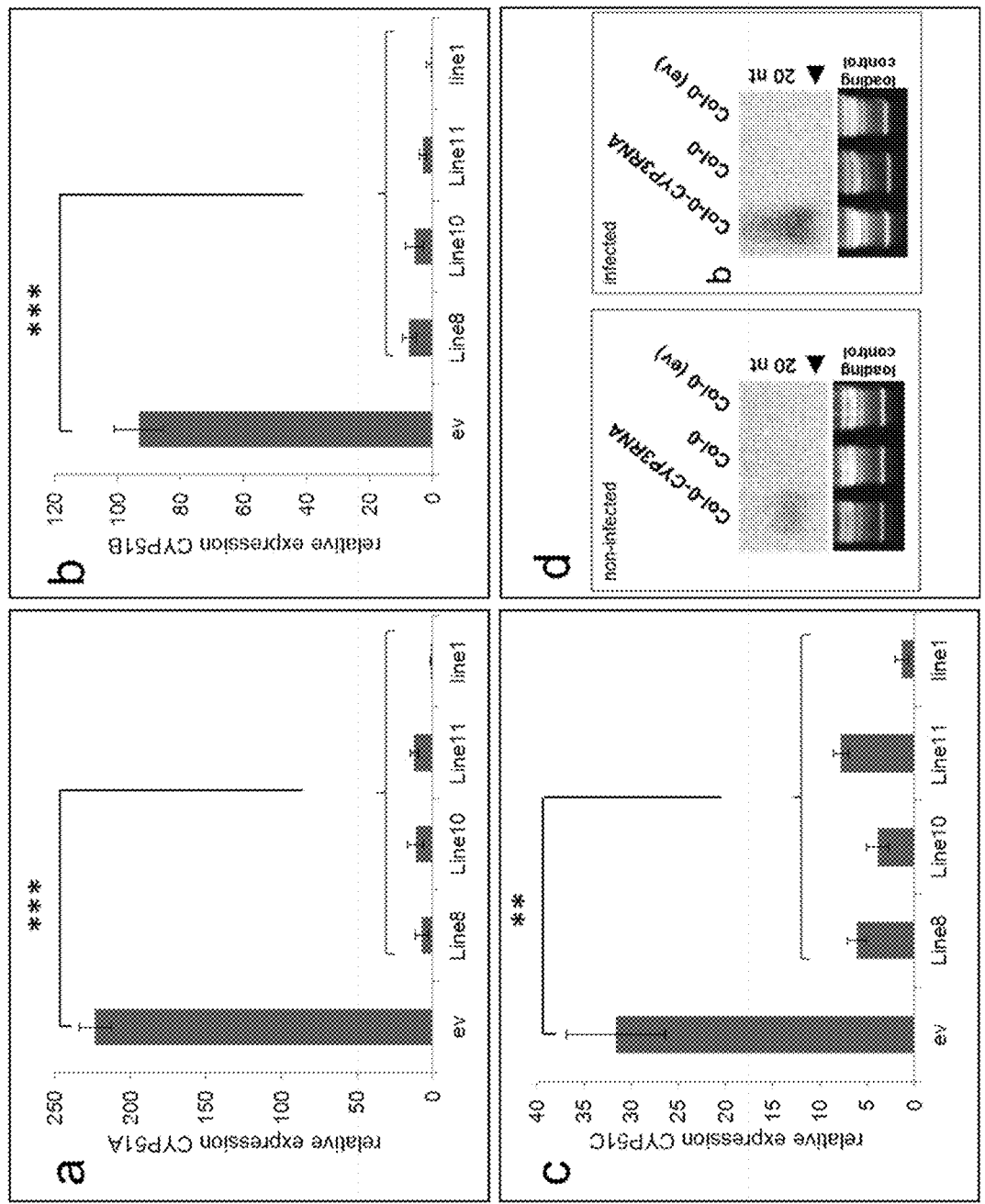
Figure 5:
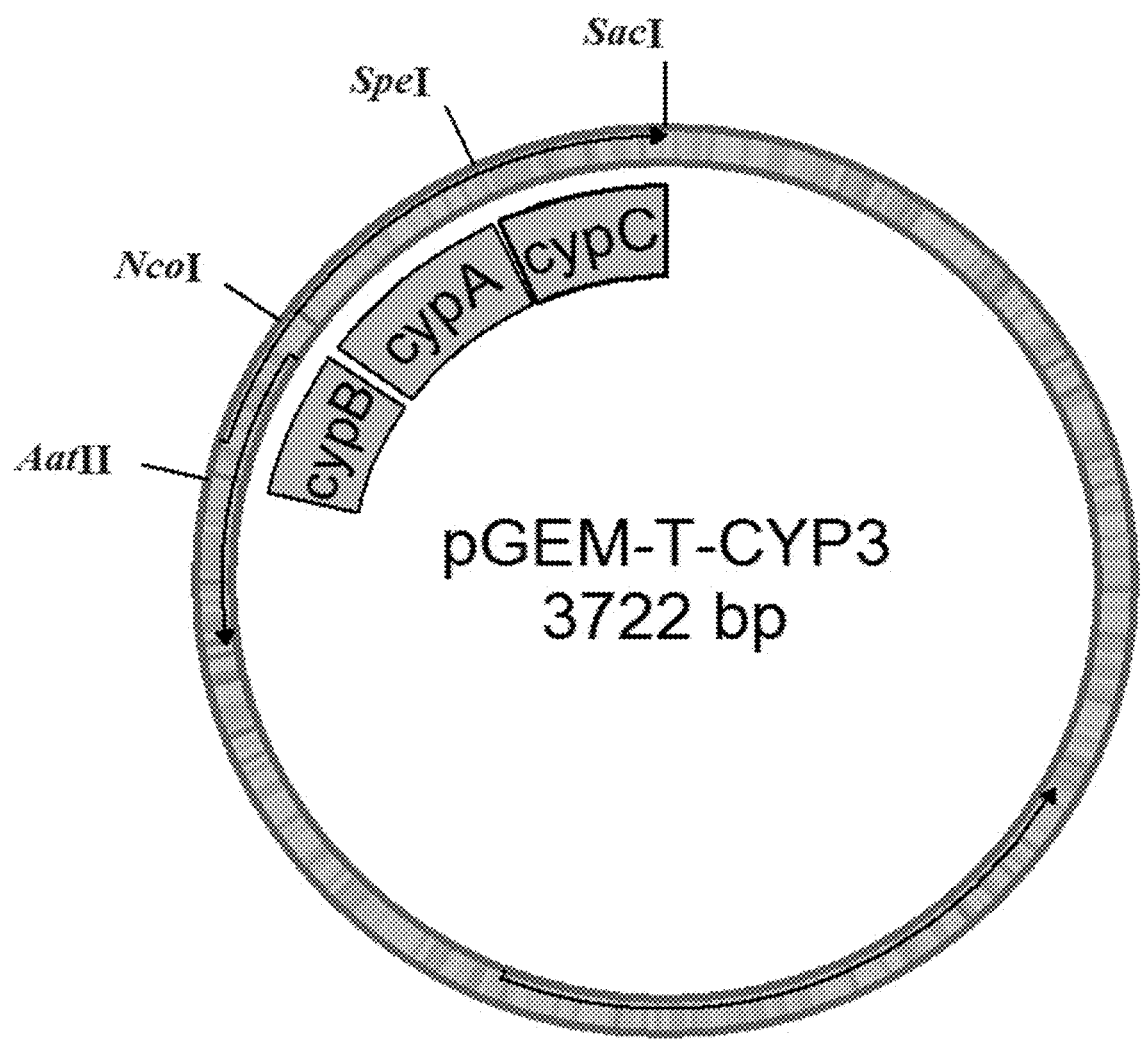
Figure 6:
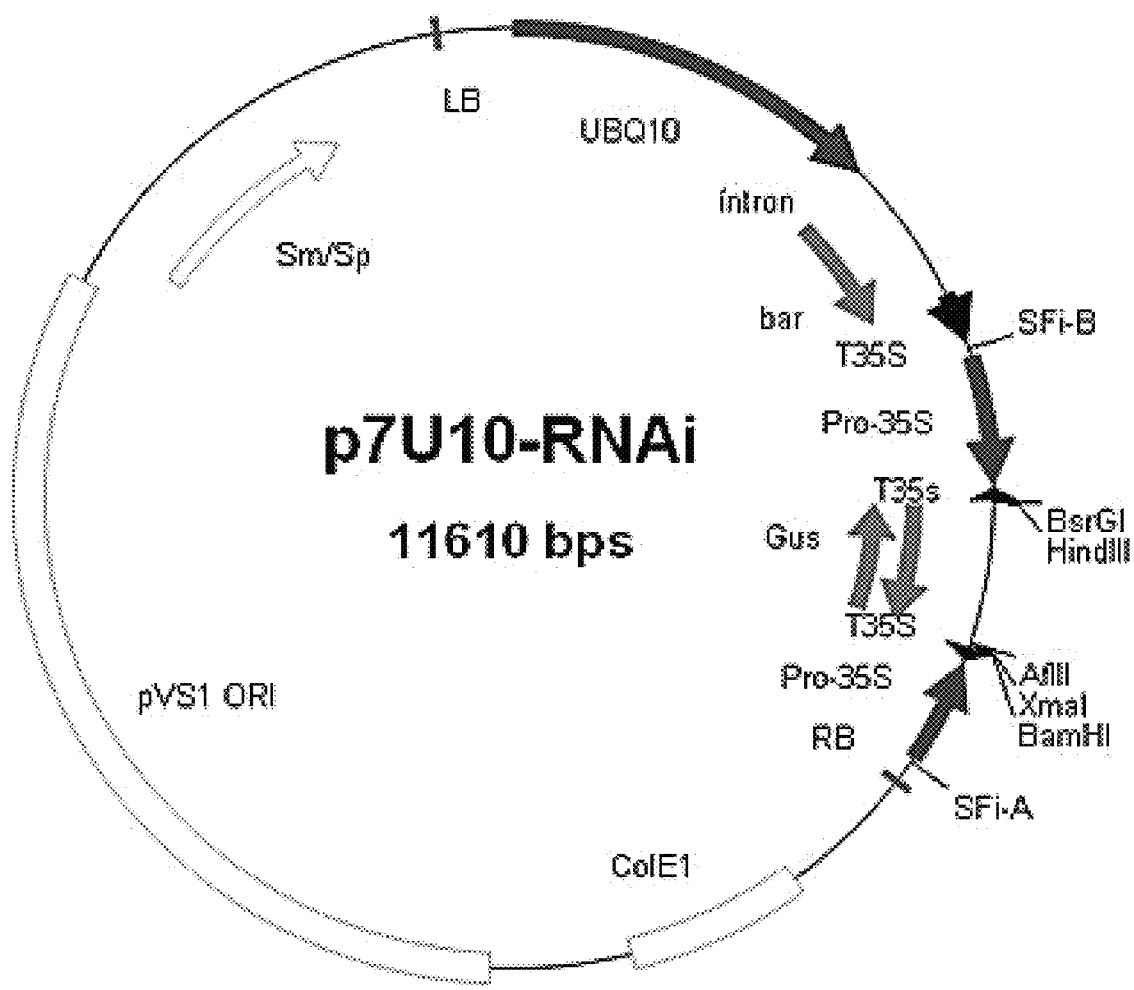

At 3 days post inoculation (dpi), both wild-type (wt) Col-0 and the ev control line showed water-soaked lesions with chlorotic or necrotic lesions; these are typical symptoms of a Fg infestation (FIG. 3a,i-ii). In marked contrast, four independent *Arabidopsis* T2 lines containing the CYP3RNA silencing construct (L1, L8, L10, L11) showed no disease symptoms, and their leaves were indistinguishable from those of the mock-inoculated controls (FIG. 3a,iii,iv). The percentage of infested leaf area on the four transgenic lines was 0.9%, whereas that of the ev controls was 77% (FIG. 3b). The CYP3RNA-expressing lines remained free of disease symptoms at 5 dpi, unlike the Col-0 ev plants which exhibited substantial symptoms at this time (FIG. 3c). The fungal hyphae are due to germination and growth of fungi in the inoculated agar, not on the leaf (FIG. 3b,ii). Furthermore fungal growth was slower and the colony pigment was yellow or brownish on plates with CYP3RNA-expressing lines rather than the typical pink on control plates (data not shown).

Fungal growth was characterized by microscopic analysis of detached leaves stained with trypan blue to visualize fungal hyphae as described above. On leaves from the Col-0 ev control, the fungal macroconidia germinated and developed mycelia within 3 dpi (data not shown). Profuse hyphal growth was seen outside and inside the leaf, and was not restricted to the inoculation site. Successful fungal development was further indicated by the formation of loose sporodochia formed by branched conidiophores. In marked contrast, fungal mycelium formation on CYP3RNA-expressing leaves was strongly (to nearly 100%) reduced and was exclusively confined to the wounded area surrounding the infection sites; no fungal colonization was detected in the surrounding leaf tissue. The fungus growing at the wound sites rapidly formed a vast number of sporodochia, which is indicative of the fungus being impaired by stress.

The results from the detached leaf assay were confirmed by confocal microscopy of intact leaves from Col-0 ev control and CYP3RNA-expressing plants inoculated with macroconidia of a green fluorescent protein (GFP)-expressing Fg strain. As evidenced by GFP fluorescence, Fg effectively colonized Col-0 ev control leaves, developing mycelia within 3 dpi. In comparison, fungal growth on CYP3RNA-expressing leaves was restricted to the inoculation site, where stress-induced sporulation was observed.

Strikingly, the level of resistance achieved by targeting all three paralogous Fg CYP51 genes for inducing HIGS was substantially greater than that observed in previously published HIGS studies.

Figure 12:
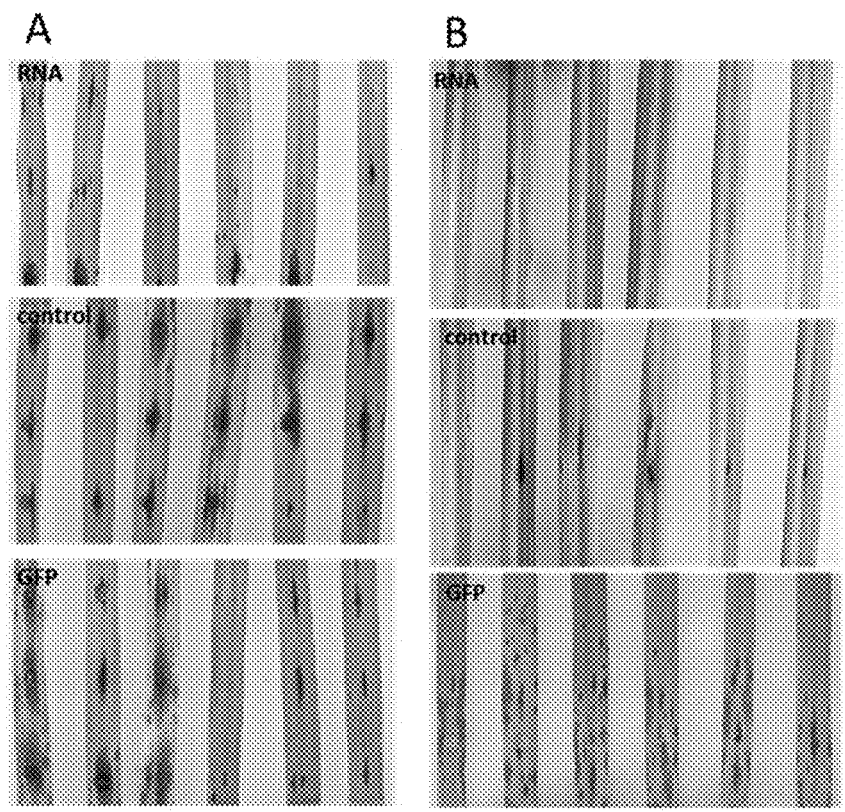
Figure 12:
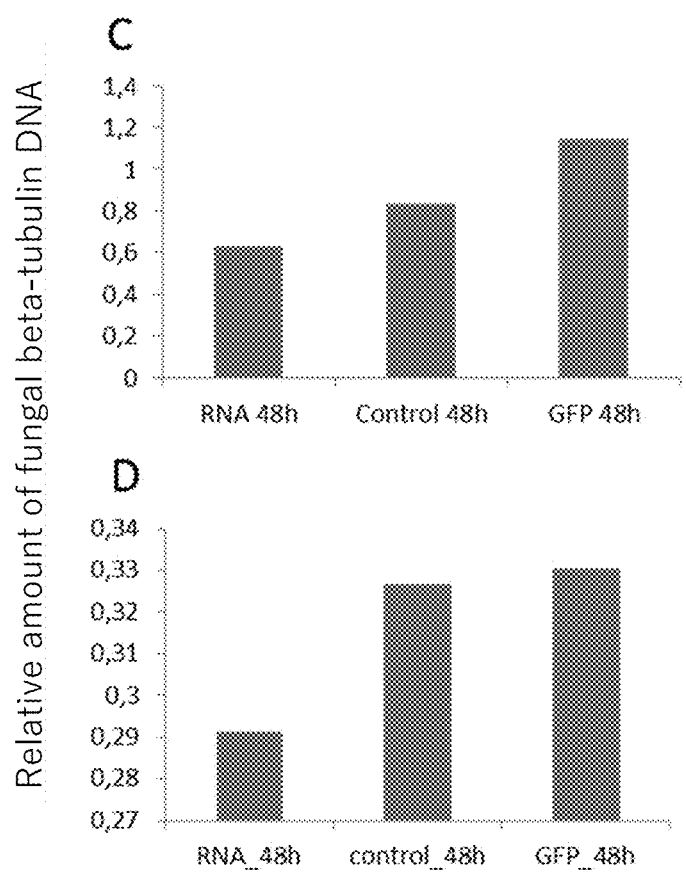

Example 3: Fg Resistance in the CYP3RNA-Expressing Lines is Due to HIGS of the CYP51 Genes To assess whether HIGS of the CYP51 genes was responsible for Fg resistance in the CYP3RNA-expressing lines, quantitative RT-PCR analysis of total RNA from the Fg inoculated leaves of CYP3RNA-expressing and ev control plants was performed 3 dpi (cf. method (vi) above). The relative transcript levels of Fg CYP51A, Fg CYP51B and Fg CYP51C were reduced on average by 92%, 89%, and 77%, respectively, in samples from CYP3RNA-expressing lines (L1, L8, L10, and L11), as compared with the ev control line (FIGS. 5-7).

It was further assessed whether this reduction in Fg CYP51 transcripts was associated with the production of corresponding siRNAs. In Northern analyses using CYP3RNA as the probe, siRNAs corresponding to the targeted CYP51 sequences in both Fg-infested and uninfested leaves from CYP3RNA-expressing plants were detected (FIG. 8). By contrast, these siRNAs were not observed in the leaves of wt or ev control plants. Taken together, these results suggest that expression of CYP3RNA in planta effectively silences the three Fg CYP51 genes, possibly by directing the host plant's silencing machinery to produce the corresponding siRNAs.

Example 4: Fg Resistance in CYP3RNA-Expressing Barley Leaves

Barley was transformed with p7i-Ubi-CYP3RNAi (FIG. 9). p7i-Ubi-CYP3RNA was generated analogous to p7U10-CYP3RNAi by replacing the GUS-fragment in p7i-Ubi-RNAi2 (FIG. 8) by a CYP51ABC fragment (CYP51A-CYP51B-CYP51C) using HindIII/XmaI restriction enzymes. The binary vector p7i-Ubi-CYP3RNAi contains two inverted 35S promoters that drive the constitutive production of sense and antisense copies of CYP51ABC. For preparing control plants, barley was transformed with the empty vector (ev) (FIG. 8). Transgenic barley plants expressing CYP51ABC were identified by RT-PCR using gene specific primers. For each transgenic line (L2 to L9, L15 and L42) and control plants (empty vector and wildtype cv. Golden Promise) two leaves of two-week-old barley plants were detached and transferred to square petri plates containing 2% agar/water. Each leaf was inoculated at three different spots (top, middle, bottom) with 20 µl drops of a suspension comprising $5\times10^4$ Fg macroconidia per ml. After 7 days, images of the leaves were taken (cf. FIG. 10) and the relative levels of CYP51A, CYP51B and CYP51C transcripts was determined analogous to method (vi) above (cf. FIG. 11). The leaves from transgenic lines (L2-L9, L14, L42) differed significantly from the leaves of the controls (ev, GP) with regard to symptoms of fungal infestation. Four of the 10 transgenic lines (L2, L7, L9, L42) exhibited no symptoms of fungal infestation (100% resistance). The remaining six lines (L3-L6, L8 and L14) showed only weak, locally restricted symptoms. In contrast, the control lines showed significant discoloration and bleaching of the Fg inoculated leaves (cf. FIG. 10).

Example 5: Reduction of Fg Growth after Application of dsRNA on Leaves

A 791 bp dsRNA (CYP3RNA) complementary to all three fungal CYP51 genes (FIG. 5) was generated and applied to detached barley leaves mounted on agar plates. As negative controls, only buffer or an unrelated dsRNA molecule (GFP-dsRNA, which has no significant homology to fungal genes) were applied. 48 h after spraying the barley leaves with CYP3RNA dsRNA or the negative controls, the leaves were infected with Fg macroconidia. 6 days after inoculation (i.e. 8 days after spraying), a significant inhibition of fungal growth was observed with CYP3RNA-treated leaves ("dsRNA") compared to the control leaves (which were sprayed with either buffer only ("control") or GFP-dsRNA ("GFP"), FIG. 12A). These findings were consistent with the results of qPCR, where the relative amount of fungal DNA in infected CYP3RNA-treated leaves was found to be significantly lower than in infected control leaves (FIG. 12C). Neither the TE-buffer nor the unrelated GFP-dsRNA had an inhibitory effect on fungal growth.

Example 6: Reduction of Fg Growth after Application of Application of RNA on Distal Leave Areas The upper part of the leaves were sprayed with dsRNA (CYP3RNA) or a control sample (buffer only ("control") or GFP-dsRNA ("GFP")), while the middle and lower areas were covered. After 2 days, the lower part of the leaves was subjected to fungal inoculation. The infection severity was determined 6 days after inoculation by measuring relative amount of fungal DNA. Fungal growth inhibition compared to the control-treated leaves was observed not only at the CYP3RNA-treated upper leaf area but also at the lower leaf area of the same leaf (FIGS. 12B and 12D). These findings indicate that CYP3RNA dsRNA is taken up by and transported within the leaf so as to provide a systemic protection from fungal infestation.

The invention claimed is:

1. A dsRNA molecule for inhibiting the expression of the CYP51A gene, the CYP51B gene and the CYP51C gene from *Fusarium graminearum*, the dsRNA comprising:
   i. a sense sequence being at least 90% identical to at least 50 contiguous nucleotides and having 100% sequence identity to at least 20 contiguous nucleotides of the coding sequence of the CYP51A gene set forth in SEQ ID NO: 1;
   ii. a sense sequence being at least 90% identical to at least 50 contiguous nucleotides and having 100% sequence identity to at least 20 contiguous nucleotides of the coding sequence of the CYP51B gene set forth in SEQ ID NO: 2;
   iii. a sense sequence being at least 90% identical to at least 50 contiguous nucleotides and having 100% sequence identity to at least 20 contiguous nucleotides of the coding sequence of the CYP51C gene set forth in SEQ ID NO: 3; and
   iv. antisense sequences being complementary to each of the sense sequences (i), (ii), and (iii);
   wherein the arrangement of the sequences within the dsRNA molecule allows hybridization of each sense sequence with its complementary antisense sequence.

2. The dsRNA molecule of claim 1, wherein
   the sense sequence (i) is at least 90% identical to at least 50 contiguous nucleotides of SEQ ID NO:4;
   the sense sequence (ii) is at least 90% identical to at least 50 contiguous nucleotides of SEQ ID NO:5; and
   the sense sequence (iii) is at least 90% identical to at least 50 contiguous nucleotides of SEQ ID NO:6.

3. The dsRNA molecule of claim 1 comprising a sense sequence that is at least 90% identical to SEQ ID NO:7, and an antisense sequence being complementary to said sense sequence, wherein the arrangement of the sequences within the dsRNA molecule allows hybridization of said sense sequence with said antisense sequence.

4. The dsRNA molecule of claim 1, wherein the sequence identity of each sense sequence pertains to at least 100 contiguous nucleotides of its respective reference sequence.

5. The dsRNA molecule of claim 1, wherein the sequence identity of each sense sequence to its respective reference sequence is at least 95%.

6. The dsRNA molecule of claim 1, wherein each sense sequence is located on a different RNA strand of the dsRNA molecule than its corresponding antisense sequence.

7. The dsRNA molecule of claim 1, wherein the sense sequences and the antisense sequences are located on a single RNA strand that loops back on itself so as to form a hairpin structure.

8. A DNA sequence or multitude of DNA sequences providing a transcriptional template of at least the antisense sequences of the dsRNA molecule of claim 1.

9. The DNA sequence(s) of claim 8 providing a transcriptional template of said dsRNA molecule.

10. The DNA sequence(s) of claim 9, wherein the transcriptional template is operably linked to at least one promoter.

11. The DNA sequence(s) of claim 10, wherein the at least one promoter is functional in a plant cell.

12. An isolated polynucleotide comprising a DNA sequence or a multitude of isolated polynucleotides comprising a multitude of DNA sequences, wherein the DNA sequence(s) provide(s) a transcriptional template of at least the antisense sequences of the dsRNA molecule of claim 1.

13. A transgenic plant comprising the DNA sequence(s) of claim 8 or the polynucleotide(s) of claim 12.

14. The transgenic plant of claim 13, wherein the plant is capable of generating at least the antisense sequences of said dsRNA molecule.

15. The transgenic plant of claim 14, wherein the plant is capable of generating said dsRNA molecule.

16. The transgenic plant of claim 13, wherein the transgenic plant is a cereal crop.

17. A method for controlling a fungal phytopathogen, wherein a transgenic plant according to claim 13 is cultivated to allow the generation of RNA comprising the antisense sequence(s) of said dsRNA molecule, and said RNA inhibits the growth and/or propagation of said phytopathogen.

18. A composition for controlling a fungal phytopathogen comprising the dsRNA molecule of claim 1, and a plant-compatible carrier.

19. A method for controlling a fungal phytopathogen, wherein a plant infested by or at risk of being infested by said phytopathogen and/or the vicinity of said plant is contacted with an effective amount of the composition of claim 18.

20. The isolated polynucleotide(s) of claim 12, wherein the DNA sequence(s) provide(s) a transcriptional template of said dsRNA molecule.

21. The isolated polynucleotide(s) of claim 20, wherein the transcriptional template is operably linked to at least one promoter.

22. The isolated polynucleotide(s) of claim 21, wherein the at least one promoter is functional in a plant cell.

23. The dsRNA molecule of claim 1, wherein at least one of said sense sequences is 100% identical to at least 25 contiguous nucleotides of at least one of SEQ ID NO. 1, 2, or 3.

24. The dsRNA molecule of claim 23, wherein all three of the sense sequences are 100% identical to at least 25 contiguous nucleotides of SEQ ID NOs. 1, 2, and 3.

* * * * *

SEQUENCE LISTING

<160> NUMBER OF SEQ ID NOS: 49

<210> SEQ ID NO 1
<211> LENGTH: 1524
<212> TYPE: DNA
<213> ORGANISM: Fusarium graminearum

<400> SEQUENCE: 1
atgttccatc tactcatcta tcccttatgg gtcttggtag cactctttgc tgtcataatt 60
gccaacctat tgtatcagca gcttcctcga aggccggacg agcctccact agttttccac 120
tggttccctt tctttggaaa cgcagtcgct tacggcctgg acccttgtgg cttctttgag 180
aagtgccgag agaagcacgg agacgtcttc acctttatct tattcggtcg aaaaatcgtc 240
gcttgccttg gcgtcgacgg caatgatttt gttctcaaca gtcgcctcca ggatgccaat 300
gcagaagaag tttacggtcc attgacaatc cccgtctttg gtagcgatgt cgtatacgat 360
tgtcccaact cgaagctcat ggaacaaaag aagtttgtca agtttggcct tacgcaaaaa 420
gcactcgagt cacacgtcca gttaatcgag cgagaggttc ttgactacgt cgaaactgat 480
ccatcctttt ctggcagaac tagcaccatc gatgtcccca aggcaatggc tgagataaca 540
atctttactg cctcacgttc tttgcagggt gaggaagttc ggagaaaact cactgccgag 600
tttgctgctc tgtatcacga tcttgacctt ggatttagac ctgtcaactt tctgtttcca 660
tggttgccac tgcctcacaa ccgaaaacga gatgctgctc atataaagat gcgggaagtc 720
tatatggata tcatcaacga tcgaagaaaa gggggcattc gaacagaaga tggtactgat 780
atgatagcca acttgatggg ctgcacttac aagaacggac agcctgttcc tgacaaggaa 840
atcgcccaca tgatgattac tctactcatg gcaggccagc actcttcatc ttctgccagt 900
tcttggatcg tgctgcacct tgcttcttct cccgacatta ccgaagaact ctaccaggag 960
cagctcgtaa atttgagcgt taacggtgct ctacctcccc ttcagtactc tgaccttgac 1020
aagctccctc ttctccagaa cgtcgtcaag gagactctcc gcgtccactc ttccatccac 1080
tcaatcctgc ggaaagtcaa gagacccatg caagttccca attcccctta cacgatcact 1140
acagacaaag tcatcatggc ttcacctaca gttaccgcga tgagtgaaga gtacttcgag 1200
aacgccaaaa catggaaccc tcatcgatgg gacaacagag caaaggagga ggttgacact 1260
gaagatgtca tcgactatgg atatggggct gtgtctaaag gaacgaagag cccgtacttg 1320
ccctttggtg ccggtagaca tcgctgcatt ggagagaagt ttgcctatgt caacttgggt 1380
gtcattgttg ctactttggt gcgcaacttc agactttcga ccattgatgg aagacctgga 1440
gtcccagaga cagactatac ttctttgttc tcacgacccg cccagcctgc gtttattcga 1500
tgggagcgta ggaagaagat atag 1524

<210> SEQ ID NO 2

```
<211> LENGTH: 1581
<212> TYPE: DNA
<213> ORGANISM: Fusarium graminearum

<400> SEQUENCE: 2
atgggtctcc ttcaagaact ggcgggccat ccgctcgccc aacaattcca ggaacttccc      60
ctgggccagc aagttggaat tggctttgca gtcttcctcg tgctctccgt cgtcctcaat     120
gtcctcaacc agctcctctt ccgaaacccc aatgagcccc ctatggtctt ccactggttc     180
ccctttgttg aagcaccat cacatacgga atggacccc ccacgttctt cagagagaac       240
cgtgccaagc acggcgatgt cttcaccttt atcctcctcg gaaagaaaac cactgtcgct     300
gttggccctg ctggaaacga cttcatcctc aacggcaagc tcaaggatgt gtgtgctgag     360
gagatctaca ccgttctcac tactcctgtc tttggcaagg atgtcgtcta tgactgcccc     420
aacgccaagc tcatgaaaca agaagaagttc atgaagattg ccctgaccac cgaagccttc     480
cgatcctacg ttcccatcat ctcctccgag gttcgcgatt acttcaagag aagccccgac     540
ttcaagggca agtctggcat tgccgatatc cccaagaaga tggccgagat cactatcttt     600
actgcttccc atgctctcca gggcagcgcc atccgcagca gtttgacga gtccctggcc      660 gctctctacc acgacctcga tatgggcttc accccatca acttcatgct tcactgggcc      720 cctctccct ggaaccgtaa gcgcgaccac gcccagcgca ctgttgccaa gatctacatg      780
gacactatca aggagcgccg cgccaagggc aacaacgaat ccgagcatga catgatgaag     840
caccttatga actctacata caagaacggt atccgtgtcc ctgaccacga ggttgcccac     900
atgatgattg ccctccttat ggctggccag cactcttctt cttccaccag ctcatggatc     960
atgctccgtc tcgctcagta ccctcacatc atggaagagc tctaccagga gcaggtcaag   1020
aacctcggtg ctgatctgcc tcctctgact tacgaagacc ttgccaagct gcccccttaac  1080 caggctatcg tcaaggagac ccttcgtctc catgctccta ccactccat catgcgcgcc    1140 gtcaagtctc ccatgcccgt ccctggcact aagtatgtca ttcccacttc gcacactctt   1200
ctcgctgctc ctggtgtcag tgctaccgac tctgccttct tccccaaccc tgatgagtgg   1260
gaccctcacc gatgggaggc agactctccc aacttccccc gcatggcttc caagggcgag   1320
gacgaggaga agatcgacta cggttacggc cttgtcagca agggttcagc ttctccctac    1380
ctgcctttcg gcgctggccg tcaccgatgc attggtgagc actttgccaa cgcccagctt   1440
caaaccattg ttgccgaggt tgttcgcgag ttcaagttcc gcaacgttga tggcggtcac   1500
accctgatcg ataccgacta cgcctcgctc ttctcccgac ctctggagcc cgccaacatt   1560
cactgggagc gacgccagta a                                              1581

<210> SEQ ID NO 3
<211> LENGTH: 1554
<212> TYPE: DNA
<213> ORGANISM: Fusarium graminearum

<400> SEQUENCE: 3
atggaatcgc tctacgagac tctgcggact ctaccgctct cagtctcaat ccctctaaca      60
accagcatca tcatcatctt gtccatcgtc accaacgtgg tcaaacaatt atggtttccc     120
aacccacatc gtccaccccgt tgtattccat atcttccct tcattggaag caccgtacaa     180
tatggcatcg acccgtacgc tttttcttc gactgcagag ataaatacgg cgactgcttt     240
acctttattc tccttggcaa atcaacgact gtctttcttg gtcccaaggg caatgacttt     300
atcctcaacg gcaaacacgc cgatctcaac gccgaggacg tttatgggaa acttaccacg     360
```

```
cccgtgtttg gtgaggaggt tgtttatgac tgctccaatg ctcgtttcat ggaccaaaag    420
aggcttctca aacttggtct caccacagat tccttacggt gctacatccc aaagttcgtc    480
aaagaagtcg aagactatgt taaaaactcg ccatacttca agggtgacac aggaatcgtc    540
aacattacag aagtcatggc cgaaatcaca atctacacag catccggatc cctcctagga    600
aacgaagtcc gatctatgtt tgacagcaca ttcgccactc tctaccgcca tctagatgat    660
ggcttccaac ccattaattt cgtcatgcca ggtcttcccc tcccgcaaaa cttccgtcga    720
aaccatgctc gaaaggtaat ggagaagctt ttcagcgata ttatttccaa gcgtcgcgag    780
actggcaatc aaggcgacga gacggatatg atttggatgc ttatgaatgc acagtataag    840
gatggggaac tcttccgga tcaccatgct gcgcgtatgt tgattgctat cctgatgggt    900
ggccagcata atactgctgt tagtggtgct tggcttcttc tcaatctggc ccataagcct    960
catcttgttc aggaactgta cgaggaacag acccaggtcc ttggctcacc acaagagcct   1020
ctgacatggg agaacttaca gaaattaact ctcaacggcc aagtcatcaa ggaaactctc   1080
cgtcttcaca gtccaatcca ctccatcctc cgacaagtca aatcacccat gcgagtccct   1140
ggcactgaat gggtagtgcc accatcccac acactgcttt cgtctcccgg cacaatggcc   1200
cgctcagaag aattcttccc tcgaccatca gaatgggatc ctcatcgttg gacaagatt    1260 gaacctctcg tgaagaccgc cgaagatggt caaacagtgg attacggttt tggggtgatg   1320
agcaaatccg tcagcagtcc ttatttgccc tttggagctg gacgacatcg atgtgttggc   1380
gagaattacg cttatgcaca gctgggagct attgttgcca cgtttatcag attggttcac   1440
attgaacagc ctgacccgaa ggctcctctt ccggcaccag attattcttc catgttttct   1500
cggcccatga accctgccga gatccgatgg cgtcgacgcg agacagtaga atga         1554

<210> SEQ ID NO 4
<211> LENGTH: 294
<212> TYPE: DNA
<213> ORGANISM: Fusarium graminearum

<400> SEQUENCE: 4
cggtccattg acaatccccg tctttggtag cgatgtcgta tacgattgtc ccaactcgaa     60
gctcatggaa caaagaagt tgtcaagtt tggccttacg caaaaagcac tcgagtcaca    120
cgtccagtta atcgagcgag aggttcttga ctacgtcgaa actgatccat ccttttctgg    180
cagaactagc accatcgatg tccccaaggc aatggctgag ataacaatct ttactgcctc    240
acgttctttg cagggtgagg aagttcggag aaaactcact gccgagtttg ctgc          294

<210> SEQ ID NO 5
<211> LENGTH: 220
<212> TYPE: DNA
<213> ORGANISM: Fusarium graminearum

<400> SEQUENCE: 5
cagcaagttt gacgagtccc tggccgctct ctaccacgac ctcgatatgg gcttcacccc     60
catcaacttc atgcttcact gggcccctct cccctggaac cgtaagcgcg accacgccca    120
gcgcactgtt gccaagatct acatggacac tatcaaggag cgccgcgcca agggcaacaa    180
cgaatccgag catgacatga tgaagcacct tatgaactct                          220

<210> SEQ ID NO 6
<211> LENGTH: 238
<212> TYPE: DNA
```

-continued

<213> ORGANISM: Fusarium graminearum

<400> SEQUENCE: 6
attggaagca ccgtacaata tggcatcgac ccgtacgctt ttttcttcga ctgcagagat 60
aaatacggcg actgctttac ctttattctc cttggcaaat caacgactgt ctttcttggt 120
cccaagggca atgactttat cctcaacggc aaacacgccg atctcaacgc cgaggacgtt 180
tatgggaaac ttaccacgcc cgtgtttggt gaggaggttg tttatgactg ctccaatg 238

<210> SEQ ID NO 7
<211> LENGTH: 785
<212> TYPE: DNA
<213> ORGANISM: artificial sequence
<220> FEATURE:
<223> OTHER INFORMATION: combines partial sequences of Fusarium graminearum CYP51B-CYP51A-CYP51C

<400> SEQUENCE: 7
cagcaagttt gacgagtccc tggccgctct ctaccacgac ctcgatatgg gcttcacccc 60
catcaacttc atgcttcact gggcccctct cccctggaac cgtaagcgcg accacgccca 120
gcgcactgtt gccaagatct acatggacac tatcaaggag cgccgcgcca agggcaacaa 180
cgaatccgag catgacatga tgaagcacct tatgaactct ccatggcggc cgcgggaatt 240
cgatatcggt ccattgacaa tccccgtctt tggtagcgat gtcgtatacg attgtcccaa 300
ctcgaagctc atggaacaaa agaagtttgt caagtttggc cttacgcaaa aagcactcga 360
gtcacacgtc cagttaatcg agcgagaggt tcttgactac gtcgaaactg atccatcctt 420
ttctggcaga actagcacca tcgatgtccc caaggcaatg gctgagataa caatctttac 480
tgcctcacgt tctttgcagg gtgaggaagt tcggagaaaa ctcactgccg agtttgctgc 540
cactagtatt ggaagcaccg tacaatatgg catcgacccg tacgcttttt tcttcgactg 600
cagagataaa tacggcgact gctttacctt tattctcctt ggcaaatcaa cgactgtctt 660
tcttggtccc aagggcaatg actttatcct caacggcaaa cacgccgatc tcaacgccga 720
ggacgtttat gggaaactta ccacgcccgt gtttggtgag gaggttgttt atgactgctc 780
caatg 785

<210> SEQ ID NO 8
<211> LENGTH: 1521
<212> TYPE: DNA
<213> ORGANISM: Fusarium oxysporum

<400> SEQUENCE: 8
atgttctcac tcctatacta ccctctatgg gcctttgctt cctgcctagt tatcatcact 60
ctcaacgtct tataccagaa gctccctcga aatgccaacg aacctccgtt agtgttccac 120
tggcttccat tcgttgggaa tgctgttgct tatggactcg acccttatgg tttctttgtg 180
aagtgtcgag aaaagcacgg cgatgtcttc acctttatcc tcttcggtcg aaaaatcgtt 240
gcctgtcttg gtgttgacgg caatgacttt gttctcaaca gtcgaattca ggacgccaac 300
gccgaagaaa tctacagtcc attgacaacg cctgtctttg gtagtgatgt cgtatacgat 360
tgtcccaact cgaagctcat ggagcaaaag aagtttgtca agtttggcct tacacaaaag 420
gctctcgagt cccatgtcca gttgatcgag cgagaggttc tggagtacat ccaagctgta 480
ccttcattct ctggaaagtc tggcacagtt gatgtatcca aggcaatggc tgagataacc 540
atcttcactg ctgctcgctc tctgcagggc gaagaagttc gacggaagct tacagctgag 600

| | |
|---|---|
| tttgcagctc tgtatcatga ccttgaccta ggcttcactc ctgtaaactt cctgttcccc | 660 |
| tggctacctt tgcctcataa ccgacgtcga gatgctgctc atgcaaagat gagagagatc | 720 |
| tacatggaca tcattaacgg acgaagaaga ggcgtagggg acttggagaa aggaactgac | 780 |
| atgatcgcca acctgatgaa ttgcgagtac aaaaacgggc agccgattcc ggacaaagag | 840 |
| atcgcgcaca tgatgatcac ccttctcatg gctggacaac actcttcgtc atctgctagt | 900 |
| tcatggatca tactacatct ggcttcatcc actgacattg ctgaggaact ctaccaagag | 960 |
| caactcatta acttgagtgc tgatggtgtt ctccctcccc ttcagtacac cgacctcgac | 1020 |
| aagcttcccc ttcttcagaa tgtcgtcaaa gaaacactcc gtgttcattc ttccattcac | 1080 |
| tccattctgc gaaaggttaa agagacctatg caagcacctg gatcaccttta caccatcacc | 1140 |
| acagacaagg ttctcctcgc ttcaccaact gttacagcgt tgagtgaaga cacttcacg | 1200 |
| gacgcccaga gatggaatcc tcatcggtgg ataacaaac cccaggagga ggccgtgacg | 1260 |
| gacgatgtca ttgactacgg ctacggcgct gtttctaaag gaacgaagag cccatactta | 1320 |
| ccctttggcg ctggtcggca tcgctgcatc ggggagaagt ttgcttatgt caacttgggc | 1380 |
| gttatcgtcg cgactttggt gcgcaacttc agactgtcga ctcttgatgg caagcctggt | 1440 |
| attccagcaa ctgactacac ttctctcttc tcaaggccag cccaacctgc atacataaac | 1500 |
| tgggagcgca ggagggctta a | 1521 |

<210> SEQ ID NO 9
<211> LENGTH: 1584
<212> TYPE: DNA
<213> ORGANISM: Fusarium oxysporum

<400> SEQUENCE: 9

| | |
|---|---|
| atgggtctcc tccaagaact tgcgagccac ccgctcgcac aacaatatca ggagctcccc | 60 |
| ctgggccagc agattggaat tggcttcgga gcattcataa ttctctctgt cgttctgaat | 120 |
| gtgctcaacc agctactctt caagaaccgc aatgaacctc ccctagtctt ccactggttc | 180 |
| cctttcgttg aagcactat cacatacgga atggaccccc ctaagttctt caaggagaac | 240 |
| cgcgccaagc atggtgatgt tttcaccttt gtcctccttg gaaagaaaac cactgtcgct | 300 |
| gttggcccca ctggaaacga cttcatcctc aacggaaagc tcaaggatgt ctctgccgag | 360 |
| gagatttaca ctgttctcac tactcctgtc tttggcaagg atgtcgtgta cgattgccct | 420 |
| aatgccaaac tcatggagca agaagttc atgaaaatcg ccctcacgac cgaagccttc | 480 |
| cgatcatacg tgcctattat ctccgccgag gttcgcgatt acttcaagaa gagccctgat | 540 |
| ttcaagggca gtccggtat tgtcgatatt cccaagaaaa tggccgagat cactatcttc | 600 |
| actgcttcgc atgcccttca gggcagcgtc attcgtaaca agtttgacga gtctctggcc | 660 |
| gctctctacc acgatctcga catgggtttc actcccatca acttcatgct tcactgggct | 720 |
| cctctcccct ggaaccgcaa gcgtgaccac gcccagcgca ctgttgccaa gatctatatg | 780 |
| gacaccatta aggagcgacg cgctaaggac aacgatgaca ccgagcacga tatgatgaag | 840 |
| catctcatga actctactta caagaacggc accctgtcc ctgatcatga ggtcgcccac | 900 |
| atgatgattg ctctcctcat ggctggccag cactcttctt cttctaccag ctcttggatc | 960 |
| atgctccgtc tcgctcagta ccctcacatc atggaggagc tgtaccaaga gcaggtcaga | 1020 |
| gaactcggtg ctgatttgcc tccccctgact tacgacaacc ttgccaagct gcccctcaac | 1080 |
| caggccatta tcaaggagac tctccgcctt cacgcccta tccactctat catgcgcgcc | 1140 |
| gtcaagtctc ccatgcctgt ccctggaacc aagtacacca tcccgacctc gcacactctt | 1200 | ctcgccgccc ccggtgtcag cgctactgac tcggcctact tccccaaccc cgatgagtgg 1260 gatcctcacc gatgggaggt cgactctccc aacttcccca gaatggctac ccgtggcgat 1320 gacgaagaga agatcgacta tggctacggc cttgtcagca agggttccgc ctctccttat 1380 ctgccctttg gtgctggtcg tcaccgatgc attggcgagc actttgccaa cgcccagctt 1440 cagacaattg ttgctgaggt tgtgcgtgag ttcaagttcc gcaatgtgga tggcggcaac 1500 actctaatcg acaccgacta cgcctcgctt ttctcgcgac ccttggagcc cgccaacatt 1560 cactgggaga gacgccagca gtag 1584

<210> SEQ ID NO 10
<211> LENGTH: 1149
<212> TYPE: DNA
<213> ORGANISM: Fusarium oxysporum

<400> SEQUENCE: 10
atggatcaga agaggcttct caaacttggt ctcacaactg actcattgcg atgctacatc 60
cccaaattcg tcaaagaagt cgaagaatac atcgctactt caccctactt caaaggatca 120
actggcatcg tcaacatcac cgaagtaatg gccgagatca caatctacac cgcagcaggc 180
tccctcctcg gtaacgaagt ccgctccatg tttgacagca cattcgcaac cctgtaccgc 240
catctcgacg atggctttca acctatcaac ttcgtcatgc ctggtcttcc cctaccacaa 300
aacttccgtc gcgatcacgc acgaaaggtc atggaggaat tgttcagcga catcatccgc 360
aagcgtcgtg agattggaaa tcaaggcggt gagactgata tggtttggac gcttatgaat 420
gctaaataca aggatggtga ggacttgccg gatcatcatg cggcgaggat gttgattgct 480
attctgatgg gtgggcagca caacactgct gctagtggcg cctggctact tctcaatctt 540
gcgcataaac cgcatctcgt tcaagagttg tatgatgagc agcttgaggt tttgggatca 600
ccgcaagagc cgttgacgtg ggagaatttg cagaagttga cgctgaatgg acaggttatc 660
aaggagacct tgcgtcttca cagtccaatc cactctattc tccgacaggt caagtcacct 720
atgcgagttc ccggcacaga ctgggttgtt ccgccgtctc atacactcct cgcttctccc 780
ggtacacaag cacgatctga ggaattcttt cctagaccta tggaatggga tcctcatcgg 840
tgggataaaa ttgagtctct tgaggactcg aagggtaatg gggagacagt tgattatggc 900
ttcggcgtga tgaacaagtc tgtgagcagc ccatatctac cctttggcgc gggacggcat 960
cgctgtgttg gagagaacta cgcgtatgcc cagttgggcg ccatcattgc aacgtttgtg 1020
agactgcttc atattgaaca gcctgatccc aatgcacctc tacctgcgcc tgactattcg 1080
tcaatgtttt ctcggcctat gaacccagcc gtcatccgat ggactcgtcg taacacggag 1140
gccaattag 1149

<210> SEQ ID NO 11
<211> LENGTH: 1338
<212> TYPE: DNA
<213> ORGANISM: Fusarium verticillioides

<400> SEQUENCE: 11
atggagctgg tgcacggcga tgtcttcacc tttgtcctct tcggtcgaaa gatcgttgcc 60
tgtcttggtg ttgatggcaa tgactttgtt ctcaacagtc gaattcaaga cgccaacgcc 120
gaagaaatct acgggccatt gacaacgcct gtctttggca gcgatgtcgt atacgattgt 180
ccaaactcaa agctcatgga gcaaaaaaag tttgtcaagt ttggtcttac ccaaaaggct 240

| | |
|---|---|
| cttgagtccc atgttcagtt gatcgaacga gaggttttag agtacatcca agcagtacct | 300 |
| tcattctctg agaagtctgg cacagttgat gtatccaaag cgatggctga gatcaccatc | 360 |
| tttactgctg cccgttctct gcaaggtgaa gaagttcgac ggaagcttac cgctgagttt | 420 |
| gcagctctgt atcatgacct cgatctaggc tttactccgg tcaacttcct gttcccctgg | 480 |
| ctacctctgc ctcacaaccg acgtcgagac gctgctcatt caaagatgag agagatctat | 540 |
| atgggcatta tcaatgaacg aagaagaggc ggaggagact tggaaaaaag aaccgatatg | 600 |
| atcgccaact tgatgagttg tgcctacaag aacaggcagc ccattcctga caaggagatc | 660 |
| gcacacatga tgatcactct tctcatggcc ggacaacact cttcatcatc tgctagttca | 720 |
| tggatcgtac tgcatctggc ttcatcccct gatatcactg aggaactcta ccaagagcaa | 780 |
| gtcatcaact tgagtgctag cggcgctctc ccaccccctgc agtactccga cctcgacaag | 840 |
| ctcccgcttc tccagaatgt tgtcaaagaa acactccgag ttcattcttc tatccactct | 900 |
| attctgcgaa aggtcaagag acccatgcaa gcacctggcc caccttacac catcaccacc | 960 |
| gacaaggtta tcctcgcttc accaactgtt acagcgttga gtgaagaaca cttcccagac | 1020 |
| gcccaaagat ggaatcctca tcggtgggat aataagcccc aggaggaggc cgtgacggac | 1080 |
| gaagtcattg actacggcta cggtgctgtc tctaaaggaa caaaaagccc atatttaccc | 1140 |
| tttggtgcgg gccggcatcg atgtatcgga gagaagtatg cttatgtcaa cttaggagtt | 1200 |
| atcgtcgcga cgttggtgcg taacttcaga ctgtcgactc ttgatggcaa gcctggtgtt | 1260 |
| ccagcaaccg acttcacttc tctcttctcg agaccagccc aacctgccta catcaaatgg | 1320 |
| gaacgcagga aggcttag | 1338 |

<210> SEQ ID NO 12
<211> LENGTH: 1584
<212> TYPE: DNA
<213> ORGANISM: Fusarium verticillioides

<400> SEQUENCE: 12

| | |
|---|---|
| atgggtctcc tccaagaact tgcgagccac ccgctcgcac aacaatatca ggagcttccc | 60 |
| ctggcccagc aaattggaat tggctttgga gctttcgtag ttctctctgt cgttctcaat | 120 |
| gtactcaacc agctactctt caagaaccgc aatgaaccac ccctggtctt ccactggttc | 180 |
| cccttcgttg gaagcactat cacatacgga atggaccccc ctaaattctt cagggagaac | 240 |
| cgtgccaagc atggtgatgt cttcaccttt gtcctcctcg gaaagaaaac cactgtcgct | 300 |
| gttggcccca ctggaaacga cttcatcctc aacggaaagc tcaaggatgt atctgccgag | 360 |
| gagatttaca ctgttctcac tactcctgtc ttcggcaagg atgtcgtgta tgattgcccc | 420 |
| aatgccaaac tcatggagca gaagaagttc atgaaaatcg ccctcacgac cgaagccttc | 480 |
| cgatcatatg tgcctattat ctcctccgag gttcgcgatt acttcaagaa gagccccgat | 540 |
| ttcaagggca gtccggtat tgtcgacatt cccaagaaaa tggccgagat cactatcttc | 600 |
| actgcctcgc atgccctcca aggcagcgtt atccgtaaca agtttgacga gtctctggcc | 660 |
| gctctctacc acgatctcga catgggtttc actcccatca actttatgct tcactgggct | 720 |
| cctctgccct ggaaccgcaa gcgcgatcac gcccagcgca ctgttgccaa gatctatatg | 780 |
| gacaccatta aggagcgacg cgctaaggac aacgatgaca ccgagcacga tatgatgaag | 840 |
| catctcatga actctactta caagaacggc accctgtcc ctgatcacga ggtcgcccac | 900 |
| atgatgattg ctcttctcat ggctggccag cactcttctt cttctaccag ctcttggatt | 960 |
| atgctccgtc tcgctcagta ccctcacatc atggaagagc tgtaccaaga gcaggttaga | 1020 |

```
gagctcggtg ctgatttgcc tcccctgact tacgacgacc ttgccaagct gcccctcaac    1080
caggccatta tcaaggagac tctccgcctt cacgctccta ttcactccat catgcgcgcc    1140
gtcaagtctc ccatgcctgt tcctggaacc aagtacacca tcccgacctc gcacactctt    1200
ctcgccgctc ctggtgtcag cgctaccgac tcggcctact tccccaaccc cgatgagtgg    1260
gatcctcacc gatgggaggc cgactctccc aacttcccca gaatggctaa ccgtggcgat    1320
gacgaagaga agatcgacta cggctacggt cttgtcagca agggttctgc ctctccttat    1380 ctgcccttttg gtgctggtcg tcaccgatgc attggcgagc actttgccaa cgcccagctt    1440
cagacaattg ttgctgaggt tgtgcgtgag ttcaagttcc gcaatgtgga tggcggcaac    1500
actctgatcg acaccgacta cgcctcgctt ttctcacgac ccttggagcc cgccaacatc    1560
cactgggaaa gacgacagca gtag                                           1584
```

<210> SEQ ID NO 13
<211> LENGTH: 1146
<212> TYPE: DNA
<213> ORGANISM: Fusarium verticillioides

<400> SEQUENCE: 13

```
atggatcaga gaggcttct taagctcggt ctcacgactg agtcgttgcg atgctacatc      60
cccaaattcg tcaaagaagt agaagactac atcgccacgt caccatactt caaaggtaac    120
accggaatcg tcaacatcac cgaagtaatg gccgagatca caatctacac tgcagcaggc    180
tccctcctcg gcaacgaagt ccgctccatg ttcgatagca cattcgcaac gctttaccga    240
catctcgacg atggtttcca gcccataaac ttcgtcatgc ctggtcttcc cttaccacag    300
aacttccgac gcgatcatgc gcgaaaggtc atggaagagc tttcagcga tatcattcgc      360 aagcgtcgtg agatgggcaa tcaaggtgat gagactgata tggtttggac gcttatgaat    420
gctaaataca aggatggtga ggatctgccg aatcatcatg ccgcgaggat gttgattgct    480
attcttatgg gtggacagca taacactgct gcgagtggtg cttggctact tctcaacctt    540
gcgcataaac cgcatctggt caaggaattg tatgacgaac aagttgaggt tttgggatca    600
ccgcaggagc ccttgacgtg ggagaattta cagaaattga ccctcaatgg acaggtcatc    660
aaggaaactc tacgtcttca cagtccaatt cattctattc tccggcaggt caaatcacct    720
atgcgagttc ccgcacagag ctgggtagtt cctccatctc atacacttct cgcttcacct    780
ggtacacaag ctcgatctga ggaattcttc cctcggccta tggaatggga tcctcatcga    840
tgggataaga tcgagtctct tgatgatgcc aagaatgggg agacagtcga ttatgggttc    900
ggtatgatga gcaagtccgt cagcagcccg tatctgcctt ttggtgcagg gcgacatcgt    960
tgtgttgggg agaactacgc atatgcacag cttggtgcga ttattgcatc gtttgtgaga   1020
ttgcttcata ttgagcagcc tgatcctaag gcacctcttc ctgcgccaga ttattcttca   1080
atgttttctc ggcctatgaa cccagccgtc atccgatgga ctcgccgtaa cgcggagact   1140
ggttag                                                              1146
```

<210> SEQ ID NO 14
<211> LENGTH: 1593
<212> TYPE: DNA
<213> ORGANISM: Blumeria graminis

<400> SEQUENCE: 14

```
atgggaatat cagaaagctt t

-continued

```
agcattgcgt tggctagtgg aattataagt ttattattac tattaacctt cttgaatgta    120
ttgaagcagc tactattcaa aaatccaaat gagccaccga tcgtgtttca ttggattcct    180
atcattggta gtacaatttc atatggaatg aatccctata aattctttca tgaatcccaa    240
gccaagtacg gaaatatttt cactttcata ttactgggta aaaagacgac agtatatcta    300
ggtcgacagg gaaacaattt tattcttaat ggaaaactga gggatgttaa tgctgaagaa    360
gtttattcag tcttaacgac tcctgtcttc gggactgatg tagtgtatga ctgtcctaat    420
tcaaaattaa tggaacaaaa aagttcatg aaagcagccc ttacaactga ggccttccgc    480
tcttatgtac ctatcatcca aaatgaagtg gagagcttta taaataaatg cgacgatttt    540
cgaaaatcag aaggtatcat caatatcgct gccgtaatgg ctgaaattac gatatatacc    600
gcttcacaca ccctacaagg aaaagaggtt cgcgatagat ttgattcttc tttggcagtt    660
ttgtatcatg acctagatat gggctttacc ccaatcaatt tcatgcttca ctgggcacca    720
cttccgcaca atcgagctcg tgatcatgcc aacggacag tcgcaaaaat atacatggag    780
attatcaaca gccgtcggac gcagaaagaa actgataatt ccaatttaga tatcatgtgg    840
caattaatgc gctcttccta caaagatggc actcccgtac cggataaaga aattgcacat    900
atgatgatcc gctcctgat ggctgggcaa cattcttcgt cctcgtccag cacatggatc    960
atgctgtggc ttgctgctcg accagatatc actgaagaac tctaccaaga acagctagaa   1020
atattgggat cagaattacc tcctgctaaa tatgaagatc tctcgaaact tactctgcat   1080
caaaatgtag tgaaagaggt cctccgtctg catgctccca tacattcgat cttacgaaaa   1140
gtaaagaatc caatgcccgt tccaggaact agttatgtaa tacctaagac caattctctc   1200
ttggcggccc ctgggtggac aagtcgagac gcctcatact tccctaatcc gcttacgtgg   1260
gacccacatc gttgggacac tggatctagt ggggtgatag gcacggatat ggaggatgaa   1320
aaattcgact atgggtatgg attaattagc acaggggcag caagcccctta cttaccgttt   1380 ggggccggac ggcatcgctg cataggcgag cagtttgcaa cggtgcaatt agttacaatc   1440
atggccacca tggttcgcag tttcaagttt cacaaccttg acggaaggga gggcgttgcc   1500
gaaactgatt actcaagtat gttttctcgg ccaatggcac ctgccataat tgcatgggag   1560
aagagggaca aaaaggacaa aacgagtgt taa                                 1593
```

<210> SEQ ID NO 15
<211> LENGTH: 1581
<212> TYPE: DNA
<213> ORGANISM: Magnaporthe grisea

<400> SEQUENCE: 15

```
atgggccttc tacaggacac caccggcccg ctggtagatg ccttctacca gctgggcact     60
ggggcgcagg ttggtgttgc cttcgtcagc ttcatcttcc tctcggtctt tttccacgta    120
gcgcagcaga tcttcttcaa gaaccccat gagccgcccg tcgtcttcag ctggttcccc    180
gtcgtcggtt cgacggtcac gtatggaaag gacccgccac agttcttccg ggacatggcc    240
aagaagtacg gcaacatctt taccttcatt ctcctcggaa agaagacaac cgtctacatc    300
ggcaccgaag gcaacgagtt catcctcaac ggcaagctgc gcgatgtcaa tgcagaggag    360
atctacggac ccatgaccac tcccgtgttc ggcaaggacg tcgtctatga ctgccccaac    420
gccaagctga tggagcaaaa gaagtttatg aagatcgccc tcaccaccga ggccttccgt    480
tcttacgttc ctatcattgc cgacgaggtt tcgagctacc tgaagcggac ccccgccttc    540
aagggcccgt cgggcgtcgt caacatcccg cccaagatgg ccgagattac catcttcacc    600
```

-continued

```
gcctcgcacg ccctccaggg taaggagatc cgcgaccagt tcgacgagac cctggccgat      660
ttgtaccacg acctcgacat gggcttccac ccggtcaact tcaagcttca ctggctaccc      720
ctcccccgca acatccgccg cgacaaggca caaaagacca tcgccaagat ctacatggac      780
accatccagc gccgccgtgc gaagggtaag gactccgagg ccaaggatat gatgtaccac      840
cttatgaact cgacctacaa aaatggcacc cccgtccctg accacgagat cgcccacatg      900
atgatcgctc tcctgatggc cggacagcac tcgtcgtcgt ccaccagctc ctggatcatg      960
ctccgcctcg ccagccgccc ggatattatg gaggaactgt accaggagca ggtccgcgcg     1020
ctgggtgccg acttgccccc tctccgctac gaggacctcg ccaatctgcc tctccacctc     1080
gccgtcatca aggagactct ccgcctccac gctccgatca actccattct ccgcgccgtg     1140
aagcaggacc tccccgttcc gggtaccaac tacgtcatcg ccaaggacac caccgtcctc     1200
gccgcccccg gatactcggc cggtgacccc aaccacttcc ctgagccgga actttgggag     1260
ccgcaccgtt gggaggccga ctcgcgcctg gctccacgca tctcgatgag caacgacaac     1320
gatgaggagg agaagattga ttacggatac ggcctcgtca gcaagggtac tacctctcct     1380
tacttgccct ttggcgccgg tcgccaccgc tgcatcggtg aacacttcgc caacgtccag     1440
cttcagacca ttgtcgccat gattgtgcgc gagttcaagt ccgcaacgt cgacggcagc     1500 ggcaaggtcg tcggcaccaa ctacgcctcg ctcttctcca ggcctgagga gcccgccaaa     1560
atttactggg agaggcgcta a                                              1581

<210> SEQ ID NO 16
<211> LENGTH: 1548
<212> TYPE: DNA
<213> ORGANISM: Magnaporthe grisea

<400> SEQUENCE: 16
atggctttct tcttcccatc tgccccagtc tgggtttact cagccggcgc agccctactc       60
ttcatcattg gctccataat actcaacttc atctggcagc aactgccccg tcccaaatcg      120
gaaccaccgc tggttttcca ctggttgccc ttcatcggca cgccgtctc ctacggcatg       180 gacccctacc gcttctactc tcaatgccgg gaaaagcacg gcgatgtctt tacgtttgtc      240
ttgttcggca ggcgcatgac cgtcttctta ggcgtccagg gcaacgactt catcctgaac      300
ggcaagctgc aggacctcaa tgctgaggag atatacagcc ctctcaccac accagttttc      360
ggaagtgata ttatctacga ctgccccaac tccaaactca tggagcaaaa gaagtttgtc      420
aagtttggcc tgacgcaaaa ggctctggat tcctacgtcc cctgatcga gggaggtc        480 ctcgactaca tagagtcctc acccgtcttc caagccggca accacggcat cgtagacatt      540
cccagcatga tggccgagat aaccattttc acagccagtc gtaccttgca aggccccgag      600
gtcaggaaga agctgactgg agaattcgca cgactctatc acgacttgga cctgggtttc      660
cgccccatca acttcctagc cccgtgggcg ccccttcccc agaaccgccg acgcgacgtt      720
gctcatgctc gaatgcgcga tgtttacatg gacctcatca acaaacgccg ccgacagaag      780
gacgatcaag aagaagaaga agaagcgag ccagacatga tccgccacct gatgggcagc      840
tgcgtgtaca aaaacggcca agccctcccc gacaaggaaa tcgcccacat gatgatcacg      900
cttctcatgg caggccagca ttcttcctcc tcttcgagcg cgtggatcat gctccgcctc      960
gcgtcgcggc ccgacatcgc cgaggaggtg taccaagaag tgcagcggct cgggcacgca     1020
tccctgcagc actcggacct cgacaagctg ccgctgctcg caaacgtggt caaggagacg     1080
```

| | |
|---|---|
| ctgcgggtgc actcgtccat ccactccatc atgcgcaagg tgaagcggcc gatgcggatt | 1140 |
| ccggcagcg actacgtcgt caccccgggc aaggtgctcg tgtccgcgcc catcatgacg | 1200 |
| cacctggacg aggagcactt ccgcgacgcg cgggcttggg agccgcatcg gtgggatgac | 1260 |
| gccgtcgacg cccaggacga cgagattgtc gattacggct acggggccac gtccaagggc | 1320 |
| accaagagtc cttacctgcc cttggcgcc ggtcggcatc gctgcatcgg tgaaaagttt | 1380 |
| gcctatctca acctggcggc catcgtcagc accttggtcc ggaacttcaa gttctccacg | 1440 |
| ctggatggca aggccaccgt gccgcccact gattacactt ctatgttctc tcggcctatg | 1500 |
| cagcctgcga cggtgaggtg ggagcgacgc agcccgaaga ctgcgtag | 1548 |

<210> SEQ ID NO 17
<211> LENGTH: 1569
<212> TYPE: DNA
<213> ORGANISM: Sclerotinia sclerotinium

<400> SEQUENCE: 17

| | |
|---|---|
| atgggtattc tcgaaacaat tgccgggcca ttggctcaag agatttcgca aaggtcaacc | 60 |
| tttgctgttg ttgctgctgg cgtggcagca ttcgtcgttc tatctgtcat tctcaatgtc | 120 |
| ctgaatcaag tgttatttgc gaaccccaat gaaccaccag tggtcttcca ctggtttcca | 180 |
| atcattggta gcaccgtcac ttatggtatg daccccttata aattcttctt cgagtgtcgc | 240 |
| gcaaagtacg gtgatatttt cacatttgtc ttgctcggaa agaagaatac agtatatctt | 300 |
| ggacgaaatg gcaatgactt tattctcaat ggcaagctta aggatctcaa tgcggaggaa | 360 |
| atatatactg ttttgacaac tcccgtgttt ggaaaggatg tagtctacga ttgccccaat | 420 |
| gcgaaattga tggagcaaaa aaagttcatg aaaattggct tgtctactga agctttccga | 480 |
| tcctacgtcc caattataca aatggaagtg gaaaacttca tgaaacgttc ttcggtattc | 540 |
| aagggacaaa agggaactgc cgatattggt cccgctatgg ctgaaatcac catctatacc | 600 |
| gcttcgcata ctctacaagg aaaggaagtc cgtgatcgat ttgatactac tttcgcctct | 660 |
| ctctaccacg accttgatat gggctttagt cccatcaact ttatgcttca ctgggctcct | 720 |
| cttcctcaca accgtgcccg cgaccatgcg cagagaactg tcgcagcaac atatatggat | 780 |
| attattaaaa aacgacgtgc tcaggctacg gaagccgact tcaaatccga cattatgtgg | 840 |
| caattgatgc gctcgtccta caaagatgga accccgttc cagaccgaga gattgctcac | 900 |
| atgatgatcg ctcttctcat ggccggacag cactcttcct catcttctat ctcttggatt | 960 |
| ctgcttcgtc ttgcctcacg cccagatatc atggaagaac tctatcaaga acaaatccaa | 1020 |
| gttctgggcg ccgatctccc tgctctcaag tacgaggacc tggccaaact tcctcttcat | 1080 |
| caaaacatct tgaaggaaac tctccgcatc cacactccca tccattctat tatgcgcaaa | 1140 |
| gtcacaacac caatgccaat tagcggaaca aaatatgtca ttccaacctc gcatactctt | 1200 |
| atggcatctc ctggttgtac aagtcgagac gcggattact tcccagagcc acttgagtgg | 1260 |
| gaccctcata gatgggacat tggctcgggc cgtgtaattg gcaatgatca ggacgaagaa | 1320 |
| ttccaagatt atggctatgg aatgatcagc aaaggtgctt ctagtcctta ccttccattc | 1380 |
| ggtgctggca gacacaggtg tatcggtgaa caattcgcca atgtacagct catcactatc | 1440 |
| atggccactg tggttagaat gttcaaattc aagaacgttg atggcagcaa ggatgtcatt | 1500 |
| ggtactgatt acaccagttt attcaccagg ccattggcgc cagcagttat agcatgggag | 1560 |
| cgacgataa | 1569 |

<210> SEQ ID NO 18
<211> LENGTH: 1587
<212> TYPE: DNA
<213> ORGANISM: Phakopsora pachyrhizi

<400> SEQUENCE: 18

```
atgtcttcca gcgttataat cgatcagctc tactcattct caactaccag tctcatcatc     60
acatcgctaa cttccatcct cacaatcatc gtcatcctca atgtcactaa tcagttgttg    120
ttcaaggaca ggaatacccc accgctagtc ttccacatat ttccggtgct cggctctgtg    180
ataagctatg gcatggatcc gtaccaattc tttgaggact gtcggaggaa gcatggaaat    240
gtgtttacgt ttgtgctgtt gaacaagaag gtcaccgtag ctctcggtcc ggagggaaac    300
acgttggtct taaatggaaa gctctcagag gtcaatgccg aagaagctta cacccatttc    360
actacacctg tctttggtaa ggatgtagtc taygatgtac ccaactcgat cctaatgcag    420
cagaaaaagt tcatcaaggc tggccttact actgagaaat ttaagaaata tgtggggata    480
attgttagag aarcaacaag ttacctggaa gatcatttat tctgctctcc aaatgtaaaa    540
tctgtcacta aggacgtcca tgatattact tctgagataa cgatttgtac tgcagcagca    600
actctacagg gaaaagaagt cagagaaggg ctagacaaat cctttgctaa actctatcac    660
gacctagatg gtggatttac accgttgaac tttgtttttc cgaacctgcc cttaccctcc    720
tacagacgta gggacaaggc acaggtctcg atgacaaact tttatctgaa cattctaaag    780
aaaaggagag ccgaaaacag gcaggatgag ttcaatgaca tgttggatgt cttgcaggrg    840
cagcactaca aggacggcag agctttatcg gacagggaaa ttgctcacat aatgattgcc    900
gtccttatgg ctggtcaaca cactagtgct gcgaccggcg cctggttatt gacccatctg    960
gctcattgcc ctgacttggt tgatagactg aggcgtgaac aggycgaggt ctttggtaag   1020
ggggatggta gtggagagtt ggaagatcta gattacgatc gactccaaac acctctatta   1080
aattcttgta tcaaagaggt cttacgtcta caccctccca ttcattcaat cttgcgcaaa   1140
gttaagtcac cgatccttgt tcccaaaaca ctctcctcaa ttgacaagaa caaccaatac   1200
atcataccct cttcccacta cgtcctagcc gcacctggcg tctctcagat tgatccatcg   1260
gtttgggacc atccaaaaga gttcagacca gagagatggc tatcgaactt taagaaagat   1320
aagcaggaac aggaggagga gatggttgac tacggctttg gagcgatcag cagcggagcc   1380
aattcgccct atctaccctt tggggctggt cgacatcggt gtatcggaga gcagtttgcg   1440
tacatccagt tggccgccgt tgctgttgct gtcattagga actgcgacct cgagctcgtc   1500
agaaaggagt tccctctacc tgattatacc acgatgttag ttggacccag gaaacctaca   1560
actgtgaagt ttactagaag aaattaa                                       1587
```

<210> SEQ ID NO 19
<211> LENGTH: 1569
<212> TYPE: DNA
<213> ORGANISM: Botrytis cinerea

<400> SEQUENCE: 19

```
atggggattc ttgaagctgt aaccgggcca ttggctcagg aaatttcgca gcggtcaact     60
ggcgttgttg tagctgctgg cgtggcagca ttcatcgttt tatctgtcgt tctcaatgtt    120
ttgaaccaag tgttatttgc aaaccccaat gagcctccca tggtcttcca ctggctccca    180
gtaattggca gcactatcac ttatggtatg gacccttaca aattcttctt cgattgtcgc    240
gcaaagtatg gtgacatttt cacatttgtc ttgcttggaa agaagaccac cgtatatctc    300
```

```
ggacgcaagg gcaacgactt tattctcaat ggcaagctca aggatctcaa cgcggaggag    360
atatatactg ttttgacaac ccccgtattt ggcaaagatg tagtttacga ctgcccaaat    420
gcgaagttga tggagcaaaa gaagttcatg aaaattggct tgtctacaga agctttccga    480
tcctacgtcc caatcataca aatggaggtg aaaaacttta tgaagcgttc ttcggcgttc    540
aaaggtccaa agggaactgc tgacattggt cccgctatgg ctgaaatcac catctacact    600
gcttcgcaca ctctgcaagg aaaggaagtc cgcgatcgat tcgataccte ctttgcctct    660 ctctaccacg acctcgacat gggcttcagt cctatcaact ttatgcttca ctgggcccct    720
ctccctcaca accgtgcccg cgatcatgcc cagcgaactg tagccaaaac ctatatggat    780
atcattcaaa accgacgtgc tcaagctacg gaagcagagt caaatctga tattatgtgg     840 cagttgatgc gctcgtctta caaggatgga actccagttc cagataagga aatcgctaac    900
atgatgattg ctcttctcat ggccggacaa cattcttcct catcttctat ctcgtggatt    960
atgcttcgcc tcgcctcacg cccagacatt atggaagaac tctaccaaga acaaatccaa   1020
gtcttaggtg ctgatctccc tgctctcaag tatgaggatt tgtccaaact ccctctccat   1080
cagaacgttc tcaaggaaac tctacgcctc cacaccccaa tccattctat catgcgcaaa   1140
gttaccacac caatgccaat cagcggaacc aaatatgtca ttccaacatc acatacactt   1200
atggcatctc ctggttgcac aagtcgagat gacgaattct ccccgaagc acttgagtgg    1260 gatcctcaca gatgggatct tggttccggc cgtgttgttg aaatgatca ggatgaggaa    1320 ttccaagatt atggttacgg aatgattagc aaaggcgctt ccagtcctta ccttccattt   1380
ggtgctggca gacatagatg cattggtgaa caattcgcga ctgtacagct tgtcacgatc   1440
atggcaactg tcgttagatt gttcaaattt aagaacattg atggcagcaa ggatgtgatt   1500
ggtaccgatt acgcaagttt attcaccagg ccattggcgc cagccgttgt agcttgggag   1560
cgacgataa                                                           1569

<210> SEQ ID NO 20
<211> LENGTH: 1569
<212> TYPE: DNA
<213> ORGANISM: Puccinia triticina

<400> SEQUENCE: 20
atgtcttctg tgatcggctc gctgctcgag cccatcggat ccttctcaac tttcaaccaa     60
gtgctcatct acttggtgct agccgttgtc tcgatcatct cgatcaacat cttcgaccaa    120
ttggctattc ccaaagatcc gacggctcca ccagtggtgt ttcatttgtt tccgttcatt    180
ggctcggccg tgtcctacgg aatcgacccc tacgctttct ggaatcatg caggaagaag    240 tatgggaatg tgttcacctt cgtcctcttg aacaagaaag tcaccgtcgc tctcggtctc    300
gaaggaaacg cactggtcct caacggaaaa ctatctcaag ttaatgctga agaagcttac    360
acagcactca caatcttgat gcaacaaaag aaattcgtca gtctgggtt gactaacgaa    420 aactttcgga atacgtatc actgattgcg gaggagacga taagctatct tgaagatcat    480
gtatttgaga accccaaaac gcaacagact gtgaaagata ccttcaaagt ggcttctgag    540
attactatct gcacggcctc agccaccctc aagggcccg aagtccgaga agctctcaac    600
aaatcattcg cccagttata ccatgactta gatggcggtt ttaccccttt gcattcgct   660 ttccccaact tgcccttacc atcatatcgg cgtcgagacc gggcgcaact ggcgatgcga    720
aacttctata tgaacatcat caagaagaga cgagaagata cagagaggg ccagcttgga    780 gacatgatcg atagcttaca gggccaaacg tacaaggatg gccgcccttt gaacgataaa    840
```

-continued

```
gagatcgccc acattatgat tgcccttctg atggccggcc aacacaccag tgctgctact      900
ggctcctggc tactcctgca tctcgcttct cgtcccgaca tcgtcgctga attgagacag      960
gagcagatcg acttgtttgg caaaccgggc caaactgacg atcaagaact cgaccctcta     1020
gaccttgaac gtgtccagag tcccttaatg attgcatgca tcaaggaagt cctcaggctt     1080
catcccccaa tccattctat catgcgaaag gttaaatcgc ctatcaccgt gccgaggact     1140
ttggcgtcac gcaacgagga tacaccatac ataatccctt caagcaactt tgtcttggca     1200
gcgccgggaa cagcccagct cgacggatcg atctggagct cgccccacga gttcgacccg     1260
agccgatggc tgaagctcca gtctcctttc aaggccggag agacgcagga agagatggtc     1320
gattacggct tcgggatgat cagcagtggg gctaattcgc ccttcctgcc cttcggcgcc     1380
ggccgtcatc gctgtatcgg tgaacagttc gcttacatcc agctgtctac tttcgccgct     1440
accgtcatca ggaactgcga tctcgaatta actgcccctg agttccctaa acctgattat     1500
accgttcgtt tatctctctg tctctcacac atttcgatta tcagccgtca agttgaagct     1560
catctctga                                                             1569
```

<210> SEQ ID NO 21
<211> LENGTH: 1524
<212> TYPE: DNA
<213> ORGANISM: Puccinia graminis

<400> SEQUENCE: 21

```
atgtcttccc tcatcgaccc actgatcgag ttcattggct cattctcaac cttcaatcaa       60
atcctcatct acttcctact ctccatcacc tcgatcatct ccatcaacat cttcaaccaa      120
ttggctattc ccaaagatcc gaccaccca cctgtggtct tccatctatt cccattcatc      180
ggctcagctg tgtcctacgg aatcgaccct tacgctttcc tcgaatcttg tcggaagaaa      240
tacgggaatg tcttcacctt cgtcctcttg aataaaaaag tcaccgtcgc actcggtctc      300
gaaggaaacg cattgatcct caacggaaaa ctgtctcaag ttaatgctga agaagcttac      360
acagcactca ctacacctgt gttcggaact aaaatggtct atgatacgat aagctacctc      420
gaagaccatg tatttgagaa accgaaaacg cagcaagctg tcaaagactg cttcaaagtg      480
gcatctgaga tcactatctg cacagcctca gccaccctc aaggtcccga agtccgcgaa      540
ggactcaaca aatcatttgc caatctatac cacgatttag acggcgggtt tacccccacta     600 catttcgcat tccccaacct acccttacca tcatatcgac gacgagatcg ggcgcaagtg      660
gcgatgcgca acttctacat gaacataatc cagaagagac gagaggacaa ccgagaaggc      720
cagctcggag acatgatcga cagcttgcag ggccaaacct acaaggatgg gcggccgttg      780 accgacaag agatcgctca tatcatgatt gcccttctga tggccggcca acataccagt       840
gctgccactg gatcatggct cctcctccac ctcgcctctc gcccagatat tgttgccgaa      900
ttgaggcagg aacagatcga agtgttcggc aaacctggac aaactgatga taaagaactc      960
gaccctctag acctcgaacg tgtgcagagt cccttgatgc tcgcttgcat caaggaggtc     1020
ctcagacttc atccgcccat ccattcaatc atgcgaaagg tcaaatcacc gatcactgtc     1080
ccgcgaacat agcatccca taacgaagat acgccataca tcattccgtc gagtaacttt     1140
gtcttagcag cgccggggc atcgcagatc gacccggcaa tctggagctc acctcacgag     1200
ttcgagccca gtcgatggct gaagctcacc tcgcccttca aggccggcgg gggagagaca     1260
caagaagaga tggtcgacta cggcttcgga atgatcagca gcggcgccaa ctcgcccttc     1320
```

```
ctcccottcg gcgcaggccg tcatcgctgt atcggcgaac agttcgctta ccttcagctc    1380
tctactctcg gcgctaccgt cattaggaac tgcgaactcg aactagtctc caatcagttc    1440
cctaaacctg attatactac tatgttggtc tgtcctatca aaccaagaga cgtcaagttt    1500
actaggagga acacccactc gtaa                                           1524
```

<210> SEQ ID NO 22
<211> LENGTH: 1611
<212> TYPE: DNA
<213> ORGANISM: Puccinia recondita

<400> SEQUENCE: 22

```
atgtcttctg tgatcggctc gctgctcgag cccatcggat ccttctcaac tttcaaccaa     60
gtgctcatct acttggtgct agccgttgtc tcgatcatct cgatcaacat cttcgaccaa    120
ttggctattc ccaaagatcc gacggctcca ccagtggtgt ttcatttgtt tccgttcatt    180
ggctcggccg tgtcctacgg aatcgacccc tacgctttct ggaatcatg caggaagaag     240 tatgggaatg tgttcacctt cgtcctcttg aacaagaaag tcaccgtcgc tctcggtctc    300
gaaggaaacg cactggtcct caacggaaaa ctatctcaag ttaatgctga agaagcttac    360
acagcactca cgaccctgt attcggaact gatgttgtct atgatgtccc caacgcaatc    420
ttgatgcaac aaaagaaatt cgtcaagtct gggttgacta cgaaaacttt cggaaatac    480 gtatcactga ttgcggagga gacgataagc tatcttgaag atcatgtatt tgagaacccc    540
aaaacgcaac agactgtgaa agataccttc aaagtggctt ctgagattac tatctgcacg    600
gcctcagcca ccctccaagg gcccgaagtc cgagaagctc tcaacaaatc attcgcccag    660
ttataccatg acttagatgg cggttttacc cctttgcatt tcgctttccc caacttaccc    720
ttaccatcat atcggcgtcg agaccgggcg caactggcga tgcgaaactt ctatatgaac    780
atcatcaaga agagcgaga agatgacaga gagggccagc ttggagacat gatcgatagc    840
ttacagggcc aaacgtacaa ggatggccgc cctttgaacg ataaagagat cgcccacatt    900
atgattgccc ttctgatggc cggccaacac accagtgctg ctactggctc ctggctactc    960
ctgcatctcg cttctcgtcc cgacatcgtc gctgaattga dacaggagca gatcgacttg   1020
tttggcaaac cgggccaaac tgacgatcaa gaactcgacc ctctagacct cgaacgtgtc   1080
cagagtccct taatgattgc atgcatcaag gaagtcctca ggcttcatcc cccaatccat   1140
tctatcatgc gaaaggttaa atcgcctatc accgtgccga ggactttggc gtcacgcaac   1200
gaggatacac catacataat cccttcaagc aactttgtct tggcagcgcc gggaacagcc   1260
cagctcgacg gatcgatctg gagctcgccc cacgagttcg acccgagccg atggctgaag   1320
ctccagtctc ctttcaaggc cggagagacg caggaagaga tggtcgatta cggcttcggg   1380
atgatcagca gtggggctaa ttcgcccttc ctgccttcg gcgccggccg tcatcgctgt    1440
atcggtgaac agttcgctta catccagctg tctactttcg ccgctaccgt catcaggaac   1500
tgcgatctcg aattaactgc ccctgagttc cctaaacctg attataccac catgttggtt   1560
tgtcctctga aaccaaggga catcaaattt actcgaagaa accatctctg a             1611
```

<210> SEQ ID NO 23
<211> LENGTH: 1584
<212> TYPE: DNA
<213> ORGANISM: Pyrenophora teres

<400> SEQUENCE: 23
atgggtctct tcgctgatgt cgccggccct ctggctaact ttacatccaa gtcgtccacg 60

```
cctgtcgtcg ctgccgccgc cttcgcctcc tttatcctgc tctccgtcgt cctcaatgta    120
ctcaagcagt tgctgttcaa gaaggcgaat gagccgccca tggtcttcca ttggctgcct    180
ataattggca gtacagtcac atatggcatg gatccgtatg ccttcttctt tgcgaatcac    240
aagaagtatg gcaatgtctt cacatttatt ctccttggcc gcaagatgac cgtgtgcctt    300
gacacggcgg gcaacaactt catcctaaac ggaaagatca aggacgtcaa cgccgaggag    360
atttactctc cgctgaccac ccccgtcttc ggcaaggacg tcgtgtacga ctgtccaaac    420
tcgaaactca tggagcagaa aaagtttgtc aagtatggac tcacgcagga ggccctccgt    480
tcctacgtca ccctcatcac acaagaatgc gaagacttca tgaagcgcca caaagctttc    540
aagggacaac ggggcacttt tgacgtgacc aaggtcatgg ctgagctcac catctacact    600
gcctctcgtt cgctccaggg cgaggaaatc cgcaagtcgt tcgattcaaa gtttgccgaa    660
ctgtaccacg acctcgacat gggcttttca cctgtcaact ttatgctctc atgggccccg    720
cttccccaca accgcgcacg cgacaatgca cgcgagacta tgataaagct atactctgat    780
ctggttcgca agcgcaggtc gggcgccgtg aagaaggact cacacgacat gatttggcac    840
ctgatggaat gcaagtacaa ggacggcacc caggtgccgg aacacgagat tgctggcatc    900
atgattgccc tgctcatggc tggacagcat tcgtcttcct cgaccatcgc atggatcctc    960
ctccgcctcg cgcagaaccc gcacattatt gacgaactgc ttgcggagca aacgtccatc    1020
ctaggcaaaa acctccccgc ccttacctat gacgacctcc agaagcttcc ccttcacgcc    1080
caagtcgtca aggaaaccct ccgtatccac gcccccatcc actccatcat gcgcaaggtc    1140
aagcaacctc tggttgtcga tggaacaaat tacgttgttc ccacttccca cacactcatg    1200
tcctcgcccg gtttctctgc acagctcgat acccactttg tcaacccccgc tgtctgggac    1260 ccccaccgtt gggatccaga ccaaaacaac tacgacgaag agcgcgacga cgccgatcag    1320
gagaagattg actatggctg gggtgtcgtg tccaagggaa ccaactcgcc atatcttccc    1380
tttggcgctg gacggcatcg ttgcattggt gagcaatttg cctacttgca attacagact    1440
atcctagtag cgtttgtgag agagttcaag ctcaggaatg ttggtggtag taaagacatt    1500
gttggcaccg actactccag tctcttctcc cgcccactag cacctggcat agttgagtgg    1560
gagaggcggc agaaggaatg ttag                                          1584
```

<210> SEQ ID NO 24
<211> LENGTH: 1584
<212> TYPE: DNA
<213> ORGANISM: Pyrenophora tritici

<400> SEQUENCE: 24

```
atgggtctct tcgctgatgt cgccggccct ctggctaact ttacatccaa gtcgtccacg     60
cctgtcgtcg ctgccgccgc cttcgcctcc tttatcctgc tctccgtcgt cctcaatgta    120
ctcaagcagt tgctgttcaa gaaggcgaat gagccgccca tggtcttcca ttggctgcct    180
ataattggca gtacagtcac atatggcatg gatccgtatg ccttcttctt tgcgaatcac    240
aagaagtatg gcaatgtctt cacatttatt ctccttggcc gcaagatgac cgtgtgcctt    300
gacacggcgg gcaacaactt catcctaaac ggaaagatca aggacgtcaa cgccgaggag    360
atttactctc cgctgaccac ccccgtcttc ggcaaggacg tcgtgtacga ctgtccaaac    420
tcgaaactca tggagcagaa aaagtttgtc aagtatggac tcacgcagga ggccctccgt    480
tcctacgtca ccctcatcac acaagaatgc gaagacttca tgaagcgcca caaagctttc    540
```

| | |
|---|---|
| aagggacaac ggggcacttt tgacgtgacc aaggtcatgg ctgagctcac catctacact | 600 |
| gcctctcgtt cgctccaggg cgaggaaatc cgcaagtcgt tcgattcaaa gtttgccgaa | 660 |
| ctgtaccacg acctcgacat gggcttttca cctgtcaact ttatgctctc atgggccccg | 720 |
| cttccccaca accgcgcacg cgacaatgca cgcgagacta tgataaagct atactctgat | 780 |
| ctggttcgca agcgcaggtc gggcgccgtg aagaaggact cacacgacat gatttggcac | 840 |
| ctgatggaat gcaagtacaa ggacggcacc caggtgccgg aacacgagat tgctggcatc | 900 |
| atgattgccc tgctcatggc tggacagcat tcgtcttcct cgaccatcgc atggatcctc | 960 |
| ctccgcctcg cgcagaaccc gcacattatt gacgaactgc ttgcggagca aacgtccatc | 1020 |
| ctaggcaaaa acctccccgc ccttacctat gacgacctcc agaagcttcc ccttcacgcc | 1080 |
| caagtcgtca aggaaaccct ccgtatccac gcccccatcc actccatcat gcgcaaggtc | 1140 |
| aagcaacctc tggttgtcga tggaacaaat tacgttgttc ccacttccca cacactcatg | 1200 |
| tcctcgcccg gtttctctgc acagctcgat acccactttg tcaacccgc tgtctgggac | 1260 |
| ccccaccgtt gggatccaga ccaaaacaac tacgacgaag agcgcgacga cgccgatcag | 1320 |
| gagaagattg actatggctg gggtgtcgtg tccaagggaa ccaactcgcc atatcttccc | 1380 |
| tttggcgctg acggcatcg ttgcattggt gagcaatttg cctacttgca attacagact | 1440 |
| atcctagtag cgtttgtgag agagttcaag ctcaggaatg ttggtggtag taaagacatt | 1500 |
| gttggcaccg actactccag tctcttctcc cgcccactag cacctggcat agttgagtgg | 1560 |
| gagaggcggc agaaggaatg ttag | 1584 |

<210> SEQ ID NO 25
<211> LENGTH: 1512
<212> TYPE: DNA
<213> ORGANISM: Pyrenophora tritici

<400> SEQUENCE: 25

| | |
|---|---|
| atgccctctc cccttctcct cgcatccggt ttcctcgccc tctgcatcgc ctacatcttc | 60 |
| gccaacatca tccgccagct gcttcttcca aacaccaaag aaccaccgt cgtcttccac | 120 |
| tggcttccct ggcttgggag cgccatcacc tacggcaaag accccctataa gtttctgttc | 180 |
| gccgccagag agaagcatgg agatgtcttc acctttgtcc tgctaggccg caacgtcacc | 240 |
| gttcacttgg gcgttgccgg aaacgatttt gtcttcaacg gcaaagagac acatgtcaat | 300 |
| gccgaggaaa tctacggtcc cctatgtaac cccgtcttcg gcgagggcgt cgtgtacgac | 360 |
| tgtcccaatt ccaagctcat ggaacagaaa aaattcgtca agtttggtct gacaaccgac | 420 |
| gctctcaagg cacatgtgca actgattgag caagaggtcg tagactacat caaagcctcc | 480 |
| cgagagttca agggacaatc aggcaccatc aatgtgcccc ccgtcatggc tcaaatcacc | 540 |
| atcttcaccg ccgccatcgc cttacaaggg cctgaagtgc gcagcaagct cacaaacgag | 600 |
| tttgcaagcc tataccacga tctcgacggc ggttttagtc ccatcaattt tgttctccct | 660 |
| cgcgcgccct tccccacaa catcaagaga gatcgggccc agctaaagat gcgcaagatt | 720 |
| tacgagacca tcatcgcaga acgccgcgct ggcaagatcc ctcccaccac cgacatgatc | 780 |
| agtcatctca tgcagtgctc gtataaagac ggccgtcctg tgccagactc ggaaatcgca | 840 |
| aacatgatga ttaccattct aatggcgggc cagcacaact cctccaacat tgcgtcttgg | 900 |
| atcatgttgc accttgccaa caagccgcaa ctctgcgaag agctatacca ggaacagctt | 960 |
| gatcaactgg ctgatgagca tggcaacttg cccaagctcg acctgcagac cttggagaag | 1020 |
| ctcaagctgc attctaatgt cgtcaaagag acgcttcgca tgcacaactc cattcactct | 1080 |

```
atcatgcgcc ttgtcaaaca gccactcccc gtccccaata cgtcgtggac cataccgcct    1140
ggccatgccc ttctcgcttc acctggtatc tcagcaaaca gcgaagaata cttctataac    1200
ccggataagt ggaatccaca tcgctgggac gaccgcgtca tcgaagaaga cgatgagagc    1260
gagatggtgg actacggcta tggacgcatg tccaggggta caaagagcgc ctacctcccg    1320
ttcggtggag gtcgccatcg ctgcattggc gaaaagtttg cttacctcaa cttggaagtc    1380
atcacggcga ttatggtgcg aaacttttgc tttaagaatc tcgatggtag ggagggtgtt    1440
ccaggcaccg attacagcac catgttttcg cgtccgctag agcctgccga gattgtttgg    1500
cagaggcgat ga                                                       1512

<210> SEQ ID NO 26
<211> LENGTH: 1599
<212> TYPE: DNA
<213> ORGANISM: Phaeosphaeria nodorum

<400> SEQUENCE: 26
atgggaattc tcgctgatgt cgccggaccc gtggggaact tcacctctca atcgtccacc     60
gccactctca ttgccgcggg cttcgcctcc tttatcgtcc tctccgtcgt tctcaacgtt    120
ttgaagcagc tgctgtggaa ggatcccact gcgcccccgg tcgtcttcca cctgttcccg    180
atcatcggaa gcaccgtcac gtacggcatc gacccgtaca agttcttctt cgcgcagcag    240
aagaagaagg cgcaagctaa caagagacag tatggcgatg tcttcacctt catccttctc    300
ggccgcaaga tgaccgtgtg tctcgacacc aagggcaaca acctcatcct gaacggaaag    360
ctcaaggagg tcaatgccga ggagatctac tcgccgctca ccacacccgt cttcggcaag    420
gatgtcgtct acgactgccc gaactcgaag ctcatggagc agaagaagtt cgtcaagttt    480
ggtctgaccc aggaagccct ccgctcctac gttggcatca tcacccaaga atgcgaggat    540
tttttcaagc gtcacaaggc tttcaaggga caaaagggca cttttgatgt gaccaaggtc    600
atggccgagc tcaccatcta caccgcctcc cactctcttc agggtaagga gatccgcaag    660
tcgttcgact ccaagtttgc cgaccttttac cacgatctcg atatgggctt ctctcccgtc    720
aacttcatgc tgtcatgggc ccccccttccc cacaaccgcg cccgcgacgt cgctcgcgag    780
acaatgatca agctatactc cgagattgtg cgcaagcgaa gggctggcaa cgtcaagaag    840
gactcgcatg acatgatctg gcacttgatg gactgcaagt acaaggatgg cacacaggtt    900
cctgaacacg agatcgctgg tatcatgatt gcgctgctga tggctggaca acactcctct    960
tcctccacaa tcgcctggat tattctccgt ctggcacagt accctcacct tctcgaagag   1020
cttcttgcag agcagaaggc ggtcatgggc gaggaccttc cagcagtcac ctacgaagac   1080
ctcaacaagc tgccgctaca cgcccaggtt gtcaaggaga ctcttcgcat ccacgctcct   1140
atccactcaa tcatgcgcac cgtcaaatcg cctatcgttg ttgagggaac aaactacgtt   1200
atccccactt cgcacaaccct catgtcctcc cccggctact ccgcactcct cgacagctac   1260
tttgtcaacg ctgcaacctg ggacccacat cgatgggacg ccggccagca caactacgac   1320
gaggctgaga cgacgacga cgagaagatc gactatggct ggggtgttgt ctccaaaggc   1380
acaaactcgc cttacctacc atttggtgct ggaaggcatc gatgcattgg cgagcagttc   1440
gcctacctgc agctccagac gatcctcgtc gcatttgtca gggagttcaa gttcaggaac   1500
gttaacggta gcaaggacat tgttggtaca gattacacaa gtctgttctc gagaccgctt   1560
gcacctggta cggtcgagtg ggagcgcagg gaatcatag                          1599
```

<210> SEQ ID NO 27
<211> LENGTH: 1635
<212> TYPE: DNA
<213> ORGANISM: Septoria tritici

<400> SEQUENCE: 27

```
atgggtctcc tccaggaagt cctcgcgcag ttcgacgcgc aattcggcca gaccagcctc 60
tggaaacttg tcggacttgg attcctcgcc ttcagcacgc tcgccatcct cctcaatgtc 120
ctctcacaac ttctcttccg tggcaagttg tccgatccgc cactcgtatt ccactgggtg 180
cccttcatcg gaagcaccat cacatacggc atcgacccat acaagttctt cttctcctgt 240
cgggaaaagt atggagatgt ctttacattc atcctgctgg gaaagaagac gacggtgtgc 300
ttgggcacca agggcaatga ttttattttg aatggaaaac tgaaggacgt caacgcggag 360
gagatataca gcccgctgac cactcctgtc tttggcaagg atgtggttta tgattgtccc 420
aattcgaagc tcatggagca gaagaagttc gtcaagtacg gcctcacaac ctctgccctc 480
cagtcctacg tgaccttgat cgccgccgag acccgccagt tcttcgaccg caacaaccct 540
cataagaagt tcgcatcgac cagcggcacg atcgatctcc caccagccct cgccgaactt 600
acgatctata ctgccagccg atcattgcaa ggaaaggaag tccgcgaggg cttcgactcg 660
tctttcgcgg acctctacca ctacctcgat atgggattca caccgatcaa ctttatgctt 720
ccgtgggcgc cccttcccca gaaccgacgc cgcgattatg cgcagaagaa gatgtccgag 780
acatacatgt cgatcattca gaagagacga gagtccaaaa cgggcgaaca tgaggaagac 840
atgatccaca acttgatgca gtgcaaatac aaggacggca atgccattcc cgacaaggag 900
attgctcata tgatgattgc gctgctcatg gccggccagc actcttcatc tgcgaccgag 960
tcctggatca ctctccgcct cgcatcccgc cccgacatcc aagacgaact cctccaagaa 1020
caaaaggata tgctcggtgt gaacgccgac ggcagtatca aggagctcac atacgccaac 1080
ctctcgaaac tcaccctcct caatcaagtc gtcaaagaaa cccttcgtat tcacgctcca 1140
atccactcca ttctgcgcaa ggtcaagtct cccatgccca tcgaaggtac ggcatacgtc 1200
attccaacca cccacactct tctggccgct ccgggcacaa cgagccgcat ggacgagcac 1260
tttcccgact gcctccattg ggagccgcat cgatgggacg agagcccgtc cgagaaatac 1320
aagcacctgt ccccgacgac tgccctagga agcatcgccg aggagaaaga agactatggc 1380
tacggcctgg taagcaaggg cgcggcgtcg ccatacttac cctttggtgc gggacgacac 1440
agatgtatcg gcgagcaatt cgcgtacgtg caattgcaga ccattacagc gacgatggtt 1500
cgcgatttca agttttacaa tgtggatggc agcgacaacg tggtgggtac ggattacagc 1560
agtttgttca gccggccgct gtcgccggca gtagtaaagt gggagaggag ggaggagaag 1620
gaggagaaga actga 1635

<210> SEQ ID NO 28
<211> LENGTH: 1581
<212> TYPE: DNA
<213> ORGANISM: Cochliobolus sativus
<400> SEQUENCE: 28
atgggtctcc tggctgatgt caccggccct ctggccaact ttacatccca gtcgtccacg 60
cctgtcgtcg cttctgccgc cttcgcctcc tttatcctgc tctccgtcgt cctcaatgta 120
ctgaagcagt tgctgttcaa gaaggcgaat gagccgccca tggtcttcca ttggctgcct 180
ataattggta gtacagtcac atatggcatg gatccgtatg ccttcttctt cgcgaatcac 240

```
aagaagtatg gcaatgtctt tacatttatt cttctcggcc gcaagatgac tgtgtgtctg    300
gacacggcgg gcaacaactt catcctaaat ggaaagatca aggacgtcaa cgccgaggag    360
atttactctc ccctcaccac acccgtcttc ggcaaggacg tcgtgtatga ttgtccaaac    420
tcgaaactca tggagcagaa aaagtttgtc aagtacggtc tcacgcagga ggccctccgt    480
tcctacgtca ccctcatcac acaagaatgc gaagacttta tgaagcgcca caaggctttc    540
aagggagaaa agggcacttt tgacgtgacc aaggtcatgg ctgagctcac catctacacc    600
gcctctcgtt cgctccaggg cgaggaaatc cgcaagtctt tcgattcaaa gtttgccgaa    660
ctgtaccacg acctcgatat gggcttttcg cctataaact ttatgctctc atgggccccg    720
cttcctcaca accgcgcacg cgacaatgca cgcgagacca tgataaagct atactcggat    780
ctggttcgca agcgcaggtc gggcgccgtg aagaaggact cgcacgacat gatttggcac    840
ctgatggact gcaagtacaa ggacggcacc caggtgcccg aacacgagat tgctggcatc    900
atgattgccc tgctcatggc cggacagcat tcgtcttcct caaccatcgc atggatcctt    960
ctccgcctcg cgcagaaccc gcacgttatt gaggaattac ttgccgagca aaagtccatc   1020
ctaggcaaaa acctccccgc cctaacctac gacgacctcc agaagcttcc cctccatgcc   1080
caggttgtca aggaaaccct ccgtatccac gcccccattc actccatcat gcgcaaggtc   1140
aagcaacctc ttgttgtcga tggaacaaac tacgttgttc ccacttccca cacactcatg   1200
tcctcgcccg gtttctccgc acagctcgat acccactttg tcaaccccgc tgtctgggac   1260
ccccaccgtt gggatccaga ccaaaacaac tacgacgaag agcgcgacga cgccgaccag   1320
gagaagattg actatggctg gggtgtcgtg tccaagggaa ccaactcacc atatcttccc   1380
tttggcgctg gacggcatcg ttgtattggg gagcaattcg cctacctgca actacagact   1440
attctagtag catttgtgag agagttcaag ttcaggaacg ttggtggtag caaagacatt   1500
gttagcaccg actacaccag tctcttctcc cgcccactag cacctggcat agttgagtgg   1560
gagaggcggc agaacctata a                                              1581
```

<210> SEQ ID NO 29
<211> LENGTH: 1686
<212> TYPE: DNA
<213> ORGANISM: Ustilago maydis

<400> SEQUENCE: 29

```
atggtggcct cctcgtcttc ggcgacagcg tcgttgctcg accagctgtt tgcgcttacg     60
cctctcgccg attcttcggc ctggatcaaa accatcacgg tgctcgtttt gcttcccttg    120
ctcgcggtcg ttctcaacgt agcatcgcag cttctgcttg cgactcccaa gaatcatcct    180
ccggtggtgt tcactttgt gcctgtgatt ggatcggcga tctactatgg tatcgaccct    240
tacaagttct ttttcgaatg ccgcgaaaag tatggcgatg tgttcacgtt tgttctgctc    300
ggacgcaaga tcacggtggc gttgggaccc aaggaagca atctcgtctt taacgccaag    360
catcagcagg tgacggcaga ggacgcgtat acgcacctca ccacgcccgt gtttggcaaa    420
gaggtggtat acgatgtgcc taatgcggtg tttatggagc agaaaaagtt tgtcaaggtg    480
ggtctgtcga tcgaaaactt tcgcgtctac gtgccgcaga tcgtggatga agtgcgagag    540
tacatcaaga gcgatgcgcg tttcagcgca ctcaagacgc gcaagacgat cacagtcgat    600 attttcaag ccatgtcgga actcatcatc ctgaccgcat ccagaacgct gcagggcaag    660
gaagtcagac agggtctcga caagtcattt gcgcaactgt atcacgatct cgactcgggc    720
```

```
ttcactccga tcaactttgt gattcccaac ctgccgctgc cgagcaactt taaacgcgac      780
agggcgcaga agaaaatgtc gcagttctac caggacattg tggcgaaacg acgagctgcg      840
ggtgcatcca cgtctgccga cgacgccagt ggcgaaaacg atatgatcgc agcactgatc      900
gagcaaaagt acaagaacgg acgtgcactc agcggcgtcg agattgcaca tatgatgatt      960
gcactcttga tggcgggtca gcacacgagc agcgccacgt cgtcgtgggc gtttctgcgt     1020
ctggctagtc gacccgaaat catcgaggag ctatacgagg agcagctcaa cgtgtactct     1080
gacggacacg gtggtttgag ggaactcgac tacgagcgc aaaagacgtc ggtgcctctg      1140
ctggatgctg tggtcaaaga gacgttgcga ctgcacccgc ctctgcacag catcatgcga     1200
tatgtgaaat ccgaccttgc cgttccacct acgctctcgt cgccgacgtc gactaaatcc     1260
gagccggatg cccactatgt gattcccaag ggccactaca ttatggctgc acctggcgtg     1320
tcgcaagtgg atcctcagat ttggaagtca tcggaccagt ttgatccaca ccggtggttg     1380
gacgctacga ccgctgcggc gatgcaggac tcgggcgagg acaagcaaga ctttggcttc     1440
ggaatgatct ccaccggtgc caatagccca taccttccct ttggcgccgg aagacatcgg     1500
tgcatcggag agcagttcgc ctatctccag atcggcgtca tcctagccac cttcgtccgc     1560
atcttcaaat ggcacctcga ctccaaattc cccgatcccg actaccaaag catggtcgtc     1620
cttcccagca aaaacggttg cgccatcgtc ctcaccccc gagccgaatc cctccacctc      1680
gactag                                                                1686

<210> SEQ ID NO 30
<211> LENGTH: 1588
<212> TYPE: DNA
<213> ORGANISM: Rhynchosporium secalis

<400> SEQUENCE: 30
atgggaattt ttgaaggctg ttacagtccc gctggctcag caggtctcgc agcgcggatt        60
gggcgttgtg atcgccgctg gtttcgcagc cttcttggtc gtttctgtta ttctcaatgt       120
cctgagccag atactgttca agaaccccaa tgagcctccg attgttttcc acttcttccc       180
tatcattggt agcacagtta catacggtat tgacccttac aaattcttct tcgacaacaa       240
ggcaaagtat ggcgaagtct ttacctttat cctgctcggc aagaagacga ctgtgtacct       300
tggtacccac ggaaacgaat tcattctcaa tggaaagatt aaggatgtta atgcggagga       360
ggtctacacg gtcctgacca ccccagtctt tggaaaggat gtggtttacg attgtccgaa       420
ctataaggga agggagcaga aaaaagttta tgaaaaatcg gactttcca cagaagcctt       480 cagacttacg ttccaatcat tcaggacgaa gtcgaaacat ttatcaaggg ctcggcagca       540
ttcaaggggc ataaaggcac tgtcaacatt cctgctcaaa tggctgaaat cacaatctat       600
accgcttctc acgccctcca aggaaaggat tgccgagaca aattcgacca ctcatttgct       660
gagctwtayc acgcmctsga catgggcttt agcccgataa attttatgct tcactgggct       720
cctcttcccc ataatcgcgc acgggaccac gcacagcgaa ctgtcgccaa gcctacatg       780 gaaatcatgg agacgcgccg aaaagacaag aagagcctcg acaatatgga catcatgtcc       840
cagctcatgc gctccactta caagaatgga gttccggtcc cggatatgga aatcgcgcac       900
atgatgattg ccctgctcat ggctggacaa cattcgtcct cttcctcaag tacctggatc       960
atactcagac ttgccgctag accagatatc ttggaggagc tataccagga gcaactcgaa      1020
gtgctcggat ctgatctacc agccctacaa tacgaagatc tcgccaaact caccaagcac      1080
caaaacgttc tgaaggaggt cctgagactt cacactccta tccactccat catgcgaaaa      1140
```

| | |
|---|---|
| gtcaagagcc ctatgccaat tgcaggtact aagtttgtca tcccaacctc acacgtcctc | 1200 |
| ctcgcatcac ctggtttttc cagccgagag gctacctatt ttccctgacc cgctaaagtg | 1260 |
| gracccccay cgatgggaac ccgaatctgg tggagtcctg ggtactgagg tcgaggaaga | 1320 |
| gagctacgat tacggatacg gtcttattag caagggtgcc aagagtccat accttccatt | 1380 |
| cggagctggt agacataggt gtatcggaga gcaatttgcc aatgtgcagc tgatcactat | 1440 |
| cacagctgtc atggtacgat atttcaaatt caggaacctc gatggaagct cgaaggttgt | 1500 |
| tgagactgat tatacgagtc tattctcgag acctctagca ccggcggtgg ttgagtggga | 1560 |
| gaagagagaa aaagttaagg tttgaagg | 1588 |

<210> SEQ ID NO 31
<211> LENGTH: 1575
<212> TYPE: DNA
<213> ORGANISM: Venturia inaequalis

<400> SEQUENCE: 31

| | |
|---|---|
| atgggactcc tctctccttt gctcgcctcg ttaccgggca gcgaccgcag ttggttattt | 60 |
| tacactcttg cctccttcgg cttcaccgtt gcaatcgtcg ccgccaacct tgtcaagcaa | 120 |
| ctcttattct caaacccaaa cgaacctcca gtagtcttcc actggtttcc cttcttcggc | 180 |
| aacacggtcg tctacggcat cgatcctatc aagttttcg ccgagtgcaa ggaaaagcat | 240 |
| ggcgatatct ttaccttcat tcttcttggc aggaaaacaa cagtctacat tggtacaaag | 300 |
| ggaaacgaat tcattctcaa tggcaaacag agccatgtca acgcagagga atctatagc | 360 |
| cccctgacga cgcccgtctt cggctccgat gttgtctatg attgcccaaa ctcgaaattg | 420 |
| atggagcaaa agaagttcgt caagtacggg ctcaccaccg aagctctcaa atcctatgtc | 480 |
| accctcatcc aacaagaagt cgaagactat accaaacgct accctcaatt caaaggcgaa | 540 |
| aagggcagct cgatgtttg cgcttccatg gccgaaatca caatcttcac tgcttcccgc | 600 |
| tcactacaag gcaaggaggt tcgcgacaag tttgacgcca gctttgcaga cctcttccac | 660 |
| gatttggata tgggcttctc tcctatcaac ttcatgcttc cctgggcccc tcttccacac | 720 |
| aatcgtcgcc gagatgccgc gaacaaaaag atgacggaga catatttgga aattatccaa | 780 |
| tcgagaaaag cagagggcgt caaaaaggat tcagaggaca tgatttggaa tttgatgcag | 840 |
| tgtgtataca agaatggcac tcccatcccg gacaaagaaa tcgcccacat gatgatcgcg | 900 |
| ctgctcatgg ccggccagca ctcgtcctct agcacctcgt cctggattct acttcgacta | 960 |
| gctaccagac ctgatatcca ggaagaacta taccaagaac aaattcgggt ttgcggcgct | 1020 |
| gatcttccac cgttgcagta cgaagatctt gctcgcatgc ctctccacaa ccagattatc | 1080 |
| aaagaaactc ttcgcatgca ttcgccaatt cacagcatct tgcgtgccgt caaacagcct | 1140 |
| atgcctgtcg aaggaactcc ttacaccatc cccacctcgc atgttctcct tgctgctccc | 1200 |
| atcgcatctg gaggctcgcc aatgtacttt ccagctcctg agaagtggga gcctcaccgt | 1260 |
| tgggacgaag gatcaggagg aaccaacatc tcggcggcg aaaacggtgg cgaagagaaa | 1320 |
| gaggattacg gctatggact catcacaaag ggcgccagct cgccgtacct tccgttcggc | 1380 |
| gctggaagac ataggtgtat cggcgaacaa tttgcatata tgcagttgaa cacggttctc | 1440 |
| gcgacgcaag ttcgcgaatt caagttcagt ttgagggaag gagagtcgtt ccccaagacc | 1500 |
| gacttctctt ctctattttc tggacctcta cgccccgcgt ggttgaactg ggaacgtaga | 1560 |
| gagaagtcct catga | 1575 |

<210> SEQ ID NO 32
<211> LENGTH: 21
<212> TYPE: DNA
<213> ORGANISM: artificial sequence
<220> FEATURE:
<223> OTHER INFORMATION: primer

<400> SEQUENCE: 32
cggtccattg acaatccccg t                                              21

<210> SEQ ID NO 33
<211> LENGTH: 20
<212> TYPE: DNA
<213> ORGANISM: artificial sequence
<220> FEATURE:
<223> OTHER INFORMATION: primer

<400> SEQUENCE: 33
gcagcaaact cggcagtgag                                                20

<210> SEQ ID NO 34
<211> LENGTH: 24
<212> TYPE: DNA
<213> ORGANISM: artificial sequence
<220> FEATURE:
<223> OTHER INFORMATION: primer

<400> SEQUENCE: 34
gacgtccagc aagtttgacg agtc                                           24

<210> SEQ ID NO 35
<211> LENGTH: 26
<212> TYPE: DNA
<213> ORGANISM: artificial sequence
<220> FEATURE:
<223> OTHER INFORMATION: primer

<400> SEQUENCE: 35
ccatggagag ttcataaggt gcttca                                         26

<210> SEQ ID NO 36
<211> LENGTH: 25
<212> TYPE: DNA
<213> ORGANISM: artificial sequence
<220> FEATURE:
<223> OTHER INFORMATION: primer

<400> SEQUENCE: 36
actagtattg aagcaccgt acaat                                           25

<210> SEQ ID NO 37
<211> LENGTH: 27
<212> TYPE: DNA
<213> ORGANISM: artificial sequence
<220> FEATURE:
<223> OTHER INFORMATION: primer

<400> SEQUENCE: 37
gagctccatt ggagcagtca taaacaa                                        27

<210> SEQ ID NO 38
<211> LENGTH: 24
<212> TYPE: DNA
<213> ORGANISM: artificial sequence
<220> FEATURE:
<223> OTHER INFORMATION: primer

```
<400> SEQUENCE: 38
aagcttcagc aagtttgacg agtc                                          24

<210> SEQ ID NO 39
<211> LENGTH: 27
<212> TYPE: DNA
<213> ORGANISM: artificial sequence
<220> FEATURE:
<223> OTHER INFORMATION: primer

<400> SEQUENCE: 39
cccgggcatt ggagcagtca taaacaa                                       27

<210> SEQ ID NO 40
<211> LENGTH: 38
<212> TYPE: DNA
<213> ORGANISM: artificial sequence
<220> FEATURE:
<223> OTHER INFORMATION: primer

<400> SEQUENCE: 40
taatacgact cactataggg cagcaagttt gacgagtc                           38

<210> SEQ ID NO 41
<211> LENGTH: 40
<212> TYPE: DNA
<213> ORGANISM: artificial sequence
<220> FEATURE:
<223> OTHER INFORMATION: primer

<400> SEQUENCE: 41
taatacgact cactataggc attggagcag tcataaacaa                         40

<210> SEQ ID NO 42
<211> LENGTH: 20
<212> TYPE: DNA
<213> ORGANISM: artificial sequence
<220> FEATURE:
<223> OTHER INFORMATION: primer

<400> SEQUENCE: 42
cctttggtgc cggtagacat                                               20

<210> SEQ ID NO 43
<211> LENGTH: 20
<212> TYPE: DNA
<213> ORGANISM: artificial sequence
<220> FEATURE:
<223> OTHER INFORMATION: primer

<400> SEQUENCE: 43
cccatcgaat aaacgcaggc                                               20

<210> SEQ ID NO 44
<211> LENGTH: 22
<212> TYPE: DNA
<213> ORGANISM: artificial sequence
<220> FEATURE:
<223> OTHER INFORMATION: primer

<400> SEQUENCE: 44
tctacaccgt tctcactact cc                                            22

<210> SEQ ID NO 45
```

```
<211> LENGTH: 20
<212> TYPE: DNA
<213> ORGANISM: artificial sequence
<220> FEATURE:
<223> OTHER INFORMATION: primer

<400> SEQUENCE: 45
gcttctcttg aagtaatcgc                                          20

<210> SEQ ID NO 46
<211> LENGTH: 20
<212> TYPE: DNA
<213> ORGANISM: artificial sequence
<220> FEATURE:
<223> OTHER INFORMATION: primer

<400> SEQUENCE: 46
cgagtccctg gcactgaatg                                          20

<210> SEQ ID NO 47
<211> LENGTH: 20
<212> TYPE: DNA
<213> ORGANISM: artificial sequence
<220> FEATURE:
<223> OTHER INFORMATION: primer

<400> SEQUENCE: 47
gctcatcacc ccaaaaccgt                                          20

<210> SEQ ID NO 48
<211> LENGTH: 21
<212> TYPE: DNA
<213> ORGANISM: artificial sequence
<220> FEATURE:
<223> OTHER INFORMATION: primer

<400> SEQUENCE: 48
atctcgagcc cggtaccatg g                                        21

<210> SEQ ID NO 49
<211> LENGTH: 22
<212> TYPE: DNA
<213> ORGANISM: artificial sequence
<220> FEATURE:
<223> OTHER INFORMATION: primer

<400> SEQUENCE: 49
ctcggtgtaa tgacccttgg cc                                       22
```